US009983206B2

(12) United States Patent
Bailey et al.

(10) Patent No.: US 9,983,206 B2
(45) Date of Patent: May 29, 2018

(54) METHODS AND COMPOSITIONS FOR ENHANCING IMMUNOASSAYS

(71) Applicant: The Board of Trustees of the University of Illinois, Urbana, IL (US)

(72) Inventors: Ryan C. Bailey, Urbana, IL (US); Matthew S. Luchansky, Allison Park, PA (US); Abraham J. Qavi, Champaign, IL (US); Jared T. Kindt, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days. days.

(21) Appl. No.: 14/209,746

(22) Filed: Mar. 13, 2014

(65) Prior Publication Data
US 2014/0273029 A1 Sep. 18, 2014

Related U.S. Application Data

(60) Provisional application No. 61/788,279, filed on Mar. 15, 2013.

(51) Int. Cl.
*G01N 33/543* (2006.01)

(52) U.S. Cl.
CPC ........... *G01N 33/54373* (2013.01); *G01N 2333/5412* (2013.01); *G01N 2333/55* (2013.01)

(58) Field of Classification Search
CPC ....... G01N 33/54373; G01N 233/5412; G01N 2333/55
See application file for complete search history.

(56) References Cited

U.S. PATENT DOCUMENTS

| | | | |
|---|---|---|---|
| 4,474,893 A | 10/1984 | Reading | |
| 4,714,681 A | 12/1987 | Reading | |
| 4,925,648 A | 5/1990 | Hansen et al. | |
| 5,270,163 A | 12/1993 | Gold et al. | |
| 5,475,096 A | 12/1995 | Gold et al. | |
| 5,478,755 A | 12/1995 | Attridge et al. | |
| 5,539,082 A | 7/1996 | Nielsen et al. | |
| 5,567,588 A | 10/1996 | Gold et al. | |
| 5,573,920 A | 11/1996 | Randle | |
| 5,595,877 A | 1/1997 | Gold et al. | |
| 5,601,819 A | 2/1997 | Wong et al. | |
| 5,637,459 A | 6/1997 | Burke et al. | |
| 5,681,702 A | 10/1997 | Collins et al. | |
| 5,683,867 A | 11/1997 | Biesecker et al. | |
| 5,705,337 A | 1/1998 | Gold et al. | |
| 5,714,331 A | 2/1998 | Buchardt et al. | |
| 5,719,262 A | 2/1998 | Buchardt et al. | |
| 5,939,021 A | 8/1999 | Hansen et al. | |
| 6,043,060 A | 3/2000 | Imanishi | |
| 6,210,891 B1 | 4/2001 | Nyren et al. | |
| 6,268,490 B1 | 7/2001 | Imanishi et al. | |
| 6,583,399 B1 | 6/2003 | Hunziker et al. | |
| 7,083,920 B2 | 8/2006 | Werner et al. | |
| 7,183,759 B1 | 2/2007 | Malendevish et al. | |
| 7,391,936 B2 | 6/2008 | Pau et al. | |
| 7,528,403 B1 | 5/2009 | Borselli et al. | |
| 7,778,499 B2 | 8/2010 | Janz et al. | |
| 7,796,262 B1 | 9/2010 | Wang et al. | |
| 2002/0012930 A1 | 1/2002 | Rothberg et al. | |
| 2002/0037526 A1 | 3/2002 | Tashiro et al. | |
| 2003/0017579 A1 | 1/2003 | Corn et al. | |
| 2003/0027327 A1 | 2/2003 | Cunningham et al. | |
| 2003/0027328 A1 | 2/2003 | Cunningham et al. | |
| 2003/0039978 A1 | 2/2003 | Hannah | |
| 2003/0096302 A1 | 5/2003 | Yguerabide et al. | |
| 2003/0153023 A1 | 8/2003 | Starzl et al. | |
| 2004/0023396 A1 | 2/2004 | Boyd et al. | |
| 2004/0145752 A1 | 7/2004 | Angeley | |
| 2004/0180362 A1 | 9/2004 | Lazar et al. | |
| 2004/0191765 A1 | 9/2004 | Mozdy | |
| 2005/0014179 A1 | 1/2005 | Karlsson et al. | |
| 2005/0250094 A1 | 11/2005 | Storhoff et al. | |
| 2006/0087656 A1 | 4/2006 | Barford | |
| 2006/0119859 A1 | 6/2006 | Su et al. | |
| 2006/0182659 A1 | 8/2006 | Unlu et al. | |
| 2006/0194232 A1 | 8/2006 | Turner et al. | |
| 2006/0215165 A1 | 9/2006 | Melman | |
| 2006/0256350 A1 | 11/2006 | Nolte et al. | |
| 2007/0081163 A1 | 4/2007 | Liang et al. | |
| 2007/0147732 A1 | 6/2007 | Sanders | |
| 2007/0195321 A1 | 8/2007 | Soussaline et al. | |
| 2007/0237460 A1 | 10/2007 | Fan et al. | |
| 2008/0026394 A1 | 1/2008 | Labgold et al. | |
| 2008/0038738 A1 | 2/2008 | Weigum et al. | |

(Continued)

FOREIGN PATENT DOCUMENTS

| | | |
|---|---|---|
| CA | 2 355 816 | 6/2000 |
| CA | 2 555 962 | 9/2007 |
| EP | 0740156 A1 | 10/1996 |
| EP | 2347247 | 7/2011 |
| EP | 2635710 | 9/2013 |
| EP | 2825885 | 1/2015 |

(Continued)

OTHER PUBLICATIONS

Fortin et al., Imaging of DNA hybridization on microscopic polypyrrole patterns using scanning electrochemical microscopy (SECM): the HRP biocatalyzed oxidation of 4-chloro-1-naphthol. (2006) The Analyst, 131(2), 186-193.*

(Continued)

*Primary Examiner* — Andrea S Grossman
(74) *Attorney, Agent, or Firm* — Knobbe, Martens, Olson & Bear LLP

(57) ABSTRACT

Embodiments of the methods, compositions, and systems provided herein relate to enzymatic enhancement of immunoassays using photonic sensor arrays.

10 Claims, 20 Drawing Sheets

(56) References Cited

U.S. PATENT DOCUMENTS

| | | |
|---|---|---|
| 2008/0129997 A1 | 6/2008 | Yi et al. |
| 2008/0131939 A1 | 6/2008 | Roper |
| 2008/0138801 A1 | 6/2008 | He |
| 2008/0160622 A1 | 7/2008 | Su et al. |
| 2008/0204760 A1 | 8/2008 | Gollier et al. |
| 2009/0170212 A1 | 7/2009 | Van Dijk et al. |
| 2009/0309049 A1 | 12/2009 | Van Dijk et al. |
| 2010/0009456 A1 | 1/2010 | Prins et al. |
| 2010/0105566 A1 | 4/2010 | Bieniarz |
| 2010/0124787 A1 | 5/2010 | Nitkowski et al. |
| 2010/0165351 A1 | 7/2010 | Xu et al. |
| 2011/0045472 A1 | 2/2011 | Gunn, III |
| 2011/0275061 A1 | 11/2011 | Weidemaier et al. |
| 2012/0092650 A1 | 4/2012 | Gunn, III et al. |
| 2013/0157283 A1 | 6/2013 | Yung et al. |
| 2013/0261010 A1 | 10/2013 | Bailey et al. |
| 2013/0295688 A1 | 11/2013 | Bailey et al. |
| 2014/0070082 A1 | 3/2014 | Guo et al. |

FOREIGN PATENT DOCUMENTS

| | | |
|---|---|---|
| JP | 2924707 | 7/1999 |
| JP | 2002-526773 | 8/2002 |
| JP | 2004-354068 | 12/2004 |
| JP | 2004-361087 | 12/2004 |
| JP | 2005-140683 | 6/2005 |
| JP | 2005-321244 | 11/2005 |
| JP | 2006-029883 | 2/2006 |
| JP | 2006-153643 | 6/2006 |
| JP | 2006-267052 | 10/2006 |
| JP | 2007-309886 | 11/2007 |
| JP | 2008-057997 | 3/2008 |
| JP | 2010-518394 | 5/2010 |
| JP | 2012-507035 | 3/2012 |
| JP | 5656853 | 12/2014 |
| WO | WO 91/000360 | 1/1991 |
| WO | WO 92/000509 | 1/1992 |
| WO | WO 92/005793 | 4/1992 |
| WO | WO 92/008802 | 5/1992 |
| WO | WO 93/017715 | 9/1993 |
| WO | WO 98/039352 | 9/1998 |
| WO | WO 99/014226 | 3/1999 |
| WO | WO 00/020861 | 4/2000 |
| WO | WO 00/056746 | 9/2000 |
| WO | WO 00/056748 | 9/2000 |
| WO | WO 00/066604 | 11/2000 |
| WO | WO 01/000641 | 1/2001 |
| WO | WO 01/001455 | 1/2001 |
| WO | WO 03/052097 | 6/2003 |
| WO | WO 2005/066612 A2 | 7/2005 |
| WO | WO 2005/080602 A2 | 9/2005 |
| WO | WO 2007/081163 | 7/2007 |
| WO | WO 2008/054170 | 5/2008 |
| WO | WO 2008/081719 | 7/2008 |
| WO | WO 2008/097199 | 8/2008 |
| WO | WO 2009/069009 A1 | 6/2009 |
| WO | WO 2009/075473 A1 | 6/2009 |
| WO | WO 2009/076323 A2 | 6/2009 |
| WO | WO 2009/076323 A3 | 6/2009 |
| WO | WO 2010/062627 | 6/2010 |
| WO | WO 2011/091037 A2 | 7/2011 |
| WO | WO 2012/061778 A2 | 5/2012 |
| WO | WO2012/061778 A2 | 5/2012 |
| WO | WO 2013/138251 A1 | 9/2013 |
| WO | WO 2014/143637 A | 9/2014 |

OTHER PUBLICATIONS

Ihenetu et al., Pharmacological characterisation of cannabinoid receptors inhibiting interleukin 2 release from human peripheral blood mononuclear cells, European Journal of Pharmacology 464 (2003) 207-215.*

Parker et al., Monoclonal Antibodies against the Human Epidermal Growth Factor Receptor from A431 Cells, The Journal of Biological Chemistry, 259(15), 9906-9912, 1984.*

Schuler et al., A disposable and cost efficient microfluidic device for the rapid chip-based electrical detection of DNA, Biosensors and Bioelectronics 25 (2009) 15-21.*

Allen et al., "Nuclear factor-kappaB-related serum factors as longitudinal biomarkers of response and survival in advanced oropharyngeal carcinoma," *Clin. Cancer Res.* 13(11): 3182-3190, (2007).

Anderson et al., "The human plasma proteome: history, character, and diagnostic prospects," *Mol. Cell. Proteomics*, 1: 845-867, (2002).

Angelopoulos et al., "Cytokines in Alzheimer's disease and vascular dementia," *Int. J. Neurosci.*, 118(12): 1659-1672, (2008).

Anoop et al., "CSF Biomarkers for Alzheimer's Disease Diagnosis," *Int. J. Alzheimers Dis.*, 2010: 1-12, (2010).

Azevedo et al., "Stability of free and immobilised peroxidase in aqueous-organic solvents mixtures," *J. Mol. Catal. B: Enzym.*, 15: 147-153, (Nov. 2001).

Bailey et al., "A robust silicon photonic platform for maultiparameter biological analysis," *SPIE OPTO: Integrated Optoelectronic Devices*, pp. 72200N-72200N. International Society for Optics and Photonics, 2009.

Baker et al., "Plasma and cerebrospinal fluid interleukin-6 concentrations in posttraumatic stress disorder," *Neuroimmunomodulation*, 9(4): 209-217, (2001).

Bell et al., "Interleukin-6 and interleukin-10 in cerebrospinal fluid after severe traumatic brain injury in children," *J. Neurotrauma*, 14(7): 451-457, (1997).

Blennow et al., "Cerebrospinal fluid and plasma biomarkers in Alzheimer disease," *Nat Rev Neurol*, 6(3): 131-144, (2010).

Blum-Degen et al., "Interleukin-1beta and interleukin-6 are elevated in the cerebrospinal fluid of Alzheimer's and de novo Parkinson's disease patients," *Neurosci. Lett.*, 202(1-2): 17-20, (1995).

Braasch et al., "Novel antisense and peptide nucleic acid strategies for controlling gene expression," *Biochemistry*, 41(14): 4503-4510, (2002).

Byeon et al., "Efficient bioconjugation of protein capture agents to biosensor surfaces using aniline-catalyzed hydrazone ligation," *Langmuir*, 26(19): 15430-15435, (2010).

Byeon et al., "Multiplexed evaluation of capture agent binding kinetics using arrays of silicon photonic microring resonators," *Analyst*, 136(17): 3430-3433, (2011).

Capule et al., "An ELISA-based Method to Quantify the Association of Small Molecules with Aggregated Amyloid Peptides," *Anal. Chem.*, 84(3): 1786-1791, (2012).

Casebolt et al., "Monoclonal Antibody Solution Hybridization Assay for Detection of Mouse Hepatitis Virus Infection," *Journal of Clinical Microbiology*, 30(3): 608-612, (1992).

Chen et al., "Plasmon-Enhanced Colorimetric ELISA with Single Molecule Sensitivity," *Nano Lett.*, 11(4): 1826-1830, (2011).

Clark et al., "Characteristics of the microplate method of enzyme-linked immunosorbent assay for the detection of plant viruses," *J. Gen. Virol.*, 34: 475-483, (1977).

Conyers et al., "Chromogenic substrates for horseradish peroxidase," *Anal. Biochem.*, 192: 207-211, (1991).

eBioscience Enzyme Linked Immunosorbent Assay 2010, ELISA Protocols, http://www.ebioscience.com/media/pdf/best-protocols/enzyme-linked-immunosorbent-assay-elisa.pdf; 8 pages.

Ellison et al., "Standard additions: myth and reality," *Analyst*, 133: 992-997, (2008).

Engelborghs et al., "Unchanged levels of interleukins, neopterin, interferon-gamma and tumor necrosis factor-alpha in cerebrospinal fluid of patients with dementia of the Alzheimer type," *Neurochem. Int.*, 34: 523-530, (1999).

Fagan et al., "Cerebrospinal fluid biomarkers of Alzheimer's disease," *Biomarkers Med.*, 4(1): 51-63, (2010).

(56) References Cited

OTHER PUBLICATIONS

Fliss et al., "Anti-DNA.RNA antibodies: an efficient tool for non-isotopic detection of Listeria species through a liquid-phase hybridization assay," *Appl Microbiol Biotechnol*, 43(4): 717-724, (1995).
Fortin et al., "Imaging of DNA hybridization on microscopic polypyrrole patterns using scanning electrochemical microscopy (SECM): the HRP bio-catalyzed oxidation of 4-chloro-1-naphthol," *Analyst*, 131: 186-193, (2006).
Gabay, "Interleukin-6 and chronic inflammation," *Arthritis Res. Ther.*, 8(Suppl 2): S3, 6 pp., (2006).
Gauldie et al., "Interferon beta 2/B-cell stimulatory factor type 2 shares identity with monocyte-derived hepatocyte-stimulating factor and regulates the major acute phase protein response in liver cells," *Proc. Natl. Acad. Sci. U.S.A.*, 84(20): 7251-7255, (1987).
Gorris et al., "Mechanistic Aspects of Horseradish Peroxidase Elucidated through Single-Molecule Studies," *Am. Chem. Soc.*, 131(17): 6277-6282, (2009).
Hansson et al., "Association between CSF biomarkers and incipient Alzheimer's disease in patients with mild cognitive impairment: a follow-up study," *Lancet Neurol*, 5(3): 228-234, (2006).
Heath et al., "Nanotechnology and Cancer," *Annu. Rev. Med.*, 59: 251-265, (2008).
Hosoda et al., "A comparison of chromogenic substrates for horseradish peroxidase as a label in steroid enzyme immunoassay," *Chem. Pharm. Bull. (Tokyo)*, 34: 4177-4182, (1986).
Huell et al., "Interleukin-6 is present in early stages of plaque formation and is restricted to the brains of Alzheimer's disease patients," *Acta Neuropathol.*, 89(6): 544-551, (1995).
Iqbal et al., "Label-Free Biosensor Arrays Based on Silicon Ring Resonators and High-Speed Optical Scanning Instrumentation," *IEEE J. Sel. Top. Quantum Electron.*, 16(3): 654-661, (2010).
Ivanov et al., "Chip-Based Nanostructured Sensors Enable Accurate Identification and Classification of Circulating Tumor Cells in Prostate Cancer Patient Blood Samples," *Anal. Chem.*, 85(1): 398-403, (2013).
Khuseyinova et al., "Determination of C-reactive protein: comparison of three high-sensitivity immunoassays," *Clin. Chem.*, 49: 1691-1695, (2003).
Kindt et al., "Chaperone probes and bead-based enhancement to improve the direct detection of mRNA using silicon photonic sensor arrays," *Anal. Chem.*, 84(18): 8067-8074, (2012).
Konry et al., "Microsphere-based rolling circle amplification microarray for the detection of DNA and proteins in a single assay," *Anal. Chem.*, 81(14): 5777-5782, (2009).
Kostelny et al., "Formation of a bispecific antibody by the use of leucine zippers," *J. Immunol.*, 148(5): 1547-1553, (1992).
Krishnan et al., "Attomolar detection of a cancer biomarker protein in serum by surface plasmon resonance using superparamagnetic particle labels," *Agnew Chem. Int. Ed. Engl.*, 50(5): 1175-1178, (Feb. 2011).
Lafer et al., "The effect of anti-Z-DNA antibodies on the B-DNA-Z-DNA equilibrium," *J Biol Chem*, 261(14): 6438-6443, (1986).
Li et al., "Detection of protein biomarkers using RNA aptamer microarrays and enzymatically amplified SPR imaging," *Anal. Chem.*, 79(3): 1082-1088, (2007).
Llano et al., "Cerebrospinal fluid cytokine dynamics differ between Alzheimer disease patients and elderly controls," *Alzheimer Dis. Assoc. Disord.*, 26(4): 322-328, (2012).
Luchansky et al., "Silicon photonic microring resonators for quantitative cytokine detection and T-cell secretion analysis," *Anal. Chem.*, 82(5): 1975-1981, (2010).
Luchansky et al., "Rapid, multiparameter profiling of cellular secretion using silicon photonic microring resonator arrays," *J. Am. Chem. Soc.*, 133(50): 20500-20506, (2011).
Luchansky et al., "Sensitive on-chip detection of a protein biomarker in human serum and plasma over an extended dynamic range using silicon photonic microring resonators and sub-micron beads," *Lab Chip*, 11: 2042-2044, (2011).

Martinez et al., "Increased cerebrospinal fluid fas (Apo-1) levels in Alzheimer's disease. Relationship with IL-6 concentrations," *Brain Res.*, 869(1-2): 216-219, (2000).
Marz et al., "Interleukin-6 (IL-6) and soluble forms of IL-6 receptors are not altered in cerebrospinal fluid of Alzheimer's disease patients," *Neurosci. Lett.*, 239(1): 29-32, (1997).
Munge et al., "Nanostructured immunosensor for attomolar detection of cancer biomarker interlukin-8 using massively labeled supermagnetic particles," *Agnew Chem. Int. Ed. Engl.*, 50(34): 7915-7918, (Aug. 2011).
Nielsen et al., "Sequence-selective recognition of DNA by strand displacement with a thymine-substituted polyamide," *Science*, 254(5037): 1497-1500, (1991).
Olson et al., "Growth factors and cytokines/chemokines as surrogate biomarkers in cerebrospinal fluid and blood for diagnosing Alzheimer's disease and mild cognitive impairment," *Exp. Gerontol.*, 45(1): 41-46, (2010).
Palandra et al., "Highly specific and sendsitive measurements of human and monkey interleukin 21 using sequential protein and tryptic peptide immunoaffinity LC-MS/MS," *Anal. Chem.*, 85(11): 5522-5529, (2013).
Riley et al., "Stability of DNA/anti-DNA complexes. II. Salt lability and avidity," *J Immunol*, 124(1): 1-7, (1980).
Rissin et al., "Single-molecule enzyme-linked immunosorbent assay detects serum proteins at subfemtomolar concentrations," *Nat. Biotechnol.*, 28(6): 595-599, (2010).
SABiosciences Single Analyte ELISA Kits 2010, Product List, http://www.sabiosciences.com/singleelisa.php; 2 pages.
Sheehan et al., "Detection limits for nanoscale biosensors," *J. Nano Lett.*, 5(4): 803-807, (2005).
Sokolova et al., "Monocyte Chemoattractant Protein-1 Plays a Dominant Role in the Chronic Inflammation Observed in Alzheimer's Disease," *Brain Pathol.*, 19(3): 392-398, (2009).
Soleymani et al., "Hierarchical Nanotextured Microelectrodes Overcome the Molecular Transport Barrier to Achieve Rapid, Direct Bacterial Detection," *ACS Nano*, 5(4): 3360-3366, (2011).
Squires et al., "Making it stick: convection, reaction and diffusion in surface-based biosensors," *Nat. Biotechnol.*, 26(4): 417-426, (2008).
Steensberg et al., "Cerebrospinal fluid IL-6, HSP72, and TNF-alpha in exercising humans," *Brain Behav. Immun.*, 20(6): 585-589, (2006).
Stelmasiak et al., "Interleukin-6 concentration in serum and cerebrospinal fluid in multiple sclerosis patients," *Med. Sci. Monit.*, 6(6): 1104-1108, (2000).
Stollar et al., "Immunochemical approaches to gene probe assays," *Anal. Biochem.*, 161(2): 387-394, (1987).
Stollar, "Molecular analysis of anti-DNA antibodies," *FASEB J*, 8(3): 337-342, (1994).
Tarkowski et al., "Early intrathecal production of interleukin-6 predicts the size of brain lesion in stroke," *Stroke*, 26: 1393-1398, (1995).
Tarkowski et al., "Intracerebral production of tumor necrosis factor-alpha, a local neuroprotective agent, in Alzheimer disease and vascular dementia," *J. Clin. Immunol.*, 19(4): 223-230, (1999).
Tutt et al., "Trispecific F(ab')3 derivatives that use cooperative signaling via the TCR-CD3 complex and CD2 to activate and redirect resisting cytotoxic T cells," *J. Immunol.*, 147(1): 60-69, (1991).
Vandermeeren et al., "Detection of Proteins in Normal and Alzheimer's Disease Cerebrospinal Fluid with a Sensitive Sandwich Enzyme-Linked Immunosorbent Assay," *Journal of Neurochemistry*, 61(5): 1828-1834, (1993).
Veitch, "Horseradish peroxidase: a modern view of a classic enzyme," *Phytochemistry*, 65(3): 249-259, (2004).
Vollmer et al., "Whispering-gallery-mode biosensing: label-free detection down to single molecules," *Nature Methods*, 5: 591-596, (2008).
Wang et al., "Cyclohexene Nucleic Acids (CeNA): Serum Stable Oligonucleotides that Activate RNase H and Increase Duplex Stability with Complementary RNA," *J. Am. Chem. Soc.*, 122(36): 8595-8602, (2000).

(56) References Cited

OTHER PUBLICATIONS

Washburn et al., "Label-free quantitation of a cancer biomarker in complex media using silicon photonic microring resonators," *Anal. Chem.* 81(22): 9499-9506, (2009).
International Search Report and Written Opinion dated Jun. 16, 2014 in Application No. PCT/US2014/026852, filed Mar. 13, 2014.
Boguslawski et al., "Characterization of monoclonal antibody to DNA-RNA and its application to immunodetection of hybrids", *Journal of Immunological Methods*, 89 (1986) 123-130.
Cy, et al., "Cerebrospinal fluid Interleukin-6, Prostaglandin E2 and Autoantibodies in Patients with Neuropsychiatric Systemic Lupus Erythematosus and Central Nervous System Infections", 1994 Scandinavian University Press on license from Scandinavian Rheumatology Research Foundation.
Jia, et al., "Cerebrospinal fluid tau, Aβ1-42 and inflammatory cytokines in patients with Alzheimer's disease and vascular dementia", *Elsevier*, Neuroscience Letters 383 (2005) 12-16.
Vahala, Kerry J., "Optical microcavities", *Nature*, vol. 424, Aug. 14, 2003, 839-846.
Kindt J.T., et al, "Subpicogram Per Milliliter Detection of Interleukins Using Silicon Photonic Microring Resonators and an Enzymatic Signal Enhancement Strategy," Anal Chem 85:10653-10657 (2013).
Search Report and Written Opinion issued in PCT/US2014/26852, dated Jun. 16, 2014.
Supplemental Materials for Luchansky, M.S., et al, "Sensitive on-chip detection of a protein biomarker in human serum and plasma over an extended dynamic range using silicon photonic microring resonators and sub-micron beads," The Royal Society of Chemistry (Supp):1-14 (2011).
Chaperone Probes and Bead-Based Enhancement Improve the Direct Detection of mRNA Using Silicon Photonic Sensor Arrays, J.T. Kindt and R.C. Bailey, *Analytical Chemistry*, 2012, 84, 8067-8074.
High-Q Optical Sensors for Chemical and Biological Analysis, M.S. Luchansky and R.C. Bailey, *Analytical Chemistry*, 2012, 84, 793-821.
Nonlinear Analyte Concentration Gradients for One-Step Kinetic Analysis Employing Optical Microring Resonators, M.T. Marty, C.D. Kuhnline Sloan, R.C. Bailey and S.G. Sligar. *Analytical Chemistry*, 2012, 84, 5556-5564.
Label-Free Virus Detection Using Arrays of Silicon Photonic Microring Resonators, M.S. McClellan, L.L. Domier, and R.C. Bailey, *Biosensors & Bioelectronics*, 2012, 31, 388-392.
Label-free, Multiplexed Detection of Bacterial tmRNA Using Silicon Photonic Microring Resonators, O. Scheler, J.T. Kindt, A.J. Qavi, L. Kaplinski, B. Glynn, T. Barry, A. Kurg and R.C. Bailey, *Biosensors & Bioelectronics*, 2012, 36, 56-61.
Single Domain Antibodies for the Detection of Ricin Using Silicon Photonic Microring Resonator Arrays, Winnie W. Shia and R.C. Bailey, *Analytical Chemistry*, 2012, 85, 805-810.
Interfacing Lipid Bilayer Nanodiscs and Silicon Photonic Sensor Arrays for Multiplexed Protein-Lipid and Protein-Membrane Protein Interaction Screening, C.D. Kuhnline Sloan, M.T. Marty, S.G. Sligar, and R.C. Bailey, *Analytical Chemistry*, 2013, 85, 2970-2976.
'EnzMet™ HRP Detection Kit for IHC / ISH', Nanoprobes Inc., Yaphank, NY, Jan. 2008.
http://www.nanoprobes.com/products/EnzMet-SISH-enzyme-metallography-for-ISH-and-IHC.html, downloaded Jan. 19, 2017.
European Search Report dated Mar. 31, 2014 of corresponding European Patent Application No. 11838918.8—10 pages.
Office Action dated Mar. 10, 2015 in corresponding European Application No. 11838918.8, 4 pgs.
Office Action dated Oct. 13, 2015 in corresponding European Application No. 11838918.8, 4 pgs.
International Search Report dated Jun. 16, 2010 for International Patent Application No. PCT/US2009/062268.
International Search Report and Written Opinion issued May 24, 2013 in corresponding PCT Application No. PCT/US2013/030274.
International Preliminary Report on Patentability and Written Opinion dated May 3, 2011 for International Patent Application No. PCT/US2009/062268.
International Search Report and Written Opinion dated Jun. 1, 2012 in Application No. PCT/US2011/59454, 22pgs.
Office Action dated Jan. 14, 2014 in corresponding Japanese Application No. 2011-534688, 20 pgs.
Decision to Grant dated Sep. 24, 2014 in corresponding Japanese Application No. 2011-534688, 3 pgs.
Office Action dated Oct. 20, 2015 in corresponding Japanese Application No. 2014-238245, 3 pgs.
International Written Opinion dated May 26, 2009 in Application No. PCT/US2008/085988, 4 pgs.
European Search Report dated Jul. 25, 2017 in EP Application No. 08858855.3, 14 pgs.
European Search Report dated Oct. 18, 2017 in EP Application No. 17185137.1, 9 pgs.
Office Action in corresponding Japanese application No. 2014-238245 dated Jul. 26, 2016, 9 pgs.
Partial Supplementary European Search Report dated Nov. 6, 2017 in EP Application No. 09829607.2, 14 pgs.
Supplementary European Search Report dated Jan. 8, 2016 in corresponding European Application No. EP 13760958, 9 pgs.
Agnew, H D; Rohde, R D; Millward, S W; Nag, A; Yeon, W-S; Hein, J; Pitram, S M; A.A., T; Burns, V M; Krom, R J; Fokin, V V; Sharpless, K B; Heath, J R Iterative in Situ Click Chemistry Creates Antibody-like Protein-Capture Agents. Angew. Chern. 2009, 48,4944-4948.
Armani, A.M.; Kulkarni, R.P.; Fraser, S.E.; Flagan, R.C.; Vahala, K.J. Label-free single-molecule detection with optical m icrocavities. Science 2007, 317,783-787.
Bachhawat-Sikder, K; Kodadek, T Mixed-Element Capture Agents: A Simple Strategy for the Construction of Synthetic, High-Affinity Protein Capture Ligands. J. Arn. Chern. Soc. 2003, 125,9550-9551.
Bailey er al. A Robust Silicon Phtotonic Platform for Multiparameter Biological Analysis. Proc. of SPIE. 2009, vol. 7220, p. 72200N-6. (Table of Conents for Proc. of SPIE. 2009, vol. 7220 uploaded to establish priority and avialable from <http://spie.org/x648.html?product_id=799296&origin_id=x4325&start_volume_number=7200&end_volume_number=7299&start_at=21>) esp: abstract, p. 72200N-4 first paragraph; p. 72200N-2 top of page; p. 72200N-3 first paragraph; Figs, 5, 6, 7.
Bailey, R C; Hupp, J T Large-Scale Resonance Amplification of Optical Sensing of Volatile Compounds with Chemoresponsive Visible-Region Diffraction Gratings. J. Am. Chern. Soc. 2002, 124, 6767-6774.
Bailey, R C; Kwong, G A; Radu, C G; Witte, 0 N; Heath, J R DNA-Encoded Antibody Libraries: A Unified Platform for Multiplexed Cell Sorting and Detection of Genes and Proteins. J. Am. Chern. Soc. 2007, 129, 1959-1967.
Bailey, R C; Nam, J-M; Mirkin, C A; Hupp, J T Real-Time Multicolor DNA Detection with Chemoresponsive Diffraction Gratings and Nanoparticle Probes. J. Am. Chern. Soc. 2003, 125, 13541-13547.
Bailey, R C; Parpia, M; Hupp, J T Sensing via Optical Interference. Materials Today 2005, 8, 46-52.
Bayley, H.; Martin, C.R. Resistive-Pulse Sensing—From Microbes to Molecules. Chern. Rev. 2000, 100, 2575-2594.
Bayley, H; Cremer, P S Stochastic sensors inspired by biology. Nature 2001, 413, 226-230.
Berezovski, M.; Nutiu, R.; Li, Y.; Krylov, S.N. Affinity Analysis of a Protein-Aptamer Complex Using Nonequilibrium Capillary Electrophoresis of Equilibrium Mixtures. Ana/. Chern. 2003, 75, 1382-1386.
Boozer, C; Kim, G; Cong, S; Guan, H; Londergan, T Looking towards label-free biomolecular interaction analysis in a high-throughput format: a review of new surface plasmon resonance technologies. Curro Op. Biotech. 2006, 17, 400-405.
Brody, EN; Gold, L Aptamers as therapeutic and diagnostic agents. J. Biotechol. 2000, 74,5-13.
Byeon, J-Y; Bailey, R C Label-Free, Multiplexed Determination of Aptamer and Antibody Capture Agent Binding Affinities Using

(56) References Cited

OTHER PUBLICATIONS

Silicon Photonic Microring Resonator Arrays and Implications for Sensitive Biomolecule Detection. Chem. Commun., 136, 3430-3433, 2011.

Cao, L.; Chen, H.-Z.; Zhu, L.; Zhang, X.-B.; Wang, M. Optical absorption and structural studies of erbium biphthalocyanine sublimed films. Mater. Lett. 2003, 57, 4309-4314.

Chao, C.-Y.; Guo, L.J. Biochemical sensors based on polymer microrings with sharp asymmetrical resonances. Appl. Phys. Lett. 2003, 83, 1527-1529.

Coultee F., et al., "Immunodetection of DNA with biotinylated RNA probes: A study of reactivity of a monoclonal antibody to DNA-RNA hybrids", Analytical Biochemistry, Elsevier, Amsterdam, NL, vol. 181, No. 1, Aug. 15, 1989, pp. 95-105.

Eddowes, M J Direct immunochemical sensing: basic chemical principles and fundamental limitations. Biosensors 1987, 3, 1-15.

Elia, G; Silacci, M; Scheurer, S; Scheuermann, J; Neri, 0 Affinity-capture reagents for protein arrays. Trends Biotech. 2002, 20, S19-S22.

Ellington, A.D.; Szostak, J.W. In vitro selection of RNA molecules that bind specific ligands. Nature 1990,346,818-822.

Engvall, E; Perlmann, P Enzyme-linked immunosorbent assay (ELISA) quantitative assay for immunoglobulin G. Immunochem 1971, 8,871-874.

Erlanson, D A; Iam, J W; Wiesmann, C; luong, T N; Simmons, R I; Delano, W I; Choong, I C; Burdett, M T; Flanagan, W M; lee, D; Gordon, E M; O'Brien, T In situ assembly of enzyme inhibitors using extended tethering. Nature Biotech. 2003, 21, 308-314.

Fang, W.; Bucholz, D.B.; Bailey, R.C.; Hupp, J.T.; Chang, R.P.H.; Cao, H. Detection of Chemical Species Using Ultraviolet Microdisk Lasers. Appl. Phys. Lett. 2004, 85, 3666-3668.

Ge, Y; Turner, A P F Molecularly Imprinted Sorbent Assays: Recent Developments and Applications. Chern. Eur. J. 2009, 15, 8100-8107.

Gijs et al: Microfluidic Application of Magentic Particles for Biological Analysis and Catalysis:, Chemical Review, American Chemical Society, US, vol. 110, No. 3, Jan. 1, 2010 (Jan. 1, 2010), pp. 1518-1563, XP007917138, ISSN: 0009-2665, DOI: 10.1021/CR9001929 [retrieved on Apr. 12, 2009].

Gulberg, M; Fredriksson, S; Taussig, M; Jarvius, J; Gustafsdottir, S; Landegren, U A sense of closeness: protein detection by proximity ligation. Curro Op. Biotech. 2003, 14, 82-86.

Hao, E; Bailey, R C; Hupp, J T; Schatz, G C; Li, S Synthesis and Optical Properties of 'Three-Pointed' Star-Shaped Gold Nanoparticles. Nano. Lett. 2004, 4, 327-330.

Hao, E. Li, S. Bailey, R C; Zou, S; Schatz, G C; Hupp, J T The Optical Properties of Metal Nanoshells. J. Phys. Chern. B. 2004, 108, 1224-1229.

Heyduk, E; Dummit, B; Chang, Y-H; Heyduk, T Molecular Pincers: Antibody-Based Homogeneous Protein Sensors. Anal. Chem. 2008, 80,5152-5159.

Homola, J; Vee, S S; Gauglitz, G Surface plasmon resonance sensors: review. Sens. Actuators B. 1999, 54,3-15.

http://www.luminexcorp.com/ webpage, downloaded Jun. 1, 2015.

Kajiura M et al: "Biosensing by optical waveguide spectroscopy based on localized surface plasmon resonance of gold nanoparticles used as a probe or as a label", Journal of Colloid and Interface Science, Academic Press, New York, NY, US, vol. 335, No. 1,Jul. 1, 2009 (Jul. 1, 2009), pp. 140-145.

Kodadek, T Protein microarrays: prospects and problems. Chem. Biot. 2001, 8, 105-115.

Kodadek, T; Reddy, M M; Olivos, H J; Bach hawat-Si kder, K; Alluri, P G Synthetic Molecules as Antibody Replacements. Acc. Chem. Res. 2004,37,711-718.

Krasinski, A; Radic, Z; Manetch, R; Raushel, J; Taylor, P; Sharpless, K B; Kolb, H C In Situ Selection of lead Compounds by Click Chemistry: Target-Guided Optimization of Acetylcholinesterase Inhibitors. J. Am. Chern. Soc. 2005, 127, 6686-6692.

Krioukov, E.; Klunder, D.J.W.; Driessen, A; Greve, J.; Otto, C. Sensor based on an integrated optical microcavity. Opt. Lett. 2002, 27, 512-514.

Ladd, J; Zhang, Z; Chen, S; Hower, J C; Jiang, S Zwitterionic Polymers Exhibiting High Resistance to Nonspecific Protein Adsorption from Human Serum and Plasma. Biomacromolecules 2008, 9, 1357-1361.

Luchansky et al: "Sensitive on-chip detection of a protein biomarker in human serum and plasma over an extended dynamic range using silicon photonic microring resonators and sub-micron beads", Lab on a Chip, vol. 11, No. 12, Jan. 1, 2011 (Jan. 1, 2011), p. 2042.

Luchansky et al: "Silicon Photonic Microring Resonators for Quantitative Cytokine Detection and T-Cell Secretion Analysis", Analytical Chemistry, vol. 82, No. 5,Mar. 1, 2010 (Mar. 1, 2010), pp. 1975-1981.

Luchansky, M S; Washburn, A L; Martin, T A; Iqbal, M; Gunn, L C; Bailey, R C Characterization of the evanescent field profile and bound mass sensitivity of a label- free silicon photonic microring resonator biosensing platform. Biosens. Bioelectron.2010, doi:1 0.1016/j.bios.201 0.1 007.1 010.

Luxton R. et al: "Use of External Magnetic Fields to Reduce Reaction Times in an Immunoassay Using Micrometer-Sized Paramagentic Particles as Labels (Magentoimmunoassay)", Analytical Chemistry, Americal Chemical Society, US, vol. 76, No. 6, Mar. 15, 2004 (Mar. 15, 2004), pp. 1715-1719, XP001196657, ISSN: 0003-2700, DOI: 10.1021/AC034906+.

Manetsch, R; Krasinski, A; Radic, Z; Raushel, J; Taylor, P; Sharpless, K B; Kolb, H C In Situ Click Chemistry: Enzyme Inhibitors Made to Their Own Specifications. J. Arn. Chern. Soc. 2004, 126, 12809 12818.

McKendry, et al. Multiple Label-Free Biodetection and Quantative DNA-Binding assays on Nanomechanical Cantilever Array, PNAS, Jul. 23, 2002, vol. 99, No. 15, paged 9783 to 9788. See pp. 9783 to 9785.

Naffin J I; Han, Y; Olivos, H J; Reddy, M M; Sun, T; Kodadek, T Immobilized Peptides as High-Affinity Capture Agents for Self-Associating Proteins. Chern. Biol. 2003, 10, 251-259.

Niemeyer, C M Semisynthetic DNA-Protein Conjugates for Biosensing and Nanofabrication. Angew. Chern. Inti. Ed. 2010, 49, 1200-1216.

Niemeyer, C M; Adler, M; Wacker, R Detecting antigens by quantitative immuno-PCR. Nature Protocols 2007, 2, 1918-1930.

Palik, E, Ed. Handbook of Optical Constants of Solids; Academic Press: San Diego, CA,1998. pp. 1-12.

Perez-Luna, V.H.; O'Brien, M.J.; Opperman, K.A.; Hampton, P.O.; Lopez, G.P.; Klumb, L.A.; Stayton, P.S. Molecular Recognition between Genetically Engineered Streptavidin and Surface-Bound Biotin. J. Am. Chern. Soc. 1999, 121,6469-6478.

Phelan, M L; Nock, S Generation of bioreagents for protein chips. Proteomics 2003, 3, 2123-2134.

Pierres, A.; Touchard, D.; Benoliel, A.-M.; Bongrand, P. Dissecting Steptavidin-Biotin Interaction with a Laminar Flow Channel. Biophys. J. 2002, 82, 3214-3223.

Qavi et al: "Anti-DNA:RNA Antibodies and Silicon Photonic Microring Resonators: Increased Sensitivity for Multiplexed micro RNA Detection", Analytical Chemistry, vol. 83, No. 15, Aug. 1, 2011 (Aug. 1, 2011), pp. 5949-5956.

Qavi, A J; Bailey, R C Multiplexed Detection and Label-Free Quantitation of MicroRNAs Using Arrays of Silicon Photonic Microring Resonators. Angew. Chem. 2010, 49,4608-4611.

Qavi, A J; Mysz, T M; Bailey, R C Label-Free Detection of DNA and Isothermal Discrimination of Single Nucleotide Polymorphisms via Kinetic Desorption Rates using Silicon Photonic Microring Resonator Arrays. J. Am. Chem. Soc. 6827-6833, 2011.

Qavi, A J; Washburn, A L; Byeon, J-Y; Bailey, R C Label-free technologies for quantitative multiparameter biological analysis. Anal. Bioanal. Chem. 2009, 394, 121-135.

Ramachandran, et al. A Universal Biosensing platform Based on Optical Micro-rin resonators, Biosensors and Bioelectronics, Sep. 21, 2007, vol. 23, pp. 939 to 944. Se abstract, pp. 940 to 942.

Reddy, M M; Bachhawat-Sikder, K; Kodadek, T Transformation of Low-Affinity Lead Compounds into High-Affinity Protein Capture Agents. Chem. Biol. 2004, 11, 1127-1137.

(56) References Cited

OTHER PUBLICATIONS

Scheck, R A; Francis, M B Regioselective Labeling of Antibodies through N-Terminal Transamination. ACS Chem. Biol. 2007, 2, 247-251.

Schmidt, J. Stochastic sensors. J. Mater. Chem. 2005, 15,831-840.

Sipova et al., "Surface Plasmon Resonance Biosensor for Radi Label-Free Detection of Microribonucleic Acid at Subfemtomole Level", Analytical Chemistry, vol. 82, No. 24, Dec. 15, 2010, pp. 10110-10115.

Soderberg, 0; Leuchowius, K-J; Kamali-Moghaddam, M; Jarvius, M; Gustafsdottir, S; Schall meiner, E; Gullberg, M; Jarvius, J; Landegren, U Proximity Ligation: A Specific and Versatile Tool for the Proteomic Era. Genetic Eng. 2007, 28, 85-93.

Song et al. "Detection of Oligonucleotide Hybridization at Femtomolar Level and Sequence-Specific gene analysis of the *Arabidopsis thaliana* Leaf Extract with an Unitrasensitive Surface Plasmon Resonance Spectrometer" Nucleic Acids Research, 2002, 30(14): e72, pp. 1-11.

Stuart, 0 A; Haes, A J; Yonzon, C R; Hicks, E M; Van Duyne, R P Biological Applications of Localized Surface Plasmon Resonance Phenomena. IEEE Proc.—Nanobiotechnol.2005, 152, 13-32.

Su, X.-C.; Huber, T.; Dixon, N.E.; Otting, G. Site-Specific Labelling of Proteins with a Rigid Lanthanide-Binding Tag. ChemBioChem 2006, 7, 1599-1604.

Sun, Y S; Landry, J P; Fei, Y Y; Zhu, X 0; Luo, J T; Wang, X B; Lam, K S Effect of Fluorescently Labeling Protein Probes on Kinetics of Protein-Ligand Reactions. Langmuir 2008, 24, 13399-13405.

Thaxton, C S; Rosi, N L; Mirkin, C A Optically and chemically encoded nanoparticie materials for DNA and protein detection. MRS Bulletin 2005, 30, 376-380.

Tsai et al., "Cerebrospinal fluid interleukin-6, prostaglandin E2 and autoantibodies in patients with neuropsychiatric systemic lupus erythematosus and central nervous system infections," Scand. J. Rheumatol., 23(2): 57-63, (1994).

Tuerk, C.; Gold, L. Systematic evolution of ligands by exponential enrichment: RNA ligands to bacteriophage T4 DNA polymerase. Science 1990, 249, 505-510.

Turner, E.H.; Cohen, D.; Pugsley, H.R.; Gomez, D.G.; Whitmore, C.D.; Zhu, C.; Dovichi, N.J. Chemical cytometry: the chemical analysis of single cells. Anal. Bioanal. Chem. 2008, 390, 223-226.

Vollmer, et al. Multiplexed DNA Qualification by Spectoscopic Shift of Two Microsphere Cavities, Biophysical Journal, Sep. 2003, vol. 85, pp. 1974 to 1979. See pp. 1974 to 1977.

Vollmer, F.; Braun, D.; Libchaber, A; Khoshima, M.; Teraoka, I.; Arnold, S. Protein detection by optical shift of a resonant microcavity. Appl. Phys. Lett. 2002, 80, 4057-4059.

Washburn, A L; Luchansky, M S; Bowman, A L; Bailey, R C Quantitative Multiplexed Detection of Five Protein Biomarkers Using Arrays of Silicon Photonic Microring Resonators. Anal. Chem. 2010, 82,69-72.

Wayment, J.R.; Harris, J.M. Controlling Binding Site Densities on Glass Surfaces. Ana/. Chem. 2006, 78,7841-7849.

Wolfbeis, 0 S Fiber-Optic Chemical Sensors and Biosensors. Anal. Chem. 2002, 74, 2663-2678.

Wolter, A; Niessner, R; Seidel, M Preparation and Characterization of Functional Poly(ethylene glycol) Surfaces for the Use of Antibody Microarrays. Anal. Chem. 2007, 79,4529-4537.

Z. Li, et al. Sequence-Specific Label Free DNA Sensors Based on Silicon Nanowires, Nano Lett., Aug. 1, 2004, vol. 4, No. 2, pp. 245 to 247. See pp. 246-247.

\* cited by examiner

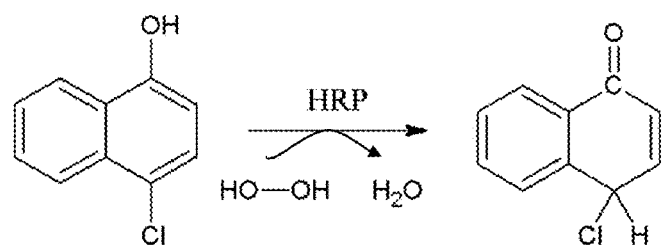
FIG. 4
FIG. 5
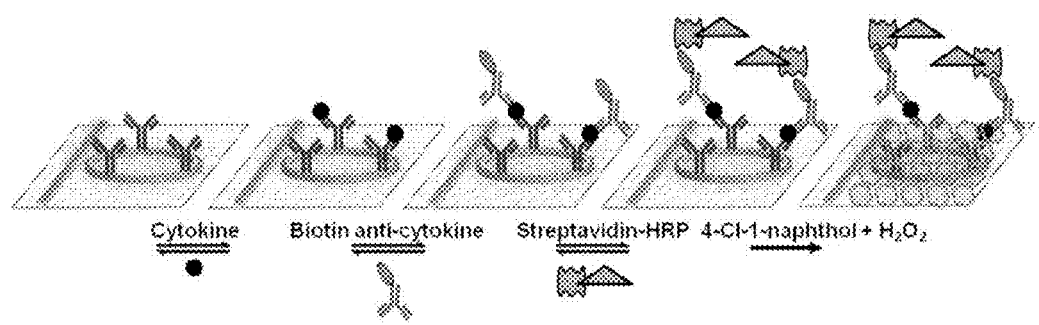

US 9,983,206 B2

METHODS AND COMPOSITIONS FOR ENHANCING IMMUNOASSAYS

CROSS-REFERENCE TO RELATED APPLICATIONS

This application claims priority to U.S. Provisional Application No. 61/788,279 filed on Mar. 15, 2013 entitled "ENZYMATIC ENHANCEMENT OF IMMUNOASSAYS FOR ULTRASENSITIVE DETECTION USING PHOTONIC SENSOR ARRAYS" the contents of which is incorporated herein in its entirety.

STATEMENT REGARDING FEDERALLY SPONSORED R&D

This invention was made with United States Government support under Grant No. NSF CHE 12-14081 awarded by the National Science Foundation. The United States Government has certain rights in the invention.

FIELD OF THE INVENTION

Embodiments of the methods, compositions, and systems provided herein relate to enzymatic enhancement of immunoassays using photonic sensor arrays.

BACKGROUND OF THE INVENTION

Robust biomolecule quantitation is central to biomarker based clinical diagnostics, driving the development of high throughput, low cost medical diagnostic devices based on a myriad of biosensing technologies. Chief among the many relevant performance metrics of these devices is the ability to quantitate extremely low abundance analytes, such as picograms per milliliter and less, in complex matrices and in a multiplexed format (Heath, J. R.; Davis, M. E. Annu. Rev. Med. 2008, 59, 251-265). Regardless of the specific architecture or transduction methodology, affinity-based biosensors face limitations imposed by the Langmuir binding isotherm, which defines the ratio of solution-phase analyte to surface-bound analyte, as determined by the affinity of the capture agent employed. FIG. 1. At low concentrations, the amount of bound analyte is directly proportional to the solution sample concentration, as shown in eq 1, where $\theta_{eq}$ is the equilibrium surface coverage, $K_{ads}$ is the equilibrium binding constant, and [C] is the solution-phase analyte concentration:

$$\theta_{eq} = \frac{K_{ads}[C]}{1 + K_{ads}[C]} \quad [1]$$

Even when using high-affinity capture agents, restrictions imposed by the Langmuir isotherm, which are further exacerbated by mass transport limitations for sensing elements with small geometric footprints, can result in only a few individual molecules being bound to the sensor surface (Squires, T. M.; Messinger, R. J.; Manalis, S. R. Nat. Biotechnol. 2008, 26, 417-426; Sheehan, P. E.; Whitman, L. J. Nano Lett. 2005, 5, 803-807). Efforts to circumvent these fundamental limitations, and thus improve detection limits, include both the development of nanostructured morphologies with increased surface areas, as well as the integration of signal enhancement schemes that boost the per target sensor response (Soleymani, L.; Fang, Z.; Lam, B.; Bin, X.; Vasilyeva, E.; Ross, A. J.; Sargent, E. H.; Kelley, S. O. ACS Nano 2011, 5, 3360-3366; Munge, B. S.; Coffey, A. L.; Doucette, J. M.; Somba, B. K.; Malhotra, R.; Patel, V.; Gutkind, J. S.; Rusling, J. F. Angew. Chem., Int. Ed. 2011, 50, 7915-7918). Nonetheless, there remains an unmet need to develop assays to detect and quantitate extremely low abundance analytes.

SUMMARY OF THE INVENTION

Some embodiments of the methods, compositions and systems provided herein include a method of detecting a target analyte comprising: (a) obtaining a planar substrate comprising an optical sensor having a first capture probe attached thereto; (b) contacting the first capture probe with a sample comprising a target analyte that selectively binds to the first capture probe; (c) contacting the bound target analyte with a second capture probe that selectively binds to a complex comprising the bound target analyte, wherein the second capture probe comprises a catalyst; (d) contacting the catalyst with a reagent under conditions where the reagent forms a precipitate in the presence of the catalyst; and (e) measuring a change in an optical property at the optical sensor, thereby detecting the target analyte.

Some embodiments of the methods, compositions and systems provided herein include a method of detecting a target analyte comprising: (a) obtaining a planar substrate comprising an optical sensor having a first capture probe attached thereto; (b) contacting the first capture probe with a sample comprising a target analyte that selectively binds to the first capture probe; (c) contacting the bound target analyte with a second capture probe that selectively binds to a complex comprising the bound target analyte, wherein the second capture probe comprises a catalyst; (d) contacting the catalyst with a reagent under conditions where the reagent forms a precipitate in the presence of the catalyst; and (e) measuring a change in resonance wavelengths at the optical sensor, thereby detecting the target analyte.

In some embodiments, the second capture probe is formed by contacting an affinity molecule bound to a first affinity tag with a second affinity tag bound to the catalyst, wherein the second affinity tag selectively binds to the first affinity tag.

In some embodiments, the second capture probe comprises an affinity molecule bound to the catalyst.

In some embodiments, the second capture probe is attached to a particle.

In some embodiments, the catalyst is attached to a particle.

Some embodiments of the methods, compositions and systems provided herein include a method of detecting a target analyte comprising: (a) obtaining a planar substrate comprising an optical sensor having a first capture probe attached thereto; (b) contacting the first capture probe with a sample comprising a target analyte that selectively binds to the first capture probe; (c) contacting the bound target analyte with a second capture probe that selectively binds to a complex comprising the bound target analyte, wherein the second capture probe comprises a first affinity tag; (d) contacting the bound second capture probe with a second affinity tag that selectively binds to the bound first affinity tag, wherein the second affinity tag comprises a catalyst; (e) contacting the catalyst with a reagent under conditions where the reagent forms a precipitate in the presence of the catalyst; and (f) measuring an increase in precipitate formation at the optical sensor, thereby detecting the target analyte.

In some embodiments, the quantity of precipitate formation is indicative of the level of the target analyte in the sample.

In some embodiments, an increase in rate of precipitate formation is indicative of the level of the target analyte in the sample.

In some embodiments, the first and second affinity tags are each selected from the group consisting of biotin, streptavidin, poly-His, and nickel.

In some embodiments, (f) comprises measuring a change in an optical property.

In some embodiments, the change in an optical property is measured by a ring resonator, and/or a wave guide structure.

In some embodiments, (f) comprises measuring a change in resonance wavelengths at the optical sensor.

In some embodiments, the first capture probe comprises an antibody or antigen-binding fragment thereof. In some embodiments, the first capture probe comprises an antibody selected from the group consisting of anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the second capture probe selectively binds to the target analyte.

In some embodiments, the second capture probe selectively binds to the bound target analyte.

In some embodiments, the second capture probe comprises an antibody or antigen-binding fragment thereof. In some embodiments, the second capture probe comprises an antibody selected from the group consisting of, anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the second capture probe is attached to a particle.

In some embodiments, the catalyst is attached to a particle.

In some embodiments, the catalyst is selected from the group consisting of horseradish peroxidase, alkaline phosphatase, and β-galactosidase. In some embodiments, the catalyst comprises horseradish peroxidase.

In some embodiments, the reagent is selected from the group consisting of 4-chloro-1-naphthol, Hanker-Yates reagent, 3,3'-diaminobenzidine, and 3-amino-9-ethylcarbazole. In some embodiments, the reagent comprises 4-chloro-1-naphthol.

Some embodiments also include contacting the catalyst with hydrogen peroxide. In some embodiments, the concentration of hydrogen peroxide is less than about 0.003%. In some embodiments, the concentration of hydrogen peroxide is less than about 0.001%.

Some embodiments also include washing the optical sensor between steps (a)-(b), (b)-(c), (c)-(d), (d)-(e), and combinations thereof.

In some embodiments, a target analyte concentration less than about 100 pg/ml is detected. In some embodiments, a target analyte concentration less than about 10 pg/ml is detected. In some embodiments, a target analyte concentration less than about 1 pg/ml is detected.

In some embodiments, the target analyte comprises a cytokine. In some embodiments, the target analyte is selected from the group consisting of IL-2, IL-4, IL-6, and IL-8.

In some embodiments, the sample comprises the target analyte. In some embodiments, the sample is selected from the group consisting of serum and cerebrospinal fluid.

In some embodiments, the optical sensor comprises an optical ring resonator.

In some embodiments, the optical sensor comprises a waveguide structure.

In some embodiments, the optical sensor comprises a well.

In some embodiments, the planar substrate comprises a plurality of optical sensors.

In some embodiments, the planar substrate comprises a thermal control.

In some embodiments, the planar substrate comprises an optical chip.

In some embodiments, the planar substrate comprises a multiwell plate.

In some embodiments, the planar substrate comprises a flowcell.

Some embodiments of the methods, compositions, and systems provided herein include a kit for detecting a target analyte comprising: a planar substrate comprising an optical sensor having a first capture probe attached thereto, wherein the first capture probe selectively binds to the target analyte; a second capture probe that selectively binds to a complex comprising the target analyte bound to the first capture probe, wherein the second capture probe comprises a catalyst; and a reagent that can form a precipitate in the presence of the catalyst.

In some embodiments, the second capture probe is formed by contacting an affinity molecule bound to a first affinity tag with a second affinity tag bound to the catalyst, wherein the second affinity tag selectively binds to the first affinity tag.

In some embodiments, the second capture probe comprises an affinity molecule bound to the catalyst.

Some embodiments of the methods, compositions, and systems provided herein include a kit for detecting a target analyte comprising: a planar substrate comprising an optical sensor having a first capture probe attached thereto, wherein the first capture probe selectively binds to the target analyte; a second capture probe that selectively binds to a complex comprising the target analyte bound to the first capture probe, wherein the second capture probe comprises a first affinity tag; a second affinity tag that selectively binds to the first affinity tag, wherein the second affinity tag comprises a catalyst; a reagent that can form a precipitate in the presence of the catalyst.

In some embodiments, the first and second affinity tags are each selected from the group consisting of biotin, streptavidin, poly-His, and nickel.

In some embodiments, the first capture probe comprises an antibody or antigen-binding fragment thereof. In some embodiments, the first capture probe comprises an antibody selected from the group consisting of anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the second capture probe selectively binds to the target analyte.

In some embodiments, the second capture probe selectively binds to the bound target analyte.

In some embodiments, the second capture probe comprises an antibody or antigen-binding fragment thereof. In some embodiments, the second capture probe comprises an antibody selected from the group consisting of, anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the second capture probe is attached to a particle.

In some embodiments, the catalyst is attached to a particle.

In some embodiments, the catalyst is selected from the group consisting of horseradish peroxidase, alkaline phosphatase, and β-galactosidase.

In some embodiments, the catalyst comprises horseradish peroxidase.

In some embodiments, the reagent is selected from the group consisting of 4-chloro-1-naphthol, Hanker-Yates reagent, 3,3'-diaminobenzidine, and 3-amino-9-ethylcarbazole. In some embodiments, the reagent comprises 4-chloro-1-naphthol.

Some embodiments also include hydrogen peroxide. In some embodiments, the concentration of hydrogen peroxide is less than about 0.003%. In some embodiments, the concentration of hydrogen peroxide is less than about 0.001%.

Some embodiments include a kit adapted to detect a target analyte concentration less than about 100 pg/ml is detected. Some embodiments include a kit adapted to detect a target analyte concentration less than about 10 pg/ml is detected. Some embodiments include a kit adapted to detect a target analyte concentration less than about 1 pg/ml is detected.

In some embodiments, the target analyte comprises a cytokine. In some embodiments, the target analyte is selected from the group consisting of IL-2, IL-4, IL-6, and IL-8.

In some embodiments, the sample comprises the target analyte. In some embodiments, the sample is selected from the group consisting of serum and cerebrospinal fluid.

In some embodiments, the optical sensor comprises an optical ring resonator.

In some embodiments, the optical sensor comprises a waveguide structure.

In some embodiments, the optical sensor comprises a well.

In some embodiments, the planar substrate comprises a plurality of optical sensors.

In some embodiments, the planar substrate comprises a thermal control.

In some embodiments, the planar substrate comprises an optical chip.

In some embodiments, the planar substrate comprises a multiwell plate.

In some embodiments, the planar substrate comprises a flowcell.

Some embodiments of the methods, compositions, and systems provided herein include a system for detecting a target analyte comprising: a planar substrate comprising an optical sensor having a first capture probe attached thereto, wherein the target analyte selectively binds to the first capture probe; a second capture probe that selectively binds to a complex comprising the target analyte bound to the first capture probe, wherein the second capture probe comprises a catalyst; a reagent which can form a precipitate in the presence of the catalyst; and a detector adapted to measure a change in an optical property at the optical sensor.

Some embodiments of the methods, compositions, and systems provided herein include a system for detecting a target analyte comprising: a planar substrate comprising an optical sensor having a first capture probe attached thereto, wherein the target analyte selectively binds to the first capture probe; a second capture probe that selectively binds to a complex comprising the target analyte bound to the first capture probe, wherein the second capture probe comprises a catalyst; a reagent which can form a precipitate in the presence of the catalyst; and a detector adapted to measure a change in resonance wavelengths at the optical sensor.

In some embodiments, a change in resonance wavelengths at the optical sensor is indicative of the level of the target analyte.

In some embodiments, the second capture probe is formed by contacting an affinity molecule bound to a first affinity tag with a second affinity tag bound to the catalyst, wherein the second affinity tag selectively binds to the first affinity tag.

In some embodiments, the second capture probe comprises an affinity molecule bound to the catalyst.

Some embodiments of the methods, compositions, and systems provided herein include a system for detecting a target analyte comprising: a planar substrate comprising an optical sensor having a first capture probe attached thereto, wherein the target analyte selectively binds to the first capture probe; a second capture probe that selectively binds to a complex comprising the target analyte bound to the first capture probe, wherein the second capture probe comprises a first affinity tag; a second affinity tag that selectively binds to the bound first affinity tag, wherein the second affinity tag comprises a catalyst; a reagent that forms a precipitate in the presence of the catalyst; and a detector adapted to measure an increase in precipitate formation.

In some embodiments, the increase in precipitate formation is indicative of the level of the target analyte in the sample.

In some embodiments, the first and second affinity tags are each selected from the group consisting of biotin, streptavidin, poly-His, and nickel.

In some embodiments, an increase in precipitate formation is measured by a change in resonance wavelengths at the optical sensor.

In some embodiments, the first capture probe comprises an antibody or antigen-binding fragment thereof. In some embodiments, the first capture probe comprises an antibody selected from the group consisting of anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the second capture probe comprises an antibody or antigen-binding fragment thereof.

In some embodiments, the second capture probe selectively binds to the target analyte.

In some embodiments, the second capture probe selectively binds to the bound target analyte.

In some embodiments, the second capture probe comprises an antibody selected from the group consisting of, anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the second capture probe is attached to a particle.

In some embodiments, the catalyst is attached to a particle.

In some embodiments, the catalyst is selected from the group consisting of horseradish peroxidase, alkaline phosphatase, and β-galactosidase. In some embodiments, the catalyst comprises horseradish peroxidase.

In some embodiments, the reagent is selected from the group consisting of 4-chloro-1-naphthol, Hanker-Yates reagent, 3,3'-diaminobenzidine, and 3-amino-9-ethylcarbazole. In some embodiments, the reagent comprises 4-chloro-1-naphthol.

Some systems also include hydrogen peroxide.

In some embodiments, the planar surface is adapted for washing the optical sensor.

In some embodiments, the system is adapted to detect a target analyte concentration less than about 100 pg/ml is detected. In some embodiments, the system is adapted to detect a target analyte concentration less than about 10 pg/ml is detected. In some embodiments, the system is adapted to detect a target analyte concentration less than about 1 pg/ml is detected.

In some embodiments, the target analyte comprises a cytokine. In some embodiments, the target analyte is selected from the group consisting of IL-2, IL-4, IL-6, and IL-8.

In some embodiments, the sample comprises the target analyte. In some embodiments, the sample is selected from the group consisting of serum and cerebrospinal fluid.

In some embodiments, the optical sensor comprises an optical ring resonator.

In some embodiments, the optical sensor comprises a waveguide structure.

In some embodiments, the optical sensor comprises a well.

In some embodiments, the planar substrate comprises a plurality of optical sensors.

In some embodiments, the planar substrate comprises a thermal control.

In some embodiments, the planar substrate comprises an optical chip.

In some embodiments, the planar substrate comprises a multiwell plate.

In some embodiments, the planar substrate comprises a flowcell.

Some embodiments of the methods, compositions, and systems provided herein include a method of detecting a target analyte comprising: (a) obtaining an optical ring resonator having a first anti-cytokine antibody attached thereto, wherein the first anti-cytokine antibody is anti-IL-2 from clone 555051 antibody; (b) contacting the first anti-cytokine antibody with a sample comprising IL-2 that selectively binds to the anti-cytokine antibody; (c) contacting the bound IL-2 with a second anti-cytokine antibody that selectively binds to the cytokine, wherein the second anti-cytokine antibody is a biotinylated anti-IL-2 from clone 555040 antibody; (d) contacting the biolinylated second anti-cytokine antibody with a streptavidin-horseradish peroxidase conjugate; (e) contacting the horseradish peroxidase with 4-chloro-1-naphthol and hydrogen peroxide under conditions that oxidize 4-chloro-1-naphthol to 4-chloro-1-naphthon, whereby the 4-chloro-1-naphthon precipitates on the surface of the optical ring resonator; and (f) measuring a change in resonance wavelengths of the optical ring resonator, thereby indicating the presence of the cytokine.

In some embodiments, the concentration of hydrogen peroxide is less than about 0.003%.

In some embodiments, a concentration of the cytokine less than about 100 pg/ml is detected.

Some embodiments of the methods, compositions, and systems provided herein include a method of detecting a target analyte comprising: (a) obtaining an optical ring resonator having a first anti-cytokine antibody attached thereto, wherein the first anti-cytokine antibody is anti-IL-6 from clone MAB206 antibody; (b) contacting the first anti-cytokine antibody with a sample comprising IL-6 that selectively binds to the anti-cytokine antibody; (c) contacting the bound IL-2 with a second anti-cytokine antibody that selectively binds to the cytokine, wherein the second anti-cytokine antibody is a biotinylated anti-IL-6 from clone BAF206; (d) contacting the biolinylated second anti-cytokine antibody with a streptavidin-horseradish peroxidase conjugate; (e) contacting the horseradish peroxidase with 4-chloro-1-naphthol and hydrogen peroxide under conditions that oxidize 4-chloro-1-naphthol to 4-chloro-1-naphthon, whereby the 4-chloro-1-naphthon precipitates on the surface of the optical ring resonator; and (f) measuring a change in resonance wavelengths of the optical ring resonator, thereby indicating the presence of the cytokine.

In some embodiments, the concentration of hydrogen peroxide is less than about 0.003%.

In some embodiments, a concentration of the cytokine less than about 100 pg/ml is detected.

BRIEF DESCRIPTION OF THE DRAWINGS

FIG. 2 schematically illustrates the range of wavelengths that may be input into the optical sensor and the resultant spectral output of the optical sensor. A decrease in the optical output at the resonance frequency of the ring resonator is visible in the output spectrum shown.

FIG. 4 depicts the horseradish peroxidase (HRP)-catalyzed oxidation of 4-Cl-1-naphthol (4-CN) by hydrogen peroxide.

FIG. 5 depicts an HRP-amplified cytokine immunoassay on a microring resonator platform.

DETAILED DESCRIPTION

Figure 1:
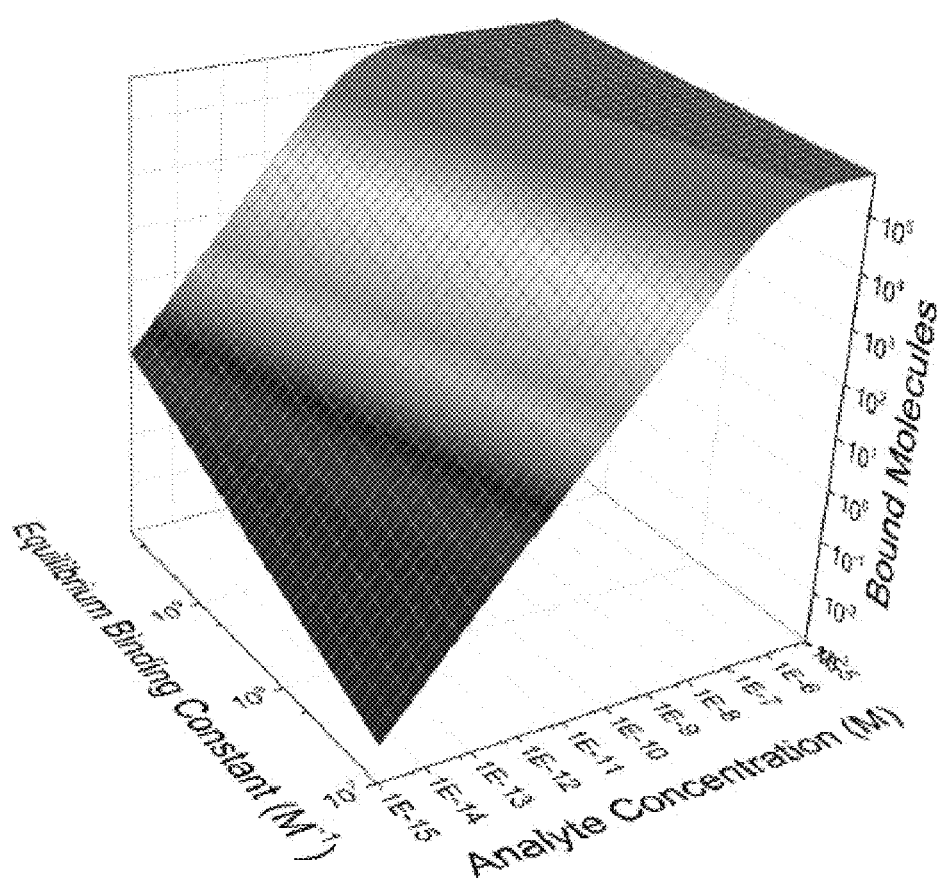
FIG. 1 depicts a graph for the solution of calculations based on the Langmuir Binding Isotherm (Equation 1) which demonstrates the profound effect of capture agent affinity and analyte concentration on the number of molecules bound to a sensor surface. It is preferable to use high gain amplification strategies to measure in the fM concentration range due to the minimal number of binding events. Assumptions include a sensor surface area of 85 $\mu m^2$ and $6 \times 10^{11}$ capture agents/$cm^2$.

Embodiments of the methods, compositions, and systems provided herein relate to enzymatic enhancement of immunoassays using photonic sensor arrays. Some such embodiments provide highly sensitive assays to detect and/or measure target analytes in a sample. In some embodiments, a first capture probe is attached to an optical ring resonator; a target analyte selectively binds to the first capture probe; a second capture probe selectively binds the complex comprising the bound target analyte. In some embodiments, the second capture probe comprises a catalyst, such as an enzyme, such as horseradish peroxidase. In some embodiments, a catalyst selectively binds to the second capture probe through affinity tags. A reagent contacts the catalyst to form a precipitate. The precipitate is detected and measured by changes at the optical sensor. The use of two capture probes and a catalyst in the methods, compositions and systems provided herein greatly enhances any signal of a target analyte binding to the first capture probe.

Beyond bound tag-based amplification strategies, enzymatic precipitate deposition on the microrings represents another method for effectively amplifying the signal associated with analyte binding. Enzymatic reactions are commonly used in immunoassays, involving enzymes such as horseradish peroxidase (HRP),[1,2] alkaline phosphatase,[3] or β-galactosidase[4] to catalyze a chemical reaction that produces an optical (usually colorimetric or fluorescent) readout. These enzyme-linked immunosorbent assays (ELISAs), which have been in use for over 30 years,[5] have been useful for protein detection. Many ELISAs have been used to validate protein assays developed herein, with a multitude of commercial products consistently demonstrating limits of detection in the pg/mL range.[6,7] Enzymatic enhancement strategies are also highly amenable to nucleic acid analyses and the detection of any species to which the recognition of an enzymatically active moiety can be facilitated.

Though the ELISA offers excellent sensitivity and highly useful microwell plate compatibility, the assay has many drawbacks. Traditional ELISAs are labor-intensive, with multiple washing steps and seemingly endless pipetting, and this process is time-consuming (2-4 h). Additionally, traditional ELISAs are not a multiplexed technique: for each analyte, a different microplate must be used. Though progress has been made toward creating "mix-and-match" microwell strips that can be assembled into an array of microwells specific for different protein targets, each analyte requires cumbersome and space-consuming independent calibration wells. Even in the multiplexed ELISA format, a single sample must be divided into multiple ELISA microwells and tested separately for each analyte. Thus, ELISAs are fundamentally limited in multiplexing capabilities by the sample volume (~100 uL per well), the number of wells that a researcher is willing to employ for a single study, and the logistics of conducting multiple independent ELISAs and separate calibrations in parallel. These limitations can be overcome, while still maintaining pg/mL sensitivity, by combining microring resonators with enzymatic amplification.

While the use of enzymatic amplification on microring resonators introduces complexity it can substantially improve the limit of detection. Instead of using an enzymatic process to introduce a colorimetric or fluorescent signal, the assay can be used to produce an insoluble precipitate that substantially alters the effective refractive index (RI) at the ring surface. With an enzyme-amplified sandwich assay, cytokine concentrations that were previously unable to be detected can be observed with ease.

In this disclosure, progress toward the optimization of an HRP-catalyzed amplification scheme is presented. This enzymatic process is applied to analytes including interleukin-2 (IL-2) and interleukin-6 (IL-6) detection. Two-step cytokine sandwich assays typically have limits of detection on the order of 10 pM[9] (and previous bead-based assays on the same platform were capable to detect 200 fM protein),[10] the HRP amplification assay achieves detection of IL-2 down to 67 fM (1 pg/mL). Importantly, the enzymatic process can display a lower and more reproducible background than other bead-based assays, also removing the need for time-consuming bead exchange directly before running the assay.[10] The ability to quantitate cytokines in the 1-100 pg/mL range is vital for a range of challenging protein biosensing applications, including serum and cerebrospinal fluid (CSF) diagnostics. Additionally, previously lowestachievable cytokine detection limits (100 pg/mL-1 ng/mL) on the platform, which were barely observable (<1 pm shift) with other microring resonator sandwich assays, now produce large nm-scale wavelength shifts with enzymatic amplification.

For enhancement strategies, desirable characteristics include high signal gain, cross-platform modularity, and a resistance to matrix effects. Previous demonstrations of signal enhancement strategies have included enzymatic, nucleic acid, electrochemical, and particle-based labels (Munge, B. S.; Coffey, A. L.; Doucette, J. M.; Somba, B. K.; Malhotra, R.; Patel, V.; Gutkind, J. S.; Rusling, J. F. Angew. Chem., Int. Ed. 2011, 50, 7915-7918; Konry, T.; Hayman, R. B.; Walt, D. R. Anal. Chem. 2009, 81, 5777-5782; Ivanov, I.; Stojcic, J.; Stanimirovic, A.; Sargent, E.; Nam, R. K.; Kelley, S. O. Anal. Chem. 2013, 85, 398-403; (8) Luchansky, M. S.; Washburn, A. L.; McClellan, M. S.; Bailey, R. C. Lab Chip 2011, 11, 2042-2044; Krishnan, S.; Mani, V.; Wasalathanthri, D.; Kumar, C. V.; Rusling, J. F. Angew. Chem., Int. Ed. 2011, 50, 1175-1178). Enzymatic-based methods are particularly attractive due to the high gain possible from multiple turnovers. Horseradish peroxidase (HRP) has found usage in bioanalytical methods on account of its high substrate turnover (400 s$^{-1}$) and extended stability, which offers extremely high theoretical signal amplification ($10^7$) (Veitch, N. C. Phytochemistry 2004, 65, 249-259; Azevedo, A. M.; Prazeres, D. M. F.; Cabral, J. M. S.; Fonseca, L. P. J. Mol. Catal. B: Enzym. 2001, 15, 147-153; Gorris, H. H.; Walt, D. R. J. Am. Chem. Soc. 2009, 131, 6277-6282). Furthermore, numerous HRP-conjugates of useful biomolecular reagents are available commercially.

In this disclosure, an approach is described using a silicon photonic microring resonator detection platform, in which an HRP signal enhancement step is used to robustly provide limits of detection at or below 1 pg/mL, using three cytokines as representative biomolecular targets. The enzymatic enhancement strategy described herein offers superior limits of detection while also featuring the potential for broad applicability across multiple analyte types on account of its modular nature.

To showcase the pairing of microring resonators with this signal enhancement approach, the levels of three interleukins were quantitated in both buffered solutions as well as undiluted cerebrospinal fluid. Interleukins are signaling cytokines that play a key role in regulating immune response but have also been implicated in the development and progression of numerous diseases including Alzheimer's, dementia, and cancer. They are challenging analytes due to their naturally low abundance, and undiluted CSF represents a complex and clinically relevant matrix for robust assay validation (Sokolova, A.; Hill, M. D.; Rahimi, F.; Warden, L. A.; Halliday, G; M.; Shepherd, C. E. Brain Pathol. 2009, 19, 392-398; Llano, D. A.; Li, J. H.; Waring, J. F.; Ellis, T.; Devanarayan, V.; Witte, D. G.; Lenz, R. A. Alzheimer Dis. Assoc. Disord. 2012, 26, 322-328; Angelopoulos, P.; Agouridaki, H.; Vaiopoulos, H.; Siskou, E.; Doutsou, K.; Costa, V.; Baloyiannis, S. I. Int. J. Neurosci. 2008, 118, 1659-1672; Allen, C.; Duffy, S.; Teknos, T.; Islam, M.; Chen, Z.; Albert, P. S.; Wolf, G.; Van Wales, C. Clin. Cancer Res. 2007, 13, 3182-3190; Anderson, N. L.; Anderson, N. G. Mol. Cell. Proteomics 2002, 1, 845-867). While enzyme-linked immunosorbent assays (ELISAs) are a method for interleukin quantitation, the labor intensive nature and limited multiplexing capacity of ELISA have motivated the development of alternative approaches (Palandra, J.; Finelli, A.; Zhu, M.; Masferrer, J.; Neubert, H. Anal. Chem. 2013, 85, 5522-5529; Luchansky, M. S.; Bailey, R. C. J. Am. Chem. Soc. 2011, 133, 20500-20506). Combined with a horseradish peroxidase enzymatic signal enhancement strategy, we demonstrate that silicon photonic microring resonators can robustly quantitate biomarker concentrations in a relatively rapid and multiplexed assay format with limits of detection at or below 1 pg/mL.

Sensor chip design and scanning instrumentation (Maverick detection platform from Genalyte, Inc.) and their use in the quantitation of a range of biomolecular targets, including proteins have been described (Washburn, A. L.; Gunn, L. C.; Bailey, R. C. Anal. Chem. 2009, 81, 9499-9506; Iqbal, M.; Gleeson, M. A.; Spaugh, B.; Tybor, F.; Gunn, W. G.; Hochberg, M.; Baehr-Jones, T.; Bailey, R. C.; Gunn, L. C. IEEE J. Sel. Top. Quantum Electron. 2010, 16, 654-661). Some embodiments of the methods, compositions and systems provided herein include the use of silicon photonic resonators. In an example of a silicon photonic resonator, a sensor chip includes 32 microring sensor elements that include 24 active microrings and 8 thermal controls. Microfluidic gaskets are used to spatially functionalize chips with up to four different analyte-specific capture antibodies. Target analytes are captured from the samples of interest as they are flowed across the sensor surface, and responses are enhanced with biomolecular specifically through subsequent recognition with secondary antibodies and tertiary reagents. All of these binding responses are measured by recording the shifts in resonance wavelengths supported by the microring sensor elements, which are sensitive to the local refractive index sampled by the circulating optical mode.

Silicon photonic resonators confine discrete frequencies of light via total internal reflection, and achieve constructive interference when light circumnavigates the structure an integer multiple of its wavelength, as shown in Equation 2, where m is a non-zero integer, r is the microring radius and $n_{eff}$ is the effective refractive index sampled by the optical mode.

$$m\lambda = 2\pi r n_{eff} \qquad [2]$$

Boundary conditions of this propagating light dictate a non-zero electric field at the reflecting boundary, resulting in an evanescent field extending into the local environment of the sensor. Interactions between this evanescent field and the local environment modulate the resonant wavelength of the structure, which is monitored with sub-picometer precision by the optical scanning instrumentation. Biomolecule binding events result in the displacement of water (refractive index ~1.33) with biomolecules of a higher refractive index (~1.5), resulting in a positive shift in the resonant wavelength. A tunable external cavity diode laser centered at 1550 nm is coupled into the sensor via microring-specific grating couplers, and scanned across an appropriate spectral window to determine transmission dips associated with resonant coupling. Sensor array elements are sequentially probed by rastering the laser across the substrate with each individual element being interrogated approximately every 8 seconds, which is sufficient to directly observe the kinetics of biomolecular binding.

As refractive index responsive devices, microring resonators can function as labelfree biochemical sensors. During the assay development process described herein, it was determined that sensor response was further enhanced when using two secondary detection antibodies. In some embodiments, two detection antibodies were used for a target analyte. The secondary capture agent also provides an opportunity for tertiary-enhancement reagents to be included to achieve even larger per-analyte responses.

Optical Sensors

Some embodiments of the methods, compositions and systems provided herein include an optical sensor. Examples of optical sensors are provided in U.S. Pub. No. 2013/0295688 which is incorporated herein by reference in its entirety. In some embodiments, optical sensors include silicon photonic microring resonators which can have high spectral sensitivity towards surface binding events between a target analyte and an optical sensor modified with a capture probe that can selectively bind to the target analyte. The systems of several embodiments are based on refractive index-based sensing schemes in which the mass of bound analytes, potentially in combination with other factors such as capture probe affinity and surface density, contributes to the observed signal and measurement sensitivity.

In some embodiments, analyte detection can be accomplished using an optically based system that includes a light source, an optical sensor, and an optical detector. In various embodiments, the light source outputs a range of wavelengths. For example, the light source may be a relatively narrow-band light source that outputs light having a narrow bandwidth wherein the wavelength of the light source is swept over a region many times the bandwidth of the light source. This light source may, for example, be a laser. This laser may be a tunable laser such that the wavelength of the laser output is varied. In some embodiments the laser is a diode laser having an external cavity. This laser need not be limited to any particular kind and may, for example, be a fiber laser, a solid state laser, a semiconductor laser or other type of laser or laser system. The laser itself may have a wavelength that is adjustable and that can be scanned or swept. Alternatively, additional optical components can be used to provide different wavelengths. In some embodiments, the light source outputs light having a wavelength for which the waveguide structure is sufficiently optically transmissive. In some embodiments, the waveguide structure is within a sample medium such as an aqueous medium and the light source outputs light having a wavelength for which the medium is substantially optically transmissive such that resonance can be reached in the optical resonator. Additionally, in some embodiments, the light source output has a wavelength in a range where the analyte (e.g., molecules) of interest do not have a non-linear refractive index. Likewise, in various embodiments, the light source may be a coherent light source that outputs light having a relatively long coherence length. However, in various embodiments, the light source may be a coherent light source that outputs light having a short coherence length. For example, in certain embodiments, a broadband light source such as a super-luminescent light emitting diode (SLED) may be used. In such cases, the wavelength need not be swept. An erbium amplifier running broadband that produces light having a range of wavelengths all at once may also be used. Light from the broadband source extending over an extended spectral range may be injected into the waveguide input. A spectral analyzer (e.g., comprising a spectrometer) may be employed to collect light from the waveguide output and analyze the output spectrum.

The light source provides light to the optical sensor. The light source may be controlled by control electronics. These electronics may, for example, control the wavelength of the light source, and in particular, cause the light source to sweep the wavelength of the optical output thereof. In some embodiments, a portion of the light emitted from the light source is sampled to determine, for example, the emission wavelength of the light source.

In some embodiments, the optical sensor comprises a transducer that alters the optical output based on the presence and/or concentration of the analyte to be detected. The optical sensor may be a waveguide structure. The optical sensor may be an integrated optical device and may be included on a chip. The optical sensor may comprise semiconductor material such as silicon. The optical sensor may be an interferometric structure (e.g., an interferometer) and produce an output signal as a result of optical interference. The optical sensor 104 may be included in an array of optical sensors.

The optical detector detects the optical output of the sensor. In various embodiments, the optical detector comprises a transducer that converts an optical input into an electrical output. This electrical output may be processed by processing electronics to analyze the output of the sensor. The optical detector may comprise a photodiode detector. Other types of detectors may be employed. Collection optics in an optical path between the sensor and the detector may facilitate collection of the optical output of the sensor and direct this output to the detector. Additional optics such as mirrors, beam-splitters, or other components may also be included in the optical path from the sensor to the detector.

In various embodiments, the optical sensor is disposed on a chip while the light source and/or the optical detector are separate from the chip. The light source and optical detector may, for example, be part of an apparatus comprising free space optics that interrogates the optical sensors on the chip.

In various embodiments, a solution such as an analyte solution is flowed past the optical sensor. The detector detects modulation in an optical signal from the optical sensor when an analyte of interest is detected.

Ring resonators offer highly sensitive optical sensors that can be prepared so as to detect analytes. The operation of a ring resonator is shown in connection with FIG. 2. In this configuration, the optical sensor comprises an input/output waveguide 202 having an input 204 and an output 206 and a ring resonator 208 disposed in proximity to a portion of the input/output waveguide 202 that is arranged between the input 204 and the output 206. The close proximity facilitates optical coupling between the input/output waveguide 202 and the ring resonator 208, which is also a waveguide. In this example, the input/output waveguide 202 is linear and the ring resonator 208 is circular such that light propagating in the input/output waveguide 202 from the input 204 to the output 206 is coupled into the ring resonator 208 and circulates therein. Other shapes for the input/output waveguide 202 (for example, curved) and ring resonator 208 (e.g., oval, elliptical, triangular, etc.) are also possible.

Figure 2:
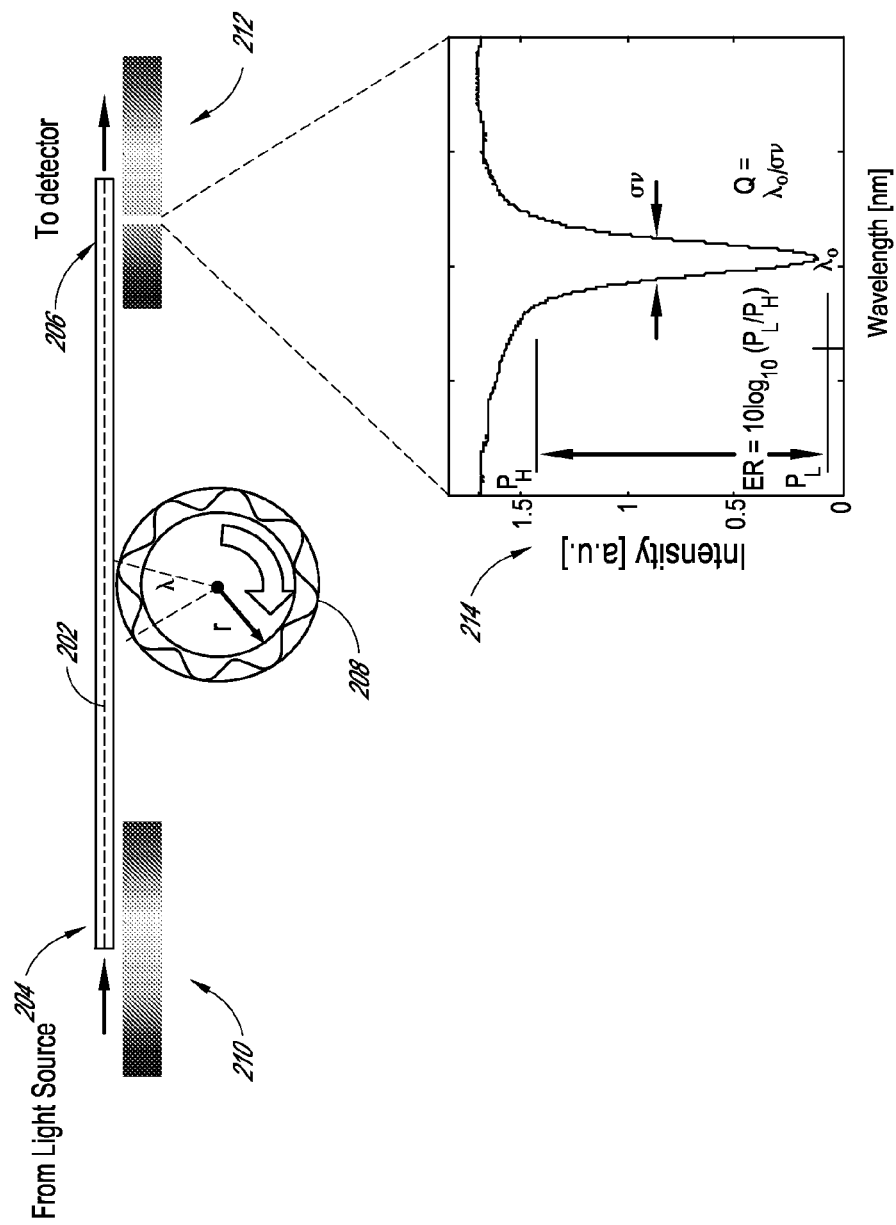
FIG. 2 shows a schematic diagram of an optical sensor comprising a waveguide and a ring resonator.

FIG. 2 shows an input spectrum 210 to represent that the light injected into the waveguide input 204 includes a range of wavelengths, for example, from a narrow band light source having a narrow band peak that is swept over time (or from a broadband light source such as a super-luminescent diode). Similarly, an output spectrum 212 is shown at the waveguide output 206. A portion of this output spectrum 212 is expanded into a plot of intensity versus wavelength 214 and shows a dip or notch in the spectral distribution at the resonance wavelength, $\lambda_0$, of the ring resonator 208.

Without subscribing to any particular scientific theory, light "resonates" in the ring resonator when the number of wavelengths around the ring (e.g. circumference) is exactly an integer. In this example, for instance, at particular wavelengths, light circulating in the ring resonator 208 is at an optical resonance when:

$$m\lambda = 2\pi r \, n$$

where m is an integer, λ is the wavelength of light, r is the ring radius, and n is the refractive index.

In this resonance condition, light circulating in the ring interferes with light propagating within the linear waveguide 202 such that optical intensity at the waveguide output 206 is reduced. Accordingly, this resonance will be measured as an attenuation in the light intensity transmitted down the linear waveguide 202 past the ring resonator 208 as the wavelength is swept by the light source in a manner such as shown in the plot 214 of FIG. 2.

Notably, the plot 214 in FIG. 2 shows the dip or notch having a width, δυ as measured at full width half maximum (FWHM) and an associated cavity Q or quality factor, $Q=\lambda_0/\delta\upsilon$. The ring resonator 208 produces a relatively high cavity Q and associated extinction ratio (ER) that causes the optical sensor 104 to have a heightened sensitivity.

Figure 3:
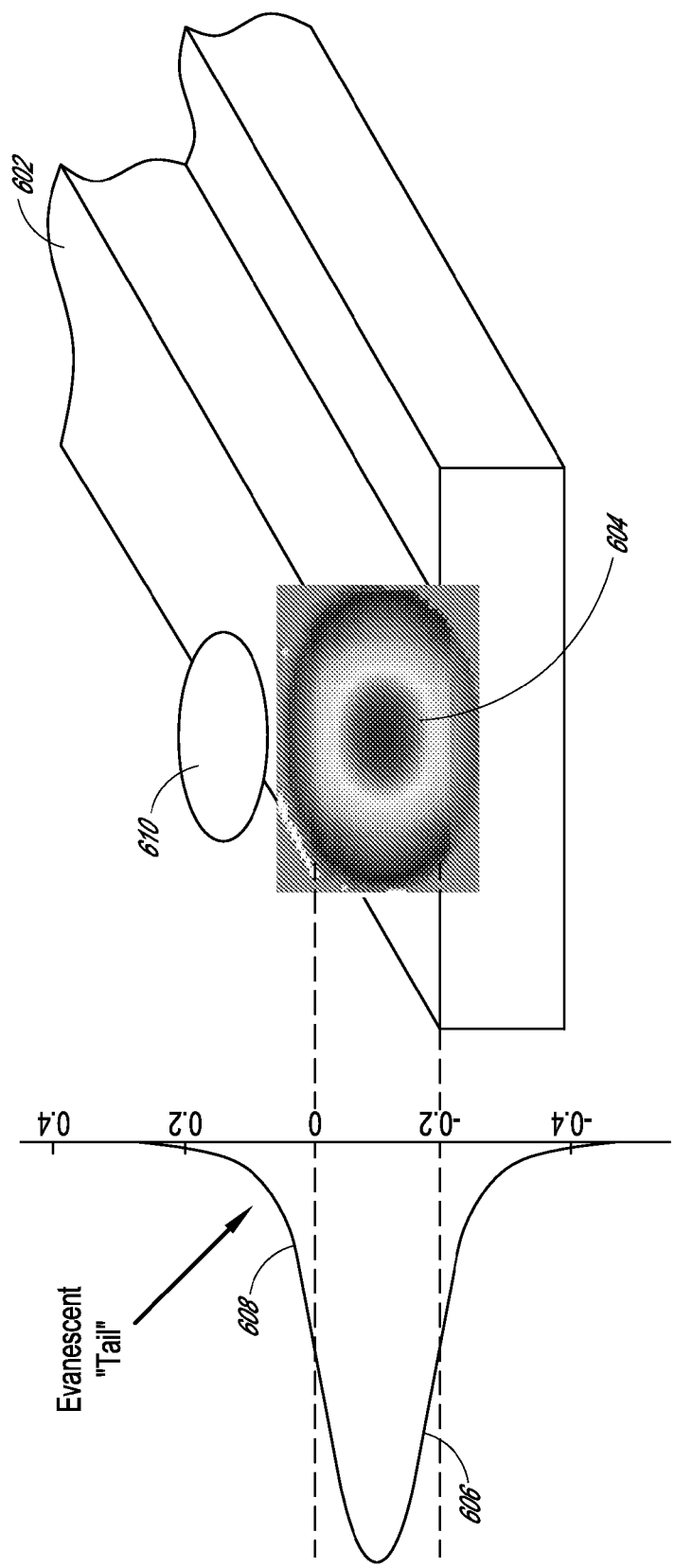
FIG. 3 is a cut-away view of a waveguide schematically showing an intensity distribution having an evanescent tail extending outside the waveguide where an element such as a molecule or particle may be located so as to affect the index of refraction of the waveguide.

As is well known, light propagates within waveguides via total internal reflection. The waveguide supports modes that yield a spatially varying intensity pattern across the waveguide. A cross-section of a waveguide 602 shown in FIG. 3 illustrates an example intensity distribution 604. A plot 606 of the intensity distribution at different heights is provided adjacent the waveguide structure 602. As illustrated, a portion 608 of the electric field and optical energy referred to as the evanescent "tail" lies outside the bounds of the waveguide 602. The length of this field 608, as measured from the 1/e point, is between 50 and 150 nm, e.g. about 100 nm in some cases. An object 610 located close to the waveguide 602, for example, within this evanescent field length affects the waveguide. In particular, objects 610 within this close proximity to the waveguide 602 affect the index of refraction of the waveguide. The index of refraction, n, can thus be different when such an object 610 is closely adhered to the waveguide 602 or not. In various embodiments, for example, the presence of an object 610 increases the refractive index of the waveguide 602. In this manner, the optical sensor may be perturbed by the presence of an object 610 in the vicinity of the waveguide structure 602 thereby enabling detection. In various embodiments, the size of the object is about the length (e.g. 1/e distance) of the evanescent field to enhance interaction therebetween.

In the case of the ring resonator, an increase in the refractive index, n, increases the optical path length traveled by light circulating about the ring. Longer wavelengths can resonate in the resonator and, hence, the resonance frequency is shifted to a lower frequency. The shift in the resonant wavelengths of the resonator can therefore be monitored to determine if an object 610 has located itself within close proximity to the optical sensor (e.g., the ring resonator and/or a region of the linear waveguide closest to the ring resonator). A binding event, wherein an object 610 binds to the surface of the optical sensor can thus be detected by obtaining the spectral output from the waveguide output and identifying dips in intensity (or peaks in attenuation) therein and the shift of these dips in intensity.

In various embodiments, the waveguide 602, e.g., the linear waveguide and/or the ring resonator comprise silicon. In some embodiments, the surface of the waveguide 602 may be natively passivated with silicon dioxide. As a result, standard siloxane chemistry may be an effective method for introducing various reactive moieties to the waveguide 602, which are then subsequently used to covalently immobilize biomolecules via a range of standard bioconjugate reactions.

Moreover, the linear waveguide, ring resonator, and/or additional on-chip optics may be easily fabricated on relatively cheap silicon-on-insulator (SOI) wafers using well established semiconductor fabrication methods, which are extremely scalable, cost effective, and highly reproducible. Additionally, these devices may be easily fabricated and complications due to vibration are reduced when compared to "freestanding" cavities. In one example embodiment, 8" SOI wafers may each contain about 40,000 individually addressable ring resonators. One advantage of using silicon-based technology is that various embodiments may operate in the Si transparency window of around 1.55 µm, a common optical telecommunications wavelength, meaning that lasers and detectors are readily available in the commercial marketplace as plug-and-play components.

Some embodiments of the waveguides useful with the methods, systems and compositions provided herein include strip and rib waveguides. Other types of waveguides, such as for example, strip-loaded waveguides can also be used. Lower cladding lies beneath the waveguides. In some embodiments, the waveguides are formed from a silicon-on-insulator chip, wherein the silicon is patterned to form the waveguides and the insulator beneath provides the lower cladding. In many of these embodiments, the silicon-on-insulator chip further includes a silicon substrate. Details on the fabrication of silicon biosensor chips can be found in Washburn, A. L., L. C. Gunn, and R. C. Bailey, Analytical Chemistry, 2009, 81(22): p. 9499-9506, and in Bailey, R. C., Washburn, A. L., Qavi, A. J., Iqbal, M., Gleeson, M., Tybor, F., Gunn, L. C. Proceedings of SPIE—The International Society for Optical Engineering, 2009, the disclosures of which are hereby incorporated by reference in their entirety.

Still other designs than those specifically shown in the drawings herein may be employed. More ring resonators may be added. The resonators may also have different sizes and/or shapes. Additionally, the ring resonator(s) may be positioned differently with respect to each other as well as with respect to the input/output waveguide. Likewise, more non-ring resonator waveguides may be added.

In various embodiments, for example, a drop configuration is used. For example, in some such embodiments, a ring resonator is disposed between first and second waveguides. Light (such as a wavelength component) may be directed into an input of the first waveguide and depending on the state of the ring resonator, may be directed to either an output of the first waveguide or an output of the second waveguide. For example, for resonant wavelengths, the light may be output from the second waveguide instead of the first waveguide. An optical detector may thus monitor shifts in intensity peaks to determine the presence of an analyte of interest detected by the optical sensor in some such embodiments.

Combinations of these different features are also possible. Moreover, multiple resonators and/or waveguides may be placed in any desired geometric arrangement. Additionally, spacing between resonators and/or waveguides may be varied as desired. Different features can be combined in different ways.

Also, although linear waveguides are shown in FIGS. 2 and 3 as providing access to the ring resonators, these waveguides need not be restricted to plain linear geometry. In some examples, for instance, these waveguides may be curved or otherwise shaped differently. Likewise the ring resonators need not be circularly shaped but can have other shapes. The ring resonators may be oval or elliptically-shaped, triangularly-shaped or irregularly shaped.

Other geometries may possibly be used for the resonator, such as, for example, microsphere, microdisk, and microtoroid structures. See, e.g., Vahala, Nature 2003, 424, 839-846; and in Vollmer & Arnold, Nature Methods 2008, 5, 591-596, the disclosures of which are hereby incorporated by reference in their entirety. Again, combinations of these different features are also possible and different features can be combined in different ways.

Additional details regarding sensors and apparatus for interrogating such sensors are included in U.S. Patent Publication 2011/0045472 titled "Monitoring Enzymatic Process" as well as PCT Publication WO 2010/062627 titled "Biosensors Based on Optical Probing and Sensing", which are each incorporated herein by reference in its entirety.

Target Analytes

Some embodiments of the methods, compositions and systems provided herein include a target analyte. As used herein a 'target analyte' can include a substance to be detected in a test sample. In some embodiments, a target analyte can include a nucleic acid, protein, and a carbohydrate. As used herein, a 'protein' can include a polypeptide, a peptide, hormones, enzyme, antibodies and fragments thereof. In some embodiments, a target analyte is an antigen that selectively binds to an antibody or antigen-binding fragment thereof. In some embodiments, a target analyte includes a cytokine. Examples of cytokines include chemokines, interferons, interleukins, lymphokines, and tumour necrosis factor. In some embodiments, cytokines include IL-2, IL-6, and IL-8.

In some embodiments, the target analyte is associated with a disorder such as brain trauma, stroke, multiple sclerosis, post-traumatic stress disorder, assorted infections of the central nervous system, and Alzheimer's disease.

Test Samples

Some embodiments of the methods, compositions and systems provided herein include a test sample. In some embodiments, a test sample includes a target analyte. In some embodiments, a test sample comprises a biological sample. Examples of biological samples include any biological tissue or fluid derived from a subject such as sputum, cerebrospinal fluid, blood, blood fractions such as serum and plasma, blood cells, tissue, biopsy samples, urine, peritoneal fluid, pleural fluid, amniotic fluid, vaginal swab, skin, lymph fluid, synovial fluid, feces, tears, organs, or tumors. In some embodiments, a biological sample can include viral particles or fragments thereof, recombinant cells, cell components, cells grown in vitro, and cell culture constituents including, for example, conditioned medium resulting from the growth of cells in cell culture medium.

Capture Probes

Some embodiments of the methods, compositions and systems provided herein include a capture probe. A capture probe selectively binds to a target analyte. In some embodiments, a capture probe can selectively bind to a complex comprising a target analyte and another capture probe. In some embodiments, a capture probe can selectively bind to a target analyte bound to another capture probe. In some embodiments, a capture probe is attached to an optical sensor. Examples of capture probes include antibodies and antigen-binding fragments thereof; polypeptides; nucleic acids; and lectins.

As used herein "antibody" can include synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv including bi-specific sdFvs), and anti-idio-typic (anti-Id) antibodies, and epitope-binding fragments of any of the above. In some embodiments, an antibody or antigen-binding fragment thereof can be monospecific, bispecific, trispecific or of greater multispecificity. Multi-specific antibodies may be specific for different epitopes of a polypeptide or may be specific for both a polypeptide as well as for a heterologous epitope, such as a heterologous polypeptide or solid support material. See, e.g., PCT publications WO 93/17715; WO 92/08802; WO91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992); each of which is incorporated herein by reference in its entirety.

In some embodiments, a capture probe can include a polypeptide, which is inclusive of known polypeptide analogs. Examples of polypeptide analogs include molecules that comprise a non-naturally occurring amino acid, side chain modification, backbone modification, N-terminal modification, and/or C-terminal modification known in the art. For example, a polypeptide capture probe can comprise a D-amino acid, a non-naturally occurring L-amino acid, such as L-(1-naphthyl)-alanine, L-(2-naphthyl)-alanine, L-cyclohexylalanine, and/or L-2-aminoisobutyric acid. In some embodiments, a polypeptide capture probe can comprise an antigen to which an antibody target analyte is capable of binding. In various aspects, a capture probe can comprise a polypeptide antigen capable of binding to an antibody of interest that is a known biomarker for a particular disease or condition. It will be appreciated that a capture probe of the systems provided herein can comprise any antigen associated with any disease or condition for which a subject's antibody against the antigen is considered a biomarker. As a non-limiting example, a capture probe can comprise a viral antigen capable of binding to an antibody specific against the viral antigen. Presence of such an antibody, as detected by the systems provided herein, would indicate that the subject has been infected by the virus and mounted a specific immune response to it. In certain embodiments, a capture probe can comprise an auto-antigen associated with an autoimmune disorder or an antigen associated with an allergy, which capture probe is capable of binding to an antibody, such as an auto-antibody, of interest. Presence of such an antibody, as detected by the systems provided herein, would indicate that the subject has or is at risk of having the associated autoimmune disorder or allergy.

In some embodiments, a capture probe can include a nucleic acid. As used herein with respect to capture probes, "nucleic acid" refers to deoxyribonucleic acid (DNA) or ribonucleic acid (RNA) and known analogs, derivatives, or mimetics thereof. A nucleic acid capture probe can be oligomeric and include oligonucleotides, oligonucleosides, oligonucleotide analogs, oligonucleotide mimetics and chimeric combinations of these. A nucleic acid capture probe can be single-stranded, double-stranded, circular, branched, or hairpin and can contain structural elements such as internal or terminal bulges or loops. In some embodiments, a nucleic acid capture probe can have a length of at least, or at least about 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleobases, or the nucleic acid capture probe can have a length within any range bounded by two of the above-mentioned lengths.

In several embodiments, a nucleic acid capture probe and a target analyte comprising a nucleic acid bind to form a duplex. Such binding may occur through hybridization. As used herein, "hybridization" means the pairing of complementary strands of a nucleic acid capture probe and a nucleic acid analyte of interest. In some embodiments, a nucleic acid capture probe and nucleic acid molecule of interest can hybridize under "stringent conditions," which refer to conditions under which a nucleic acid capture probe will hybridize to a nucleic acid molecule of interest, but to a minimal number of other sequences. A person of ordinary skill in the art will appreciate that stringent conditions are sequence-dependent and will vary in different circumstances. High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C. "Complementarity," as used herein, refers to the capacity for precise pairing between two nucleobases of a nucleic acid capture probe and nucleic acid analyte of interest. For example, if a nucleobase at a certain position of a capture probe is capable of hydrogen bonding with a nucleobase at a certain position of a nucleic acid analyte of interest, then the position of hydrogen bonding between the capture probe and the nucleic acid analyte of interest is considered to be a complementary position. The capture probe and the analyte of interest are complementary to each other when a sufficient number of complementary positions in each molecule are occupied by nucleobases which can hydrogen bond with each other. Thus, in some embodiments a nucleic acid capture probe and nucleic acid analyte of interest are specifically hybridizable and complementary, which indicate a sufficient degree of precise pairing or complementarity over a sufficient number of nucleobases such that stable and specific binding occurs. It will be appreciated that the sequence of a nucleic acid capture probe need not be 100% complementary to that of a nucleic acid analyte of interest to be specifically hybridizable. Moreover, a nucleic acid capture probe may hybridize over one or more segments such that intervening or adjacent segments are not involved in the hybridization event (e.g., a loop structure, mismatch or hairpin structure).

In several embodiments, a nucleic acid capture probe can comprise one or more oligonucleotide mimetics. The term "mimetic" includes oligomeric nucleic acids wherein the furanose ring or the furanose ring and the internucleotide linkage are replaced with non-naturally occurring groups. In certain embodiments, a nucleic acid capture probe comprises a peptide nucleic acid (PNA) oligonucleotide mimetic (Nielsen et al., *Science,* 1991, 254, 1497-1500). PNAs have favorable hybridization properties, high biological stability and are electrostatically neutral molecules. Representative United States Patents that teach the preparation of PNA oligomeric compounds include U.S. Pat. Nos. 5,539,082; 5,714,331 and 5,719,262. PNA compounds can be obtained commercially from Applied Biosystems (Foster City, Calif., USA). In some embodiments, capture probes comprising nucleic acids can include an oligonucleotide mimetic such as a linked morpholino units (morpholino nucleic acid) having heterocyclic bases attached to the morpholino ring (Dwaine A. Braasch and David R. Corey, *Biochemistry,* 2002, 41(14), 4503-4510). In some embodiments, capture probes comprising nucleic acids can include an oligonucleotide mimetic such as a cyclohexene nucleic acids (CeNA) (Wang et al., *J. Am. Chem. Soc.,* 2000, 122, 8595-8602). In some embodiments, capture probes comprising nucleic acids can include a locked nucleic acid (LNA). An LNA capture probe includes nucleoside or nucleotide analogues that include at least one LNA monomer (e.g., an LNA nucleoside or LNA nucleotide). LNA monomers are described in, for example, WO 99/14226, U.S. Pat. No. 6,043,060, U.S. Pat. No. 6,268,490, WO 01/07455, WO 01/00641, WO 98/39352, WO 00/56746, WO 00/56748 and WO 00/66604. In several embodiments, a nucleic acid capture probe can include a non-native, degenerate, or universal base such as inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine, or the like. In some embodiments, a nucleic acid capture probe can include isocytosine and/or isoguanine in order to reduce non-specific hybridization as generally described in U.S. Pat. No. 5,681,702.

In several embodiments, a nucleic acid capture probe can comprise an "aptamer" to bind to a nucleic acid or polypeptide analyte of interest. Aptamers are described in U.S. Pat. Nos. 5,270,163; 5,475,096; 5,567,588; 5,595,877; 5,637,459; 5,683,867; and 5,705,337; which are herein incorporated by reference in their entireties. Aptamers can bind to various molecular targets such as small molecules, proteins, and nucleic acids.

In some embodiments, wherein the target analyte comprises a carbohydrate, suitable capture probes can include lectins. Lectins are proteins that bind to saccharides and differ in the types of carbohydrate structures they recognize. Several known lectins that can be used in capture probes of various embodiments include those that have been isolated from plants including *Conavalia ensiformis, Anguilla anguilla, Triticum vulgaris, Datura stramoniuim, Galanthus nivalis, Maackia amurensis, Arachis hypogaea, Sambucus nigra, Erythrina cristagalli, Lens culinaris, Glycine may, Phaseolus vulgaris, Allomyrina dichotoma, Dolichos biflorus, Lotus tetragonolobus, Ulex europaeus,* and *Ricinus communis.* Additional lectins that can be used in capture probes of several embodiments include any of the animal, bacterial, or fungal lectins known in the art. Several bacterial and fungal lectins have considerably high affinity (micromolar Kd) towards carbohydrates compared to plant or animal lectins.

Attachment of Capture Probes to Optical Sensors

In some embodiments, a capture probe is attached to an optical sensor. Methods of attaching a capture probe to a substrate comprising an optical sensor are described in U.S. Pub. No. 2013/0295688 which is incorporated herein by reference in its entirety. In some embodiments, the capture probes are attached to a surface of an optical sensor by a linkage, which may comprise any moiety, functionalization, or modification of the binding surface and/or capture probes that facilitates the attachment of the capture probes to the surface of the optical sensor. The linkage between the capture probes and the surface of the optical sensor can comprise one or more chemical bonds; one or more non-covalent chemical bonds such as Van der Waals forces, hydrogen bonding, electrostatic interaction, hydrophobic interaction, or hydrophilic interaction; and/or chemical linkers that provide such bonds.

Further Capture Probes

Some embodiments of the methods, compositions and systems provided herein include a second capture probe. In some embodiments, such capture probes selectively bind to a complex comprising a target analyte bound to another capture probe. The second capture probe can comprise any capture probe described herein. In some embodiments, the second capture probe comprises an antibody or antigen-binding fragment thereof. In some embodiments, the second capture probe comprises a detectable label. In some embodiments the detectable label comprises a catalyst, such as an enzyme.

Similar to a sandwich assay format in which an antigen is first bound by a substrate-immobilized primary capture agent and then recognized by a secondary capture agent, the systems of several embodiments provided herein comprise a capture probe (analogous to a sandwich assay primary capture agent) and an antibody (analogous to a sandwich assay secondary capture agent). It is possible to detect and/or measure binding-induced shifts in the resonance wavelength of individual binding events with the systems of various embodiments, including binding of an antibody to the optical sensor. Without being bound by theory, binding of an antibody to the optical sensor can induce a change in local refractive index, thereby inducing a detectable and/or measurable shift in the resonance wavelength on the optical sensor.

In several embodiments, a system for detecting and/or measuring an analyte of interest includes an antibody capable of binding to the analyte of interest or a complex or duplex formed between a capture probe attached to a surface of an optical sensor and the analyte of interest. It will be understood that in several embodiments the antibody capable of binding to a complex or duplex formed between a capture probe and analyte of interest can bind to a portion of the analyte of interest that is not bound to the capture probe in formation of the complex or duplex such that the antibody does not directly bind and/or physically contact the capture probe. Thus, the binding of a capture probe/analyte complex by the antibody can be accomplished by the antibody contacting and binding only the analyte portion of the capture probe/analyte complex. In various aspects, an antibody can bind to an epitope on an analyte of interest distinct from the epitope or binding site on the analyte of interest involved in binding to the capture probe. In some aspects, the antibody capable of binding to a complex or duplex formed between a capture probe and analyte of interest binds to the analyte of interest without inhibiting or interfering with the binding between the analyte of interest and the capture probe.

An example of a binding event that increases the refractive index at the optical sensor surface and can be observed as an increase in the resonance wavelength of the optical sensor is an antibody-analyte complex binding to a capture probe attached to a surface of an optical sensor (a "primary" binding event). Yet another detectable and/or measurable binding event is an antibody binding to an analyte of interest which is already bound to a capture probe attached to a surface of an optical sensor (a "secondary" binding event). A further detectable and/or measurable binding event is an antibody binding to a duplex or complex formed between an analyte of interest and a capture probe attached to a surface of an optical sensor (a "secondary" binding event).

It will be understood by a person of ordinary skill in the art that in several aspects, an antibody can bind to the analyte of interest either prior to or after binding between the analyte of interest and capture probe. Thus, in some embodiments a binding-induced shift in the resonance wavelength can be detected and/or measured for (1) an antibody-analyte complex binding to a capture probe attached to a surface on an optical sensor, (2) an antibody binding to the analyte already bound to the capture probe attached to a surface on an optical sensor, or (3) an antibody binding to the duplex or complex formed between the analyte and capture probe attached to a surface on an optical sensor. It will also be apparent to a person of ordinary skill in the art that in some aspects, an antibody is not capable of binding to the capture probe alone or analyte of interest alone, but is capable of binding to the complex or duplex formed between the capture probe and analyte of interest.

Accordingly, certain embodiments drawn to a system for detecting an analyte of interest includes both (1) a capture probe comprising an antibody attached to a surface of an optical sensor and (2) an antibody capable of binding to the analyte of interest either prior to or after binding between the analyte of interest and capture probe. In additional embodiments, a system for detecting an analyte of interest includes (1) a capture probe comprising a nucleic acid attached to a surface of an optical sensor wherein the capture probe is capable of binding to an analyte of interest, and (2) an antibody that is not capable of binding to the capture probe alone or analyte of interest alone, but is capable of binding to the complex or duplex formed between the capture probe and analyte of interest.

In certain embodiments, the system includes an antibody that specifically binds to an oligonucleotide duplex, such as a DNA:RNA duplex, DNA:DNA duplex, or RNA:RNA duplex, formed between a capture probe and analyte of interest, but does not bind to the nucleic acid capture probe or analyte of interest prior to their binding. As used herein, the term "duplex" refers to a double-stranded molecule, which can be formed by hybridization of single-stranded nucleic acids.

Anti-DNA:RNA antibodies can detect miRNA analytes of interest while significantly reducing assay complexity. Both monoclonal and polyclonal antibodies against RNA:RNA and DNA:RNA homoduplexes have been previously developed and utilized in hybridization based assays for the detection of numerous nucleic acid targets such as viral nucleic acids and *E. coli* small RNA. Casebolt, D. B. and C. B. Stephensen, Journal of Clinical Microbiology, 1992. 30(3): p. 608-12; Fliss, I., et al., Appl Microbiol Biotechnol, 1995. 43(4): p. 717-24; Lafer, E. M., et al., J Biol Chem, 1986. 261(14): p. 6438-43; Riley, R. L., D. J. Addis, and R. P. Taylor, J Immunol, 1980. 124(1): p. 1-7; Stollar, B. D., FASEB J, 1994. 8(3): p. 337-42 and Stollar, B. D. and A. Rashtchian, Anal Biochem, 1987. 161(2): p. 387-94; which are all incorporated by reference in their entireties.

In particular embodiments, a system for detecting an analyte of interest includes an antibody that specifically binds to a DNA:RNA duplex. One non-limiting example of such an antibody that can be used in several embodiments is that specifically binds to a DNA:RNA duplex is S9.6, a monoclonal antibody that specifically binds to RNA-DNA hybrids as described in Boguslawski et al., J. Immunological Methods, 89 (1986) 123-130, which is herein incorporated by reference in its entirety.

Particles

Some embodiments of the methods, compositions and systems provided herein include particles. While systems comprising an antibody configured in a sandwich assay format can detect and/or measure "primary" or "secondary" binding events, several embodiments are drawn to systems comprising a particle adapted to amplify a detectable and/or measurable optical property that is altered (e.g. resonance wavelength) upon a binding event on an optical sensor. Such embodiments are based on the present discovery that a "secondary" or "tertiary" binding event of particles to an optical sensor can increase the sensitivity of detection (i.e. lower the detection limit) by several-fold. For example, a particle can increase the sensitivity of detection from approximately the low pM to the high fM range, compared to a "secondary" binding event. In certain embodiments, systems can comprise a particle adapted to provide a "primary" binding event detectable signal. For example, a particle can be bound to an analyte of interest and a complex formed between them can then be bound to a capture probe attached to a surface of an optical sensor. In some embodiments, a particle can be bound to a second capture probe. Examples of particles are described in U.S. Pub. No. 2013/0295688 which is incorporated herein by reference in its entirety.

Several embodiments relate to a system for detecting an analyte of interest including a particle attached to an antibody, which is capable of specifically binding to the analyte or a duplex or complex formed between the analyte and capture probe, or capable of binding to the antibody. The particle is adapted to amplify a detectable and/or measurable optical property that is altered upon a binding event on an optical sensor. In one aspect, a particle can bind to an antibody that is already bound to an optical sensor, whether via binding to an analyte which is bound to a capture probe attached to a surface of the optical sensor or binding to a duplex or complex formed between the analyte of interest and a capture probe. Such a binding of the particle in this fashion can be considered a "tertiary" binding event, while the prior binding of the antibody to the optical sensor is a "secondary" binding event and the binding of the analyte of interest to the capture probe is a "primary" binding event.

In various embodiments, a particle can be associated with a molecule (e.g. by conjugation) that has affinity for the analyte of interest. For example, and not by limitation, a particle can be associated with a silane molecule having affinity to a polypeptide analyte of interest; a particle can be associated with a phosphate-containing molecule having affinity to a nucleic acid analyte of interest; a particle can be associated with a salt having affinity to a carbohydrate analyte of interest; or a particle can be associated with a organic molecule having affinity to a lipid.

It will be understood that in several aspects, a particle can be associated with a molecule that has affinity for the analyte of interest in the same way that capture probes described above can bind to an analyte of interest. For example, the analyte of interest and molecule associated with a particle can represent a binding pair, which can include but is not limited to antibody/antigen (nucleic acid or polypeptide), receptor/ligand, polypeptide/nucleic acid, nucleic acid/nucleic acid, enzyme/substrate, carbohydrate/lectin, or polypeptide/polypeptide. In some embodiments, a particle comprises a catalyst, such as an enzyme, such as horseradish peroxidase. It will also be understood that binding pairs of analytes of interest and molecules associated with particles described above can be reversed in several embodiments. Any of the functional groups and linkers described above with respect to attaching capture probes to an optical sensor surface can be used to conjugate particles to molecules that have affinity to an analyte of interest. In certain embodiments, an antibody can be conjugated to a particle, such as a COOH-functionalized polystyrene bead, via a n-hydroxy-succinimide ester (NHS) linkage, a DNA molecule can be conjugated to a particle, such as a streptavidin coated glass microsphere via biotin-streptavidin binding, a carbohydrate molecule can be conjugated to a particle, such as a gold nanoparticle, via a thiol linkage, a polypeptide molecule can be conjugated to a particle, such as a titanium dioxide nanoparticle, via an isocyanate silane linkage, and a polypeptide molecule can be conjugated to a particle, such as a magnetic nanoparticle or microsphere, via 1-ethyl-3-(3-dimethylaminopropyl)carbodiimide (EDC). It will also be understood that in various embodiments a molecule that has affinity for the analyte of interest can be associated with a particle by passive absorption.

It will be appreciated that a particle can comprise any material, shape, physical state, and/or size sufficient to amplify a detectable and/or measurable optical property that is altered upon a binding event on an optical sensor. Without being bound by theory, in some embodiments a particle comprises any material, shape, physical state, and/or size sufficient to increase the refractive index at the sensor surface, which can be observed as an increase in the resonance wavelength of the optical sensor. Any particle that has sufficient mass or other physical property, such as electron density, to increase the refractive index at the sensor surface can be used. In some embodiments, a particle can be amorphous or spherical, cubic, star-shaped, and the like. The particles provided herein can comprise solids, liquids, or gases. In several embodiments, a particle can comprise crystalline, polycrystalline, polymer, glass, biopolymer, or a composite of these materials.

In some embodiments, a particle adapted to amplify a detectable and/or measurable optical property that is altered upon a binding event on an optical sensor has a dimension along any axis, such as an average diameter, of at least about 0.1 nanometers (nm), 0.5 nm, 1 nm, 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 600 nm, 700 nm, 800 nm, 900 nm, 1,000 nm, 2,000 nm, 3,000 nm, 4,000 nm, 5,000 nm, greater than 5,000 nm, any number in between the aforementioned dimensions, or any range between two of the aforementioned dimensions. In several embodiments, a particle has a dimension along any axis, such as an average diameter, of about 1 nm to 1,000 nm. In several embodiments, a particle has a dimension along any axis, such as an average diameter, of about 50 nm to 200 nm.

In some embodiments, a particle comprises a polypeptide of at least 200 Daltons, (Da), 300 Da, 400 Da, 500 Da, 600 Da, 700 Da, 800 Da, 900 Da, 1 kilo Dalton (kDa), 5 kDa, 10 kDa, 15 kDa, 20 kDa, 25 kDa, 50 kDa, 75 kDa, 100 kDa, 200 kDa, 300 kDa, 400 kDa, 500 kDa, 600 kDa, 700 kDa, 800 kDa, 900 kDa, 1,000 kDa, 2,000 kDa, 3,000 kDa, 4,000 kDa, 5,000 kDa, 6,000 kDa, 7,000 kDa, 8,000 kDa, 9,000 kDa, 10,000 kDa, greater than 10,000 kDa, or any size or range between any two of the aforementioned sizes.

In some embodiments, a particle comprises any known polypeptide commonly used in molecular biology as recombinant expression or purification tags including, but not limited to histidine (His), maltose binding protein (MBP), FLAG, Trx, myc, streptavidin, biotin, human influenza virus hemagluttinin (HA), vesicular stomatitis virus glycoprotein (VSV-G), glycoprotein-D precursor of Herpes simplex virus (HSV), V5, AU1, glutathione-S-transferase (GST), the calmodulin binding domain of the calmodulin binding protein, Protein A, and Protein G. Non-limiting examples of specific protocols for selecting, making and using an appropriate tag are described in, e.g., Epitope Tagging, pp. 17.90-17.93 (Sambrook and Russell, eds., Molecular Cloning A Laboratory Manual, Vol. 3, 3rd ed. 2001), which is herein incorporated by reference in its entirety.

In several embodiments, a particle comprises a nanoparticle, nanosphere, microcapsule, nanocapsule, microsphere, microparticle, bead, colloid, aggregate, flocculate, insoluble salt, emulsion, crystal, detergent, surfactant, dendrimer, copolymer, block polymer, nucleic acid, carbohydrate, lipid, liposome, or insoluble complex. It is contemplated that these types of particles can have any size in the picometer, nanometer, micrometer, or millimeter range along any dimensional axis. As used herein, the term "nanoparticle" refers to any particle having a greatest dimension (e.g., diameter) that is less than about 2500 nm. In some embodiments, the nanoparticle is a solid or a semi-solid. In some embodiments, the nanoparticle is generally centrosymmetric. In some embodiments, the nanoparticle contains a generally uniform dispersion of solid components.

Nanoparticles can have a characteristic dimension of less than about 1 micrometer, where the characteristic dimension of a particle is the diameter of a perfect sphere having the same volume as the particle. For example, the nanoparticle may have a characteristic dimension that is less than 500 nm, 400 nm, 300 nm, 250 nm, 200 nm, 180 nm, 150 nm, 120 nm, 100 nm, 90 nm, 80 nm, 70 nm, 60 nm, 50 nm, 40 nm, 30 nm, or 20 nm, or any number in between the aforementioned sizes. In some embodiments, the nanoparticle can have a characteristic dimension of 10 nm, 20 nm, 30 nm, 40 nm, 50 nm, 60 nm, 70 nm, 80 nm, 90 nm, 100 nm, 120 nm, 150 nm, 180 nm, 200 nm, 250 nm or 300 nm, or any number in between the aforementioned sizes. In other embodiments, the nanoparticle can have a characteristic dimension of 10-500 nm, 10-400 nm, 10-300 nm, 10-250 nm, 10-200 nm, 10-150 nm, 10-100 nm, 10-75 nm, 10-50 nm, 50-500 nm, 50-400 nm, 50-300 nm, 50-200 nm, 50-150 nm, 50-100 nm, 50-75 nm, 100-500 nm, 100-400 nm, 100-300 nm, 100-250 nm, 100-200 nm, 100-150 nm, 150-500 nm, 150-400 nm, 150-300 nm, 150-250 nm, 150-200 nm, 200-500 nm, 200-400 nm, 200-300 nm, 200-250 nm, 200-500 nm, 200-400 nm or 200-300 nm.

In various embodiments, a particle comprises one or more materials including, but not limited to, polymers such as polystyrene, silicone rubber, latex, polycarbonate, polyurethanes, polypropylenes, polymethylmethacrylate, polyvinyl chloride, polyesters, polyethers, and polyethylene. Additional examples of suitable polymers include, but are not limited to the following: polyethylene glycol (PEG); poly (lactic acid-co-glycolic acid) (PLGA); copolymers of PLGA and PEG; copolymers of poly(lactide-co-glycolide) and PEG; polyglycolic acid (PGA); copolymers of PGA and PEG; poly-L-lactic acid (PLLA); copolymers of PLLA and PEG; poly-D-lactic acid (PDLA); copolymers of PDLA and PEG; poly-D,L-lactic acid (PDLLA); copolymers of PDLLA and PEG; poly(ortho ester); copolymers of poly (ortho ester) and PEG; poly(caprolactone); copolymers of poly(caprolactone) and PEG; polylysine; copolymers of polylysine and PEG; polyethylene imine; copolymers of polyethylene imine and PEG; polyhydroxyacids; polyanhydrides; polyhydroxyalkanoates, poly(L-lactide-co-L-lysine); poly(serine ester); poly(4-hydroxy-L-proline ester); poly-α-(4-aminobutyl)-L-glycolic acid; derivatives thereof; combinations thereof; and copolymers thereof.

Further examples of polymeric and non-polymeric materials that can be used in particles of several embodiments include, but are not limited to, poly(lactide), poly(hydroxybutyrate), poly(beta-amino) esters and/or copolymers thereof. Alternatively, the particles can comprise other materials, including but not limited to, poly(dienes) such as poly(butadiene) and the like; poly(alkenes) such as polyethylene, polypropylene and the like; poly(acrylics) such as poly(acrylic acid) and the like; poly(methacrylics) such as poly(methyl methacrylate), poly(hydroxyethyl methacrylate), and the like; poly(vinyl ethers); poly(vinyl alcohols); poly(vinyl ketones); poly(vinyl halides) such as poly(vinyl chloride) and the like; poly(vinyl nitriles), poly(vinyl esters) such as poly(vinyl acetate) and the like; poly(vinyl pyridines) such as poly(2-vinyl pyridine), poly(5-methyl-2-vinyl pyridine) and the like; poly(styrenes); poly(carbonates); poly(esters); poly(orthoesters); poly(esteramides); poly(anhydrides); poly(urethanes); poly(amides); cellulose ethers such as methyl cellulose, hydroxyethyl cellulose, hydroxypropyl methyl cellulose and the like; cellulose esters such as cellulose acetate, cellulose acetate phthalate, cellulose acetate butyrate; and polysaccharides. These materials may be used alone, as physical mixtures (blends), or as copolymers.

In several embodiments, a particle comprises a semiconductor nanocrystal. A semiconductor nanocrystal is a nanocrystal of Group II-VI and/or Group III-V semiconductor compounds. Examples of semiconductor nanocyrstals include, but are not limited to Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs and mixed compositions thereof.

In several embodiments, a particle comprises a metal particle, such as an Au, Ag, Pd, Pt, Cu, Ni, Co, Fe (e.g. iron sulfide), Mn, Ru, Rh, Os, or Ir particle. In various embodiments, a particle comprises a metal oxide particle. Examples of suitable metal oxide particles include zinc oxide, titanium (di)oxide, iron oxide, silver oxide, copper oxide, aluminum oxide, or silicon (di)oxide particles. In certain embodiments, a particle comprises a magnetic particle, such as a magnetic bead, nanoparticle, microparticle, and the like.

In some embodiments, a particle can be associated with a capture probe, such as a second capture probe. In some embodiments, the capture probe can be attached to the particle. In some embodiments, the capture probe comprises a catalyst. In some embodiments, the catalyst comprises horseradish peroxidase. In some embodiments, the capture probe comprises a plurality of catalysts. In some embodiments, the catalysts are the same. In some embodiments, one or more catalysts are different.

In some embodiments, a particle can be associated with a catalyst. In some embodiments, the catalyst can be attached to the particle. In some embodiments, the catalyst comprises horseradish peroxidase. In some embodiments, the particle comprises a plurality of catalysts. In some embodiments, the catalysts are the same. In some embodiments, one or more catalysts are different.

Catalysts

Some embodiments of the methods, compositions and systems provided herein include catalysts. In some embodiments, the presence of a catalyst is useful to amplify a signal. In some embodiments, a catalyst promotes a reaction that results in the formation of a precipitate. In some embodiments, a catalyst comprises an enzyme. Examples of such enzymes include horseradish peroxidase, alkaline phosphatase, and β-galactosidase. Examples of reagents useful with such catalysts include 4-chloro-1-naphthol, Hanker-Yates reagent, 3,3'-diaminobenzidine, and 3-amino-9-ethylcarbazole.

In some embodiments, a catalyst is attached to a capture probe. In some embodiments, a catalyst is attached to a capture probe directly. In some embodiments, a capture probe comprises a first affinity tag, and a catalyst comprises a second affinity tag. In some such embodiments, the first affinity tag can bind to the second affinity tag, therefore associating the capture probe and catalyst with each other. Examples of affinity tags include biotin, streptavidin, poly-His, and nickel, and derivatives thereof.

Methods for Measuring a Target Analyte

Some embodiments of the methods, compositions and systems provided herein include a method for detecting and/or measuring the level of a target analyte. Some such embodiments include obtaining a planar substrate comprising an optical sensor having a first capture probe attached thereto; contacting the first capture probe with a sample comprising a target analyte that selectively binds to the first capture probe; contacting the bound target analyte with a second capture probe that selectively binds to a complex comprising the bound target analyte, wherein the second capture probe comprises a catalyst; contacting the catalyst with a reagent under conditions where the reagent forms a precipitate in the presence of the catalyst; and measuring a change in resonance wavelengths at the optical sensor, thereby measuring the level of the target analyte.

In some embodiments, a method of detecting a target analyte includes obtaining a planar substrate comprising an optical sensor having a first capture probe attached thereto; contacting the first capture probe with a sample comprising a target analyte that selectively binds to the first capture probe; contacting the bound target analyte with a second capture probe that selectively binds to a complex comprising the bound target analyte, wherein the second capture probe comprises a first affinity tag; contacting the bound second capture probe with a second affinity tag that selectively binds to the bound first affinity tag, wherein the second affinity tag comprises a catalyst; contacting the catalyst with a reagent under conditions where the reagent forms a precipitate in the presence of the catalyst; and measuring an increase in precipitate formation at the optical sensor, thereby detecting the target analyte. In some embodiments, an increase in precipitate formation is indicative of the level of the target analyte in the sample. In some embodiments, the quantity of precipitate formation is indicative of the level of the target analyte in the sample. In some embodiments, an increase in the rate of precipitate formation is indicative of the level of target analyte in the sample. In some embodiments, an increase in in precipitate formation is measured by determining a change in resonance wavelengths at the optical sensor.

In some embodiments, the first and second affinity tags are each selected from the group consisting of biotin, streptavidin, poly-His, and nickel.

In some embodiments, the first capture probe comprises an antibody or antigen-binding fragment thereof. In some embodiments, the first capture probe comprises an antibody selected from the group consisting of anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the second capture probe selectively binds to the target analyte. In some embodiments, the second capture probe selectively binds to the bound target analyte. In some embodiments, the second capture probe comprises an antibody or antigen-binding fragment thereof. In some embodiments, the second capture probe comprises an antibody selected from the group consisting of, anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the catalyst is selected from the group consisting of horseradish peroxidase, alkaline phosphatase, and β-galactosidase. In some embodiments, the reagent is selected from the group consisting of 4-chloro-1-naphthol, Hanker-Yates reagent, 3,3'-diaminobenzidine, and 3-amino-9-ethylcarbazole.

In some embodiments, the catalyst is contacted with an additional agent, such as hydrogen peroxide. In some embodiments, the concentration of hydrogen peroxide is less than about 0.001%, 0.002%, 0.003%, 0.002%, 0.001%, 0.009%, 0.008%, 0.007%, 0.006%, 0.005%, 0.004%, and 0.0003%, or within a range between any two of the foregoing concentrations.

In some embodiments, the optical sensor is washed between any of the foregoing steps.

In some embodiments, a target analyte is detected having a concentration less than about 1000 pg·ml, 500 pg/ml, 100 pg/ml, 50 pg/ml, 10 pg/ml, and 1 pg/ml, or within a range between any two of the foregoing concentrations.

In some embodiments, the target analyte comprises a cytokine. In some embodiments, the analyte is selected from the group consisting of IL-2, IL-4, IL-6, and IL-8.

In some embodiments, a sample comprises the analyte. In some embodiments, the sample is selected from the group consisting of serum and cerebrospinal fluid.

In some embodiments, the optical sensor comprises an optical ring resonator. In some embodiments, the optical sensor comprises a waveguide structure. In some embodiments, the optical sensor comprises a well. In some embodiments, the planar substrate comprises a plurality of optical sensors. In some embodiments, a planar substrate can include at least about 1, 2, 5, 10, 100, 1000, 10000, 100000, 1000000 optical sensors, or a planar substrate can include a plurality of optical sensors, in which the plurality is a number within a range between any of the foregoing numbers of optical sensors. In some embodiments, the planar substrate comprises a thermal control. In some embodiments, the planar substrate comprises an optical chip. In some embodiments, the planar substrate comprises a multiwell plate. In some embodiments, the planar substrate comprises a flowcell.

Kits

Some embodiments of the methods, compositions and systems provided herein include a kit for measuring the level of a target analyte. Some such kits include a planar substrate comprising an optical sensor having a first capture probe attached thereto, wherein the first capture probe selectively binds to the target analyte; a second capture probe that selectively binds to a complex comprising the target analyte bound to the first capture probe, wherein the second capture probe comprises a catalyst; and a reagent that can form a precipitate in the presence of the catalyst. In some embodiments, the second capture probe comprises a first affinity tag. In some embodiments, a second affinity tag that selectively binds to the first affinity tag, wherein the second affinity tag comprises the catalyst.

In some embodiments, a kit for detecting a target analyte comprising: a planar substrate comprising an optical sensor having a first capture probe attached thereto, wherein the first capture probe selectively binds to the target analyte; a second capture probe that selectively binds to a complex comprising the target analyte bound to the first capture probe, wherein the second capture probe comprises a first affinity tag; a second affinity tag that selectively binds to the first affinity tag, wherein the second affinity tag comprises a catalyst; a reagent that can form a precipitate in the presence of the catalyst.

In some embodiments, the first and second affinity tags are each selected from the group consisting of biotin, streptavidin, poly-His, and nickel.

In some embodiments, the first capture probe comprises an antibody or antigen-binding fragment thereof. In some embodiments, the first capture probe comprises an antibody selected from the group consisting of anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the second capture probe selectively binds to the target analyte. In some embodiments, the second capture probe selectively binds to the bound target analyte. In some embodiments, the second capture probe comprises an antibody or antigen-binding fragment thereof. In some embodiments, the second capture probe comprises an antibody selected from the group consisting of, anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the catalyst is selected from the group consisting of horseradish peroxidase, alkaline phosphatase, and β-galactosidase. In some embodiments, the reagent is selected from the group consisting of 4-chloro-1-naphthol, Hanker-Yates reagent, 3,3'-diaminobenzidine, and 3-amino-9-ethylcarbazole.

In some embodiments, the kit includes hydrogen peroxide. In some embodiments, the concentration of hydrogen peroxide is less than about 0.001%, 0.002%, 0.003%, 0.002%, 0.001%, 0.009%, 0.008%, 0.007%, 0.006%, 0.005%, 0.004%, and 0.0003%, or within a range between any two of the foregoing concentrations.

In some embodiments, the kit is adapted to detect a target analyte is detected having a concentration less than about 1000 pg·ml, 500 pg/ml, 100 pg/ml, 50 pg/ml, 10 pg/ml, and 1 pg/ml, or within a range between any two of the foregoing concentrations.

In some embodiments, the kit is adapted to detect a target analyte comprising a cytokine. In some such embodiments, the analyte is selected from the group consisting of IL-2, IL-4, IL-6, and IL-8.

In some embodiments, a sample comprises the analyte. In some embodiments, the sample is selected from the group consisting of serum and cerebrospinal fluid.

In some embodiments, the optical sensor comprises an optical ring resonator. In some embodiments, the optical sensor comprises a waveguide structure. In some embodiments, the optical sensor comprises a well. In some embodiments, the planar substrate comprises a plurality of optical sensors. In some embodiments, a planar substrate can include at least about 1, 2, 5, 10, 100, 1000, 10000, 100000, 1000000 optical sensors, or a planar substrate can include a plurality of optical sensors, in which the plurality is a number within a range between any of the foregoing numbers of optical sensors. In some embodiments, the planar substrate comprises a thermal actuator. In some embodiments, the planar substrate comprises an optical chip. In some embodiments, the planar substrate comprises a multiwell plate. In some embodiments, the planar substrate comprises a flowcell.

Systems

Some embodiments of the methods, compositions and systems provided herein include a system for measuring the level of a target analyte comprising. Some such systems include: a planar substrate comprising an optical sensor having a first capture probe attached thereto, wherein the target analyte selectively binds to the first capture probe; a second capture probe that selectively binds to a complex comprising the target analyte bound to the first capture probe, wherein the second capture probe comprises a catalyst; a reagent which can form a precipitate in the presence of the catalyst; and a detector adapted to measure a change in resonance wavelengths at the optical sensor. In some embodiments, a change in resonance wavelengths at the optical sensor is indicative of the level of the target analyte. In some embodiments, the second capture probe is formed by contacting an affinity molecule bound to a first affinity tag with a second affinity tag bound to a catalyst, wherein the second affinity tag selectively binds to the first affinity tag. In some embodiments, the second capture probe comprises an affinity tag bound to a catalyst.

In some embodiments, a system of detecting a target analyte comprises: a planar substrate comprising an optical sensor having a first capture probe attached thereto, wherein the target analyte selectively binds to the first capture probe; a second capture probe that selectively binds to a complex comprising the target analyte bound to the first capture probe, wherein the second capture probe comprises a first affinity tag; a second affinity tag that selectively binds to the bound first affinity tag, wherein the second affinity tag comprises a catalyst; a reagent that forms a precipitate in the presence of the catalyst; and a detector adapted to measure an increase in precipitate formation.

In some embodiments, the increase in precipitate formation is indicative of the level of the target analyte in the sample.

In some embodiments, the first and second affinity tags are each selected from the group consisting of biotin, streptavidin, poly-His, and nickel.

In some embodiments, an increase in precipitate formation is measured by a change in resonance wavelengths at the optical sensor.

In some embodiments, the first capture probe comprises an antibody or antigen-binding fragment thereof. In some embodiments, the first capture probe comprises an antibody selected from the group consisting of anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the second capture probe comprises an antibody or antigen-binding fragment thereof. In some embodiments, the second capture probe selectively binds to the target analyte. In some embodiments, the second capture probe selectively binds to the bound target analyte. In some embodiments, the second capture probe comprises an antibody selected from the group consisting of, anti-IL-2 from clone 555051, anti-IL-2 from clone 555040, anti-IL-2 from clone MQ1-17H12, anti-IL-6 from clone BAF206, anti-IL-6 from clone MAB206, anti-IL-6 from clone MQ2-13A5, anti-IL-6 from clone MQ2-39C3, and an antigen-binding fragment thereof.

In some embodiments, the catalyst is selected from the group consisting of horseradish peroxidase, alkaline phosphatase, and β-galactosidase. In some embodiments, the reagent is selected from the group consisting of 4-chloro- 1-naphthol, Hanker-Yates reagent, 3,3'-diaminobenzidine, and 3-amino-9-ethylcarbazole.

In some embodiments, an additional reagent includes hydrogen peroxide. In some embodiments, the concentration of hydrogen peroxide is less than about 0.001%, 0.002%, 0.003%, 0.002%, 0.001%, 0.009%, 0.008%, 0.007%, 0.006%, 0.005%, 0.004%, and 0.0003%, or within a range between any two of the foregoing concentrations.

In some embodiments, the planar surface is adapted for washing the optical sensor.

In some embodiments, the system is adapted to detect a target analyte is detected having a concentration less than about 1000 pg·ml, 500 pg/ml, 100 pg/ml, 50 pg/ml, 10 pg/ml, and 1 pg/ml, or within a range between any two of the foregoing concentrations. In some embodiments, the analyte comprises a cytokine. In some embodiments, the analyte is selected from the group consisting of IL-2, IL-4, IL-6, and IL-8.

In some embodiments, a sample comprises the analyte. In some embodiments, the sample is selected from the group consisting of serum and cerebrospinal fluid.

In some embodiments, the optical sensor comprises an optical ring resonator. In some embodiments, the optical sensor comprises a waveguide structure. In some embodiments, the optical sensor comprises a well. In some embodiments, the planar substrate comprises a plurality of optical sensors. In some embodiments, a planar substrate can include at least about 1, 2, 5, 10, 100, 1000, 10000, 100000, 1000000 optical sensors, or a planar substrate can include a plurality of optical sensors, in which the plurality is a number within a range between any of the foregoing numbers of optical sensors. In some embodiments, the planar substrate comprises a thermal control. In some embodiments, the planar substrate comprises an optical chip. In some embodiments, the planar substrate comprises a multiwell plate. In some embodiments, the planar substrate comprises a flowcell.

EXAMPLES

Example 1—IL-2 and IL-4 Assays

This example illustrates development of an assay for detection of example target analytes, IL-2 and IL-4, using enzymatic enhancement of a sandwich based assay with microring detection. This overall assay is depicted schematically in FIG. 5. Briefly, in a four-step assay, a cytokine sandwich assay with a biotinylated secondary antibody is followed by addition of streptavidin-HRP conjugate. Subsequent introduction of freshly prepared hydrogen peroxide in 4-Cl-1-naphthol substrate solution allows for the catalytic formation of the 4-Cl-1-naphthon precipitate only at rings with bound HRP.

Optimization of Enzymatic HRP Process for Rapid Precipitate Formation

Sandwich assays and antibody pair selections have been demonstrated in previous work with IL-2[9,11] and IL-6[10]. Due to extensive work with these targets in previous work, the advances described in this disclosure have a well-defined benchmark for assay sensitivity comparisons and assay complexity and time-to-result tradeoffs. Though enzymatic amplification introduces complexity and extra time to the assay, the impressive sensitivity gains and highly quantitative signals make the assay extremely valuable for expanding the potential applications for ring resonator biosensing.

Selection of 4-Cl-1-Naphthol as HRP Substrate

HRP is a commonly used enzymatic label that catalyzes decomposition of two molecules of its natural substrate, hydrogen peroxide, into water and oxygen.[12] Since HRP has low selectivity for its natural substrate, many chromogenic substrates have been developed and compared for use as HRP substrates with ELISA.[13] These include 4-chloro-1-naphthol (4-CN), o-phenylenediamine, 3-amino-9-ethyl carbazole, 2,2'-azino-bis(3-ethylbenzthiazolone), 4-aminoantipyrene+a phenol, 3,3'-diaminobenzidine (DAB), 3,3',5,5'-tetramethylbenzidine (TMB), 2,2'-azino-bis(3-ethylbenzthiazolone), Hanker-Yates reagent (HYR), 3-methyl-2-benzothiazolinone hydrazone hydrochloride (MBTH)+3-dimethylaminobenzoic acid, o-dianisidine, and dicarboxidine. Of these possible substrates and others, only some produce water-insoluble products following oxidation: 4-CN, HYR, DAB, and 3-amino-9-ethylcarbazole.[12] HRP is known to catalyze the oxidation of the substrate 4-CN by hydrogen peroxide to form the insoluble blue precipitate, 4-Cl-1-naphthon.[14] Oxidation of the 4-CN substrate produces 4-Cl-1-naphthon, a water-insoluble blue precipitate. Hydrogen peroxide oxidizes 4-CN, albeit very slowly, without HRP. Thus, it is preferable to combine the substrate and hydrogen peroxide immediately before the final step of the microring sandwich assay. Streptavidin-HRP conjugates bound to biotinylated secondary antibodies catalyze 4-Cl-1-naphthon precipitate formation at microrings that have bound the target analyte. This reaction scheme is presented in FIG. 4. Though traditional ELISA makes use of the blue color change following substrate oxidation, the requirements of a RI-based ring resonator assay require different optimization. Color intensity and resistance to fading is irrelevant to this work, as the signal arises simply from precipitation of the oxidized substrate on specific microrings. Relevant factors include precipitation rate, precipitate deposition specificity, and reproducibility of the reaction. TMB was also evaluated as an HRP substrate without success. Though blue color was formed as evidence of the enzymatic process, the TMB did not effectively precipitate on the rings to amplify the signal. TMB seems to have poor solubility characteristics, despite its use in SPRI amplification.[8]

Materials

4-CN solution (0.48 mM 4-Chloro-1-naphthol in 50 mM Tris-HCl/0.2M NaCl/17% methanol), a product normally used for Western Blot visualization, was obtained from Sigma-Aldrich (St. Louis, Mo.). High-sensitivity streptavidin-HRP (SA-HRP) conjugate and EZ-Link NHS-PEG4-Biotin were obtained from Pierce (Rockford, Ill.), and 30% hydrogen peroxide was obtained from Macron Chemicals (Center Valley, Pa.). anti-IL-2 clone 555051 (capture Ab) and biotin anti-IL-2 clone 555040 (detection Ab) were obtained from BD Biosciences (San Jose, Calif.). anti-IL-2 43-2 and HRP-conjugated anti-IL-2 14-0 were obtained from Abcam (Cambridge, Mass.), while anti-IL-2 MΩ1-17H12, polyclonal anti-IL-2, and recombinant human IL-2 were obtained from eBioscience (San Diego, Calif.). anti-IL-6 clone MAB206 (capture Ab) and biotin anti-IL-6 clone BAF206 (detection Ab) were obtained from R&D Systems (Minneapolis, Minn.). Recombinant human IL-6, anti-IL-6 clone MQ2-13A5, and anti-IL-6 clone MQ2-39C3 were obtained from eBioscience (San Diego, Calif.). Mouse IgG1k isotype control clone P3 and anti-IL-4 clone 8D4-8 (both from eBioscience) were used as control antibodies to verify assay selectivity.

Antibody Functionalization Methods

Ring resonator optical scanning instrumentation, software, and chips have been described previously.[15,16] Prior to functionalization, chips were cleaned by a 30-s immersion in piranha solution (3:1 $H_2SO_4$:30% $H_2O_2$) followed by a water rinse and drying in a nitrogen stream. After a 10-min sonication in 100% ethanol, chips were dried in a nitrogen stream and spotted with 30 μL of 1 mg/mL HyNic silane (3-N-((6-(N'-isopropylidene-hydrazino))nicotinamide)propylthriethoxysilane, SoluLink, San Diego, Calif.) in 95% ethanol/5% dimethylformamide (DMF) for a 20-min incubation at room temperature to install a hydrazine moiety. Following silanization, chips were sonicated for 5 min in 100% ethanol to remove physisorbed silane. After drying in a nitrogen stream, chips were loaded into a previously described fluidic cell[16] with a custom 4-channel fluidic gasket[17] (Scarpati Technical Services/RMS Laser, San Diego, Calif.) to direct antibody solution flow to defined groups of 4-6 rings each.

Figure 6:
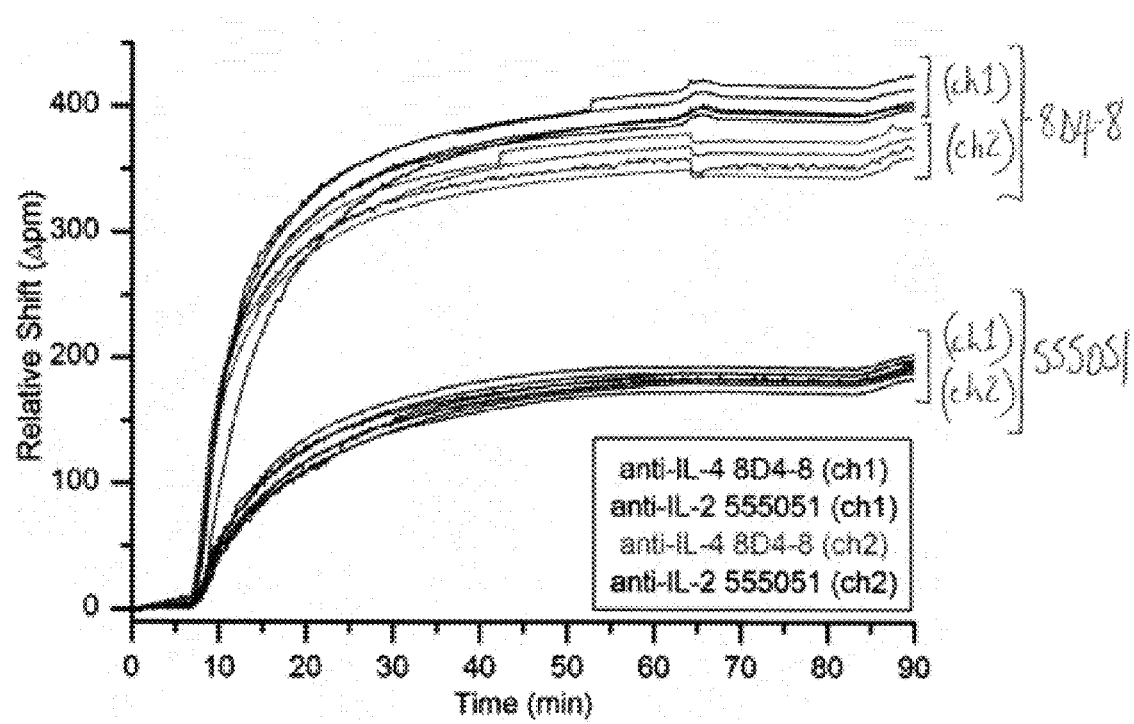
FIG. 6 depicts capture antibody loading with four-channel microfluidics.

Capture antibodies were first buffer-exchanged into 100 mM phosphate-buffered saline (PBS) pH 7.4 with spin desalting columns (7 k molecular weight cutoff, Pierce). In separate reaction vials, lysine residues on the 4 capture antibodies were functionalized with aldehyde moieties by reacting 0.5 mg/mL antibody with a 10-fold molar excess of succinimidyl-4-formyl benzoate (S-4FB, SoluLink, 0.5 mg/mL in DMF) for 2 h at room temperature. After another buffer exchange into 100 mM PBS pH 7.4 to remove excess S-4FB and DMF, the antibody solutions were diluted to 10 μg/mL in 100 mM PBS pH 6 with 50 mM aniline. The capture antibody-4FB conjugates were flowed over the chip using the previously described fluidics controlled by a multi-channel programmable syringe pump (BS-9000-8, Braintree Scientific Inc., Braintree, Mass.) operated in withdraw mode at 2 μL/min. Covalent antibody attachment by hydrazone bond formation between the hydrazine silane surface and aldehyde-modified antibodies was catalyzed by aniline[18] in the running buffer to allow full surface coverage after 30-60 min. Four-channel antibody functionalization was performed such that each of the two channels of 12 sensor microrings had anti-IL-2 or anti-IL-6-functionalized rings upstream of control (anti-IL-4 of mouse IgG isotype control) rings, as described in FIG. 6. Groups of four to six rings in each of four channels were functionalized simultaneously. This functionalization strategy allowed anti-IL-2 rings to be upstream of anti-IL-4 control rings when fluidics are switched to a two-channel setup after the blocking step (FIG. 6). After multiplexed antibody functionalization, chips were blocked overnight at 4° C. in StartingBlock PBS buffer (cat. #37538, Pierce).

Optimized Assay Conditions

For enzymatic amplification of cytokine sandwich assays, a four-step assay was designed. This assay is depicted schematically in FIG. 5. After primary binding of cytokines to anti-cytokine capture antibodies on the rings, secondary biotin anti-cytokine antibodies were introduced to form a sandwich pair. Next, complexation of streptavidin-HRP (SA-HRP) conjugate to the sandwich pair introduces the enzyme at appropriate rings in a concentration-dependent manner. Finally flowing hydrogen peroxide with 4-CN causes specific precipitation of 4-Cl-1-naphthon at the ring surface. The assay conditions (75-min total assay time, including rinse steps) are as follows (NOTE: all steps maintain a 30 μL/min flow rate and utilize room-temperature reagents):

(1) 20-min primary cytokine binding by incubation with sample or standard in 10 mM PBS pH 7.4+0.1 mg/mL BSA+0.05% Tween-20 (PBS-BSA-T);
(2) 2-min buffer rinse (PBS-BSA-T);
(3) 10-min binding of biotinylated secondary anti-cytokine antibody (2 μg/mL in PBS-BSA-T);
(4) 2-min buffer rinse (PBS-BSA-T);
(5) 10-min binding of streptavidin-HRP conjugate (2 μg/mL in PBS-BSA-T);
(6) 3-min buffer rinse (PBS-BSA-T);
(7) 25-min introduction of 465 μM 4-CN/0.01% hydrogen peroxide solution in 17% methanol for precipitation of 4-Cl-1-naphthon;
(8) Buffer rinse (PBS-BSA-T).

The ratio of 4-CN to hydrogen peroxide was carefully selected for optimal signal amplification and precipitation rate; other ratios of 4-CN: hydrogen peroxide gave little to no signal, and excess hydrogen peroxide was observed to quench the reaction. Preferably, this solution was prepared directly (within 1-2 min) before use by adding 45 μL of 0.3% hydrogen peroxide (1:100 dilution of 30% hydrogen peroxide in distilled water) to 1.5 mL of 480 μM 4-CN solution in methanol (from Sigma-Aldrich) that has been already brought to room temperature. The solution was vortexed to mix and then immediately used in Step 7 above. The 17% methanol in the 4-CN solution caused a ~300-pm bulk RI shift, immediately followed by specific precipitation on appropriate rings in a cytokine-concentration-dependent manner. A fast flow rate (30 uL/min) was necessary to ensure that substantial uncatalyzed reaction of 4-CN and hydrogen peroxide did not occur within the inlet tubing prior to reaching the chip.

Enzymatic Amplification of IL-2 Sandwich Assay

Figure 7:
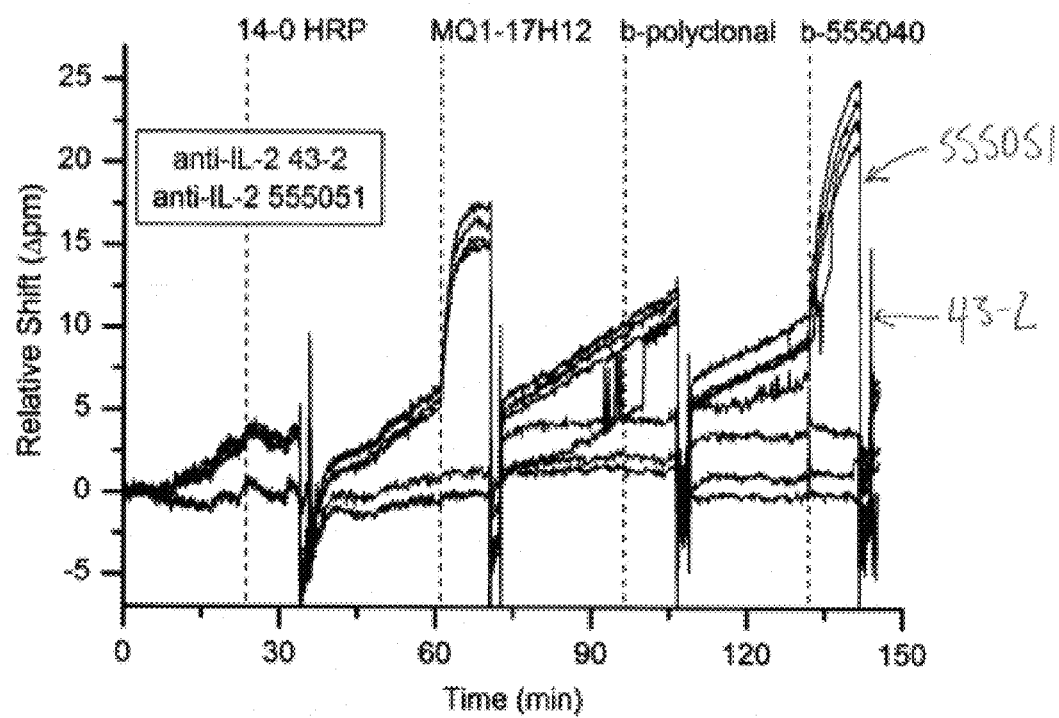
FIG. 7 depicts screening of IL-2 antibody sandwich pairs.

The first step in creating an enzymatic amplification assay for IL-2 involved screening a variety of antibody pairs to determine the optimal capture and detection antibody combination. FIG. 7 shows a graph for an assay to screen IL-2 antibody sandwich pairs in which 10 ng/mL IL-2 sandwich assays were performed with a variety of antibody sandwich pairs involving either clone 555051 (BD) or clone 43-2 (Abcam) as capture antibody. In each case, primary 10 ng/mL IL-2 binding was evident on 555051, but not on 43-2. Only 555051 was a suitable capture antibody for IL-2, and biotin anti-IL-2 555040 (BD) represents the most effective detection antibody (MQ1-17H12 from eBioscience also demonstrated effectiveness as a detection antibody). A low-pH rinse was used to regenerate the capture antibodies between each sandwich assay test. All responses are corrected to anti-IL-5 control rings. As shown in FIG. 7, capture antibody clone 555051 paired with detection antibody 555040 shows the greatest affinity and signal response in the 10 ng/mL IL-2 test. This result highlights the use of comparing commercial antibodies side-by-side using an identical assay on an identical biosensing platform.

Figure 8:
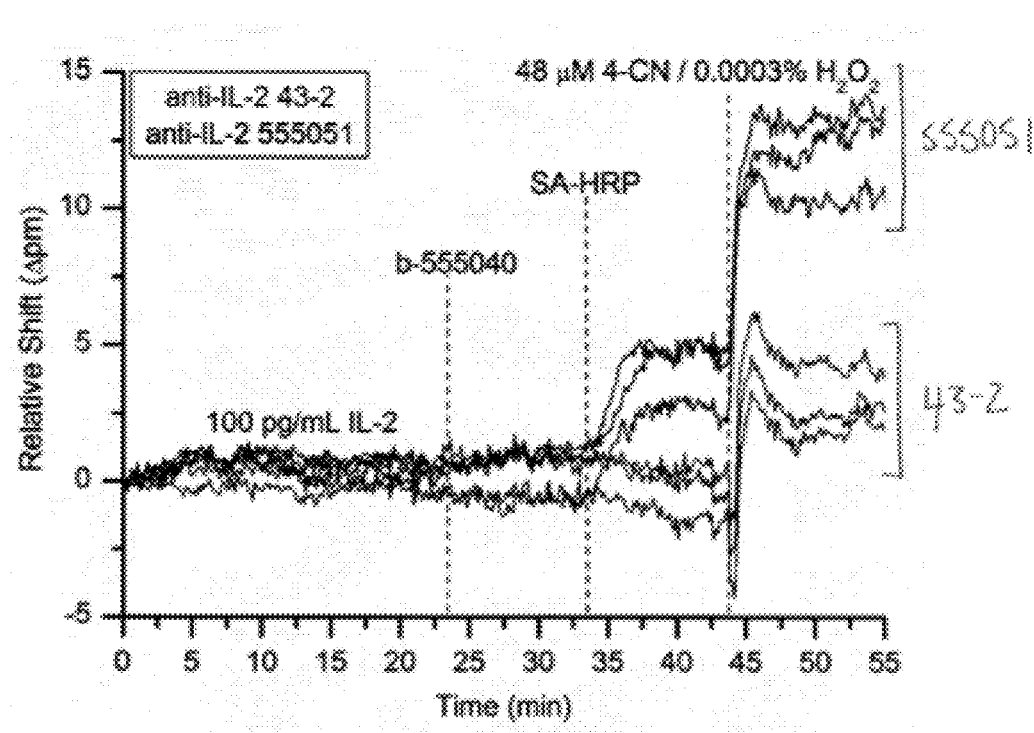
FIG. 8 depicts a 100 pg/mL IL-2 sandwich assay with enzymatic amplification.

With the highest affinity antibody pair chosen, the next step was optimization of enzymatic amplification assay conditions. Initial attempts with 1) TMB as an HRP substrate and 2) with dilute concentrations of 4-CN substrate solution were unsuccessful. Since 4-CN is provided in a 17% methanol solution, initial work sought to prevent the bulk RI shift associated with high solvent concentration by substantially diluting this methanol solution. An example of an enzymatically amplified IL-2 sandwich assay under dilute 4-CN and hydrogen peroxide conditions is shown in FIG. 8. In the assay depicted in FIG. 8, 100 pg/mL IL-2 sandwich assay with enzymatic amplification was carried out under dilute 4-CN/peroxide conditions. Though clearly detectable upon addition of streptavidin-HRP conjugate (SA-HRP), the addition of dilute 4-CN and peroxide provided only minor signal boost. Interestingly, despite no measurable response to the IL-2 sandwich on the clone 43-2 rings during the first three assay steps, the final amplification step gave a small signal. All responses were corrected to anti-IL-5 control rings.

Though 100 pg/mL IL-2 was clearly detected before the fourth assay step (addition of 4-CN and peroxide), the final enzymatic amplification step provided only a minor signal boost. Furthermore, it was also found that adding additional hydrogen peroxide did not improve the enzymatic deposition of 4-Cl-1-naphthon.

Figure 9:
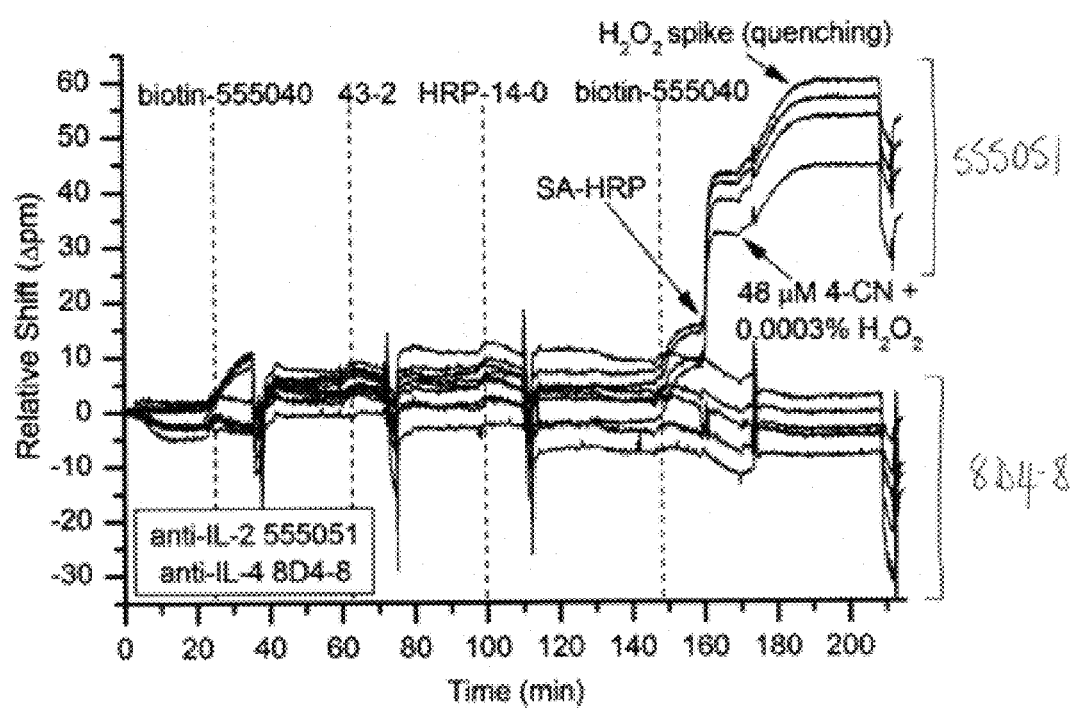
FIG. 9 depicts quenching of enzymatic deposition of 4-Cl-1-naphthon precipitate by high hydrogen peroxide concentration.

FIG. 9 depicts quenching of enzymatic deposition of 4-Cl-1-naphthon precipitate by high hydrogen peroxide concentration in which after a variety of 10 ng/mL IL-2 sandwich assay antibody combinations (which confirm and extend the data in FIG. 7), enzymatic amplification was carried out with streptavidin-HRP conjugate (SA-HRP) at t=160 min followed by dilute 4-CN/hydrogen peroxide at t=173 min. The initial 48 µM 4-CN/0.0003% hydrogen peroxide solution was spiked with 0.3% hydrogen peroxide at t=186 min to a final concentration of 0.003% hydrogen peroxide, which appeared to quench the precipitation reaction. This process was carried out at a low flow rate (5 µL/min). Importantly, no precipitation was observed on control anti-IL-4 rings. As shown in FIG. 9, increasing the peroxide concentration from 0.0003% (100 µM) to 0.003% (1 mM) while maintaining dilute (48 µM) 4-CN appeared to quench the enzymatic process. This result demonstrates the narrow window of 4-CN:$H_2O_2$ ratio that is required for effective enzymatic deposition of 4-Cl-1-naphthon.

Further testing of reaction conditions demonstrated that a combination of more concentrated 4-CN substrate coupled with a higher flow rate are vital to efficient precipitate deposition. The final assay step involves 465 µM 4-CN and 0.01% (3 mM) $H_2O_2$ at 30 µL/min.

Figure 10:
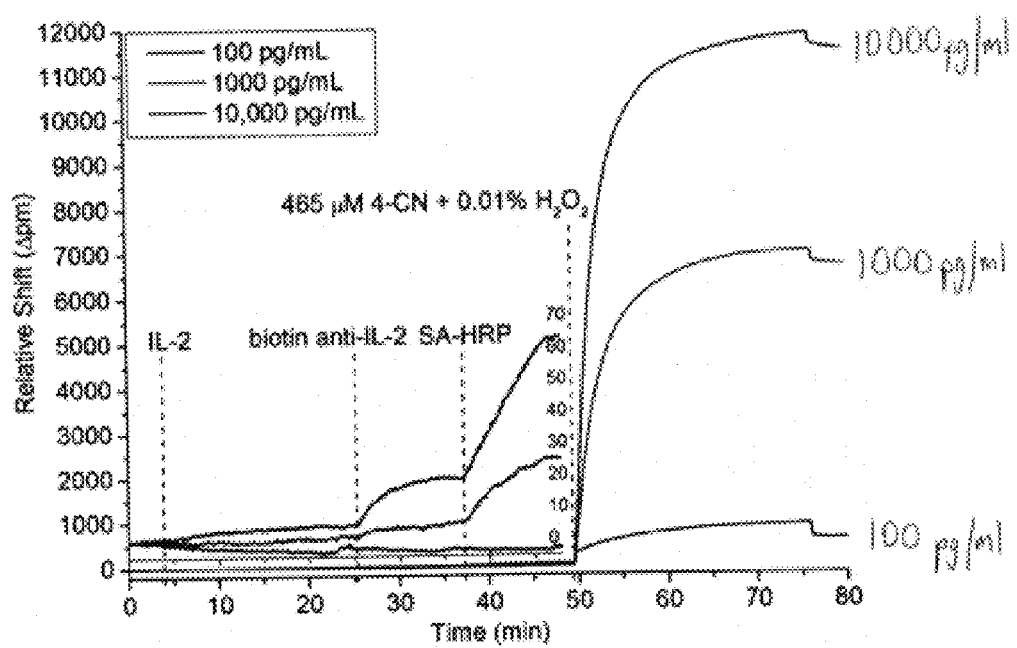
FIG. 10 depicts large signal amplification with enzymatic amplification gives nm-scale shifts down to 100 pg/mL IL-2.

FIG. 10 depicts that large signal amplification with enzymatic amplification gives nm-scale shifts down to 100 pg/mL IL-2 in which representative rings for each of three IL-2 concentrations showed a concentration-dependent resonant wavelength shift upon addition of 465 µM 4-CN and 0.01% $H_2O_2$ to bound streptavidin-HRP conjugate (SA-HRP) at t=50 min. The inset of FIG. 10 shows a zoom into the region of t=0-48 min prior to enzymatic amplification, demonstrating secondary antibody and SA-HRP shifts that are evident at 1 and 10 ng/mL IL-2 concentrations. The relative shift axis for the zoomed-in region is shown to the right of the inset of FIG. 10. These optimized assay conditions were used in subsequent IL-2 calibration experiments. As shown in FIG. 10, nm-scale resonant wavelength shifts are observed under optimized 4-CN and $H_2O_2$ conditions. 100 pg/mL represents the lowest concentration ever detected with a traditional IL-2 ring resonator sandwich assay (<1 pm shift), but this concentration generates a nearly 1 nm shift with enzymatic amplification. Following an initial ~300-pm bulk RI shift upon addition of substrate (due to 17% methanol in the 4-CN solution), 4-Cl-1-naphthon precipitates specifically on anti-IL-2 rings. With these conditions, a large-scale calibration of IL-2 enzymatic response was performed next.

Figure 11:
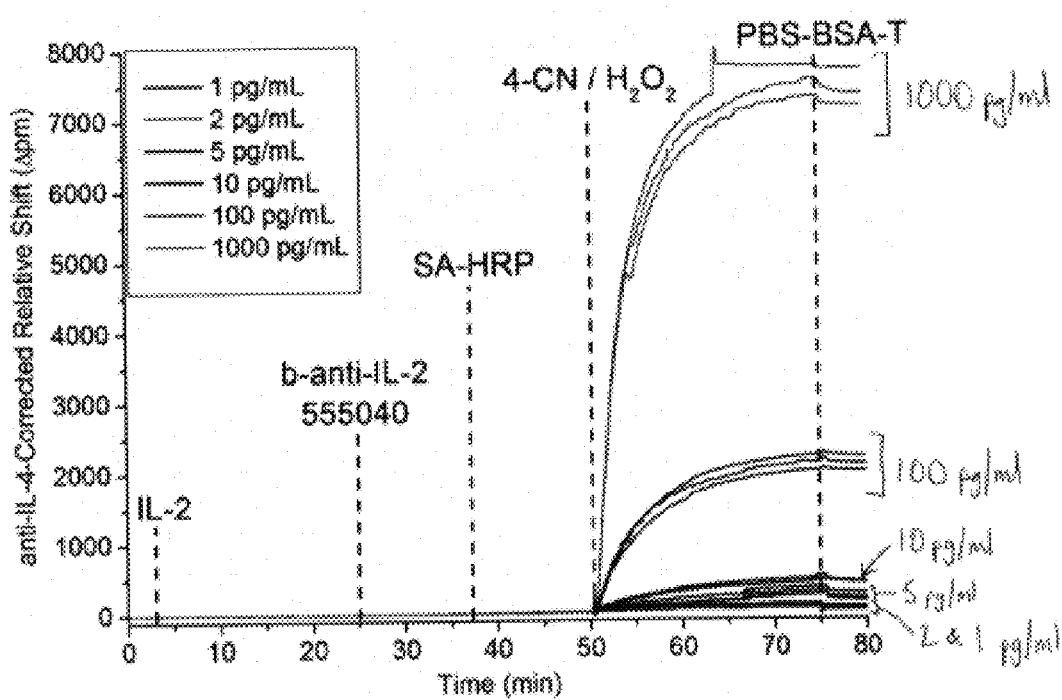
FIG. 11 depicts calibration with four-step HRP enzymatic amplification assay.

As described in FIG. 6, the chips were functionalized so as to enable two independent sets of anti-IL-2 capture antibody rings upstream of anti-IL-4 control rings. Thus, each chip was simultaneously used for two IL-2 concentration standards in independent fluidic channels. FIG. 11 shows the result of the multi-chip calibration of enzymatic signal for IL-2 sandwich assays (concentration range: 1 pg/mL-1 ng/mL). In the assay depicted in FIG. 11, IL-2 calibration with four-step HRP enzymatic amplification assay. The addition of IL-2 (t=3 min), biotin anti-IL-2 555040 (t=25 min), streptavidin-HRP (t=37 min), 465 µM 4-CN/0.01% $H_2O_2$ (t=50 min), and a final buffer rinse (t=75 min) are marked by the dashed lines. Based on two-channel multi-chip calibration at a variety of IL-2 concentrations, FIG. 11 demonstrates the ability to quantify IL-2 over a broad dynamic range with a detection limit of 1 pg/mL using a ~1-h assay. Concentration-dependent responses were observed over a range spanning 4 logs (1-10,000 pg/mL, see FIG. 10 for 10,000 pg/mL response). All responses were corrected to downstream anti-IL-4-functionalized rings, which were necessary for subtracting off the ~300-pm bulk RI shift at t=50 min due to 17% methanol in the 4-CN solution. This calibration plot shows that IL-2 concentrations as low as 1 pg/mL can be detected using enzymatic amplification, although 1 and 2 pg/mL signals are difficult to differentiate in this case. However, substantial differentiation of 5 and 10 pg/mL standards shows that the assay is ideally suited for samples containing cytokine concentrations between 5 and 1000 pg/mL. This concentration range enables significant broadening of the range of applications for cytokine analysis on the ring resonator platform. Importantly, all responses are corrected to downstream anti-IL-4-functionalized rings, which was necessary for subtracting off the ~300-pm bulk RI shift at t=50 min due to 17% methanol in the 4-CN solution. Negative control experiments (0 ng/mL) showed no enzymatic signal, demonstrating a low background (data not shown). Though IL-2 quantitation with the four-step HRP enzymatic amplification assay requires extra time, the total assay time of just over 1 h is still reasonable and superior to the ELISA time-to-result. By combining the data shown in FIGS. 10 and 11, concentration-dependent enzymatic precipitation responses were observed over a range spanning four logs (1-10,000 pg/mL). To verify the effectiveness of the assay for an additional target, a similar assay was also designed for the cytokine interleukin-6 (IL-6).

Enzymatic Amplification of IL-6 Sandwich Assay

Figure 12:
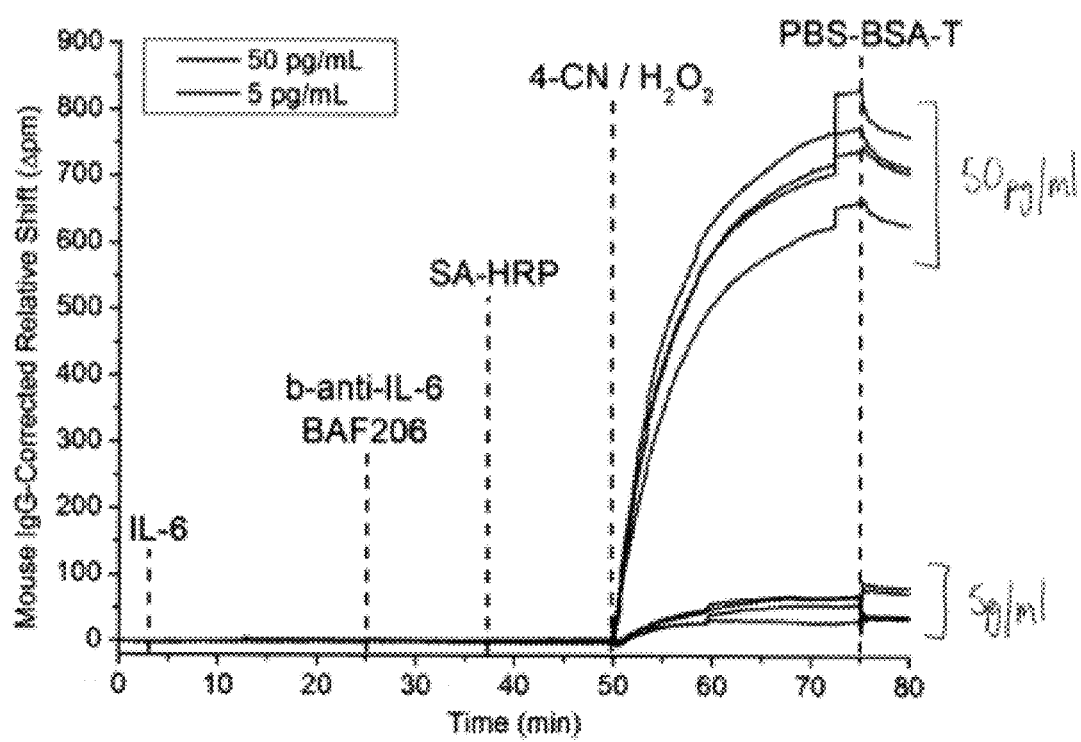
FIG. 12 depicts enzymatic amplification of IL-6 sandwich assay.

The same enzymatic amplification assay was applied to IL-6 detection. Capture anti-IL-6 clone MAB206 and biotinylated detection anti-IL-6 clone BAF206 (both from R&D Systems) were chosen for initial characterization of the assay, although similar results were also obtained for clone MQ2-13A5 as capture antibody. An example of IL-6 enzymatic amplification is shown in FIG. 12, displaying the signals for 5 and 50 pg/mL IL-6. In FIG. 12, the addition of IL-6 (t=3 min), biotin anti-IL-6 BAF206 (t=25 min), streptavidin-HRP (t=37 min), 465 µM 4-CN/0.01% $H_2O_2$ (t=50 min), and a final buffer rinse (t=75 min) are marked by the dashed lines. The capture antibody is anti-IL-6 clone MAB206. All responses were corrected to downstream mouse IgG isotype control antibody-functionalized rings, which were preferred for subtracting off the ~300-pm bulk RI shift at t=50 min due to 17% methanol in the 4-CN solution. The magnitudes of the shifts at the two IL-6 concentrations were comparable to the IL-2 responses at similar concentrations (FIG. 11). The IL-2 antibody pair showed slightly better affinity for IL-2 than the IL-6 antibody pair for IL-6. IL-6 detection down to 5 pg/mL was possible, but further work may permit detection down to 1 pg/mL as was achieved with IL-2.

CONCLUSIONS

In this Example, an optimized HRP-catalyzed amplification scheme was successful for achieving unprecedented cytokine detection limits on the ring resonator biosensing platform. In the past, traditional cytokine sandwich assays on ring resonators were quantitative down to 100 pg/mL-1 ng/mL, depending on the particular analyte and assay format. This disclosure shows that HRP-catalyzed amplification of the cytokine sandwich assay provides a full two orders of magnitude improvement in the detection limit for IL-2. The 1 pg/mL (65 fM) limit of detection represents the lowest concentration of any analyte detected with ring resonators to date. Importantly, the enzymatic process displays a lower and more reproducible background than the bead-based assay, also removing the need for time-consuming bead exchange directly before running the assay.[10] By providing detection capabilities throughout the pg/mL regime, this assay will allow applications that go beyond cell culture work at high cell densities. The ability to quantitate cytokines in the 1-100 pg/mL range is useful for many challenging protein biosensing applications, including serum and cerebrospinal fluid (CSF) diagnostics.

Initial work with IL-6, which has displayed assay performance similar to IL-2, opens up the opportunity to perform CSF diagnostics with a possible Alzheimer's Disease (AD) biomarker. IL-6 is a part of the acute inflammatory response, produced by macrophages and monocytes at areas of inflammation.[19] IL-6, originally known as interferon-beta$_2$, acts as the chief stimulator for production of most acute phase proteins (C-reactive protein, factor B complement, C3, etc).[20] As a general marker of inflammation, IL-6 is released from contracting skeletal muscles into the blood plasma during exercise without altering CSF levels of IL-6, signifying a separation of the CSF and plasma pools of IL-6.[21] Outside of exercise-induced increases in plasma IL-6 levels, IL-6 concentration changes in CSF have been associated with brain trauma,[22] stroke,[23] multiple sclerosis,[24] post-traumatic stress disorder,[25] assorted infections of the central nervous system,[26] and AD.[27] These studies,[22-27] which use commercial ELISAs to compare a variety of disease states to healthy controls, report healthy IL-6 CSF levels in the 1-20 pg/mL range. In general, IL-6 levels noted in these studies[22-27] are observed to increase in CSF as well as plasma or serum, with elevated IL-6 levels often reaching 100-1000 pg/mL. Though a number of studies have looked at AD-induced changes in CSF concentrations of IL-6 and other cytokines,[28] the effect of AD progression on IL-6 levels remains unclear.[27] Discrepancies and inconsistencies exist among a variety of studies aimed at evaluating changes in IL-6 levels associated with AD: IL-6 levels have been reported to increase[29-31] or to not change significantly in AD.[28,32-34] Since IL-6 has definitively been observed by immunohistochemistry in the brain plaques of AD patients[35] and is present at significantly higher levels in AD brain tissue homogenates,[36] it is possible (or even likely) that the discrepancies in IL-6 expression alterations in AD CSF are due to assay inaccuracy and imprecision that cause a lack of statistical significance.

Example 2—IL-2, IL-6 and IL-8 Assays

This example illustrates detection and quantitation of target analytes, IL-2, IL-6, and IL-8, and detection of target analytes in a biological sample, cerebrospinal fluid. The overall strategy for the HRP-enhanced detection of protein targets is shown in FIG. 5. This strategy provides a quantitative method for increasing the per-analyte sensor response.

Materials: PBS buffer was reconstituted from Dulbecco's phosphate buffered saline packets purchased from Sigma-Aldrich (St. Louis, Mo.) into two formulations. A PBS buffer for antibody functionalization (PBS 6) was reconstituted at 10× concentration with the addition of 50 mM aniline and adjusted to pH 6.0. A PBS running buffer (PBS 7.4) was reconstituted at 1× concentration with the addition of 0.1 mg/mL BSA at adjusted to pH 7.4. Starting Block was purchased from Thermo Scientific and used as a blocking agent to prevent nonspecific fouling of the sensor surface. The silane 3-N-((6-(N'-isopropylidene-hydroazino))nicotinamide)propyltriethyoxysilane (HyNic Silane) and succinimidyl-4-formylbenzamide (S-4FB) were purchased from Solulink. Protein desalting columns were purchased from Thermo Scientific. Recombinant interleukin proteins, antibodies, and ELISA kits were obtained from eBioscience, BD Biosciences, or R&D Systems. Item-specific vendors are listed below. Streptavidin-conjugated horseradish peroxidase (SA-HRP) was purchased from Thermo Scientific. When necessary, detection antibodies were biotinylated using a Thermo Scientific EZ-Link NHS-PEG4-Biotin conjugation kit according to the manufacturer's protocol. A 4-chloro-1-naphthol (4-CN) solution was purchased from Sigma-Aldrich. All other reagents were purchased from ThermoFisher, unless otherwise noted, and used as received.

Instrumentation: Sensor chips and instrumentation were obtained from Genalyte (San Diego, Calif.), and their use has been described previously (Washburn, A. L.; Gunn, L. C.; Bailey, R. C. Anal. Chem. 2009, 81, 9499-9506). Briefly, UV photolithography and reactive ion etching were used to fabricate chip features on 8" silicon wafers, prior to dicing into individual 6×6 mm chips. Each chip contains 32 individually addressable microring resonators, 24 of which are used as active biosensors and the other 8 serve as thermal controls. The sensor chip was sandwiched between an aluminum cartridge holder, 0.007" Mylar flow gasket, and Teflon cartridge top to enable microliter-scale 4-plexed fluidic delivery.

Biochemical Modification of Sensor Surface and Capture Agents: Prior to covalent modification with S-4FB, antibodies were buffer exchanged into 100 mM, pH 7.4 PBS using protein desalting columns, followed by a 2 hour incubation with a 10 fold molar excess of S-4FB. Unreacted S-4FB was removed using another desalting column.

Figure 13:
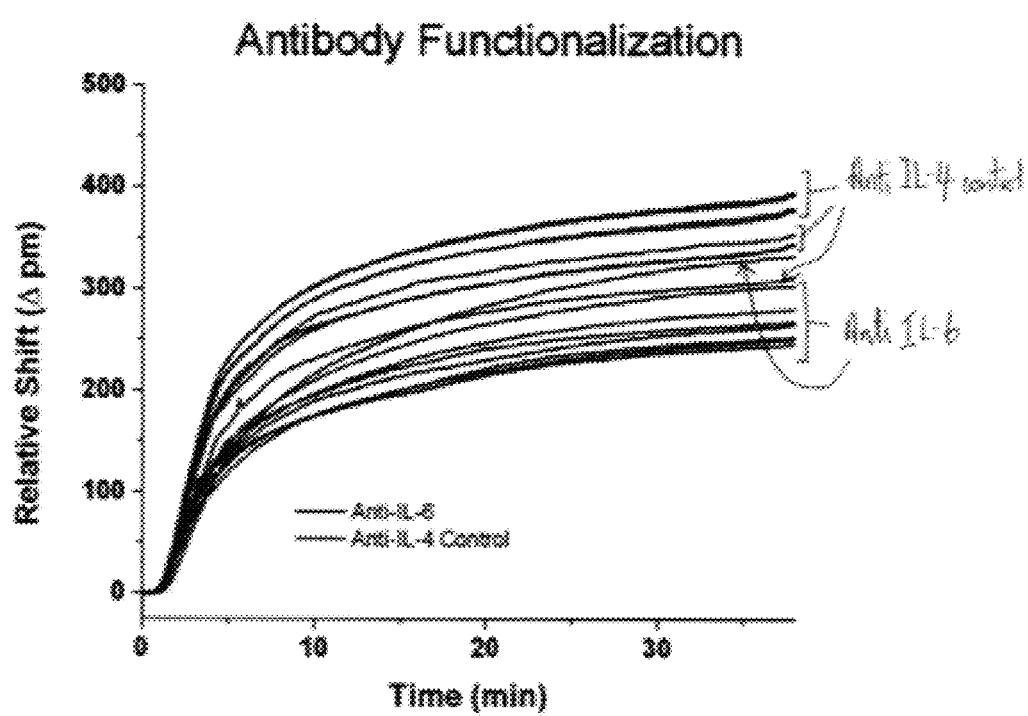
FIG. 13 depicts a typical sensor response for antibody immobilization to the microring surface which resulted in a wavelength shift of between 150-300 pm. It was determined that above 100 pm response, the amount of antibody loading was independent of subsequent antigen, secondary, and tertiary responses.

Sensor chips were initially cleaned in a piranha solution (3:1 $H_2SO_4$/30% $H_2O_2$) for 30 seconds. Following a 3 minute sonication in ethanol, chips were dried under N2 and spotted with a 1 mg/mL HyNic silane solution for 20 minutes, followed by another 3 minute sonication in ethanol and drying with N2. Chips were then loaded into the cartridge assembly and a stable sensor response baseline in PBS 6 buffer was established. Antibody solutions (10 µg/mL) were flowed across the array at 10 µL/min for 5 minutes before reducing the flow rate to 2 µL/min for another 25 minutes. Following a 5 minute buffer rinse, chips were transferred to a Starting Block solution and stored overnight at 4° C. A representative sensor response during the antibody functionalization process is shown in FIG. 13.

Interleukin Assay: After antibody functionalization and overnight blocking, sensor chips were briefly rinsed in PBS 7.4 prior, loaded into the cartridge assembly and then the instrument. All assay steps are performed at a flow rate of 30 µL/min to minimize diffusion-limited kinetics, and all sample/reagent injections are separated by 3 minute buffer rinses. An initial 3 minute low-pH rinse was performed to remove any loosely bound blocking protein, followed by a return to a stable baseline in PBS 7.4. Buffer solutions containing the interleukin samples were flowed across the array for 20 minutes. Subsequently, serial introduction of biotinylated secondary antibodies (each 1 µg/mL) and SA-HRP (2 µg/mL) completes the surface bioconjugation. A freshly prepared 4-CN solution (0.48 mM 4-CN; 0.01% $H_2O_2$; 17% methanol) was then introduced to the sensor for 25 minutes, and the HRP catalyzed oxidation of 4-CN resulted in the deposition of an insoluble precipitate of 4-chloro-1-naphthon (4-CNP), which was detected as an increase in the resonant wavelength of the sensor. Preferably, the $H_2O_2$ was added to the 4-CN solution immediately prior to its introduction to the sensor chip. It should be noted that sensor chips can be regenerated with minimal effects on subsequent assay performance, however, only new sensor chips were used in this study to eliminate such potential sources of error.

Cerebrospinal Fluid: Cerebrospinal fluid (Lot No. BCC062613PMG1) was obtained from Chemed Services, and stored at −80° C. immediately upon receiving. Samples were thawed at room temperature for 30 minutes prior to use, and introduced undiluted to the sensor surface at a flow rate of 15 μL/min, to reduce sample consumption.

Data Analysis: All data analysis was performed using Origin Pro 9.0. Enzymatically-enhanced sensors responses were determined as the difference in resonance wavelength shift before the addition of 4-CN and then after a 5 minute buffer rinse following the 4-CN step. Control rings functionalized with an IgG isotype control (anti-IL-4) were subtracted from target-specific rings to correct for the bulk refractive index shift associated with the introduction of the 4-CN solution. Calibration data was fit to a logistic function:

$$f(c) = \frac{A_1 - A_2}{1 + \left(\frac{c}{c_o}\right)^p} + A_2 \quad [3]$$

where $A_1$ is the initial value limit, $A_2$ is the final value limit, c is the center of the fit, and p is the power of the fit.

Determination of Equilibrium Constant

Equilibrium dissociation constants were determined by fitting both the association and dissociation phases of interleukin binding to a surface-immobilized capture antibody with Equations S1 and S2, respectively:

$$f(t) = A - Ae^{-k_{obs}(t-U)} \quad [S1]$$

$$f(t) = A + Ae^{-k_{obs}(t-U)} \quad [S2]$$

where A is the y offset, $k_{obs}$ is the observed binding constant, t is the time, and U is the time offset. The dissociation rate constant, $k_d$, is directly obtained from the dissociation phase as $k_d = k_{obs}$. The association rate constant, $k_a$, is obtained from the association phase by determining the slope of $k_{obs}$ plotted against analyte concentration, as shown in Equation S3

$$k_{obs} = k_a[A] + k_d \quad [S3]$$

$$K_{ads} = \frac{k_a}{k_d} \quad [S4]$$

TABLE 1 lists values for constants. TABLE 2 shows calibration fitting parameters. TABLE 3 lists sources of biologics.

TABLE 1

| Constants | Value |
| --- | --- |
| $k_a$ | 2.8 × 10$^6$ M$^{-1}$s$^{-1}$ |
| $K_d$ | 1.3 × 10$^{-2}$ s−1 |

TABLE 1-continued

| Constants | Value |
| --- | --- |
| $k_{ads}$ | 2 × 10$^8$ M$^{-1}$ |
| $k_d$ | 4.8 × 10$^{-9}$ M |

TABLE 2

|  | IL-2 | IL-6 | IL-8 |
| --- | --- | --- | --- |
| $A_1$ | 11.27 | −2.80 | 31.28 |
| $A_2$ | 11266.12 | 13125.64 | 11685.34 |
| C | 218.10 | 621.47 | 226.15 |
| P | 1.36 | 1.08 | 1.28 |
| Adj. $R^2$ | 0.986678 | 0.999946 | 0.995057 |

TABLE 3

| Clone #/Vendor | IL-2 | IL-4 | IL-6 | IL-8 |
| --- | --- | --- | --- | --- |
| Antigen | 14-8029/ eBioscience | 34-8049/ eBioscience | 148069/ eBioscience | 208/IL/R&D Systems |
| Capture Antibody | 555051/BD Biosciences | 8-D4-8/ eBioscience | MQ$_2$- 13A$_5$/eBioscience | 554716/BD Biosciences |
| Detection Antibody #1 | 555040/BD Biosciences |  | MQ$_2$- 31C$_3$/eBioscience | 554718/BD Biosciences |
| Detection Antibody #2 | MQ$_1$- 17H$_{12}$/ eBiosciences |  | BAF206/R&D Systems | BAF208/ R&D Systems |
| ELISA Kit | BD Biosciences |  | Abcam | BD Biosciences |

FIG. 1B shows the response from four representative microrings during the enzymatically enhanced detection of a 3125 pg/mL solution of IL-6. The primary, secondary, and tertiary binding responses for IL-6, secondary antibodies, and SA-HRP are all clearly visible in the inset but are dwarfed by the large signal associated with the deposition of 4-CNP, which leads to an ~11000 pm shift in microring resonance wavelength. Notably, microrings functionalized with an IgG isotype control (anti-IL-4) only show a bulk shift associated with the introduction of the methanolic 4-CN solution, and they return to their baseline levels when the running buffer is introduced across the sensor array, as indicated by the asterisk.

Figure 16:
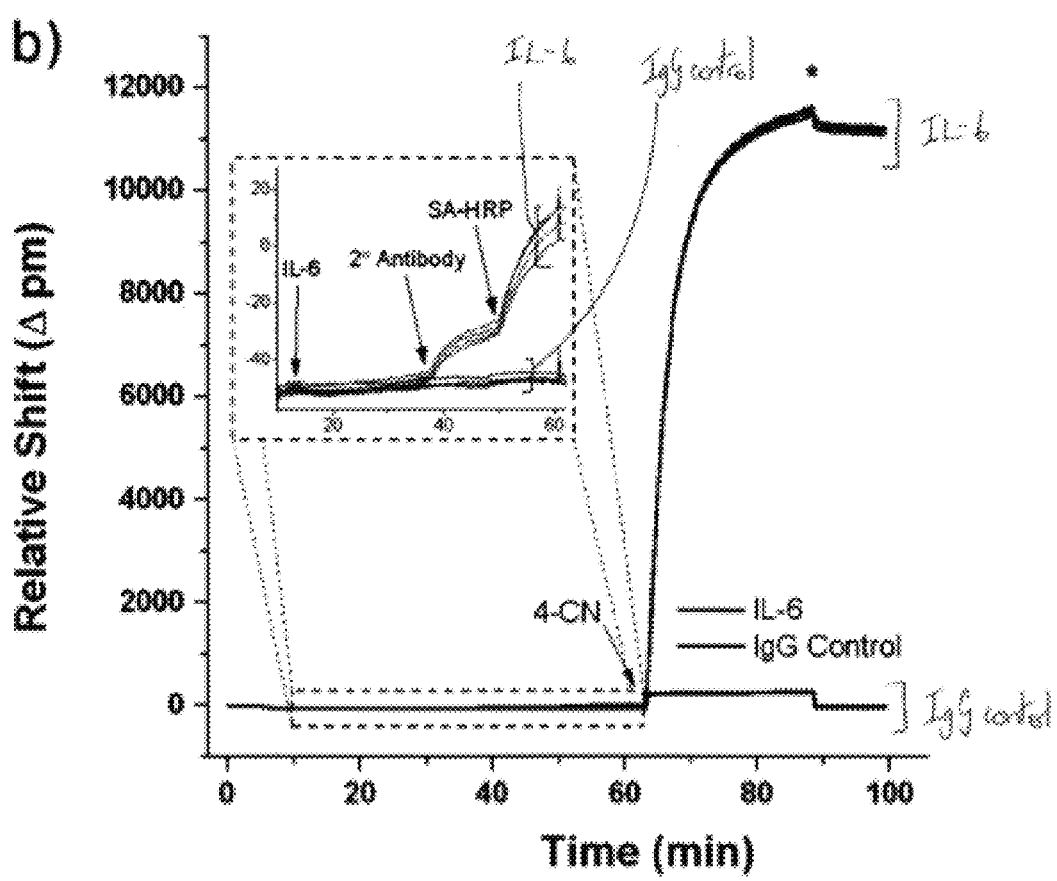
FIG. 16 depicts representative data corresponding to the inset above which illustrates the large signal gain obtained via 4-chloro-1-naphthon deposition using an IL-6 concentration of 3125 pg/mL.
Figure 17:
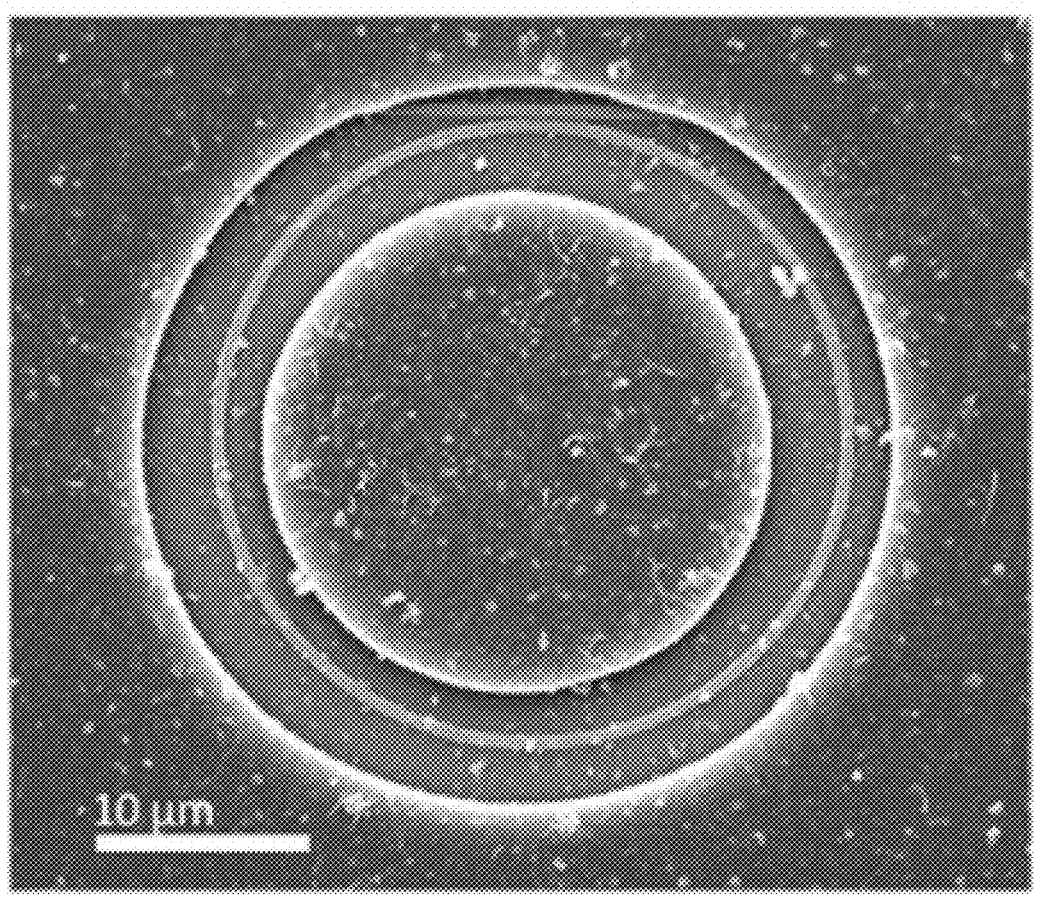
FIG. 17 depicts a scanning electron micrograph of an individual microring showing the discrete deposits of 4-CNP.

FIG. 17 is a scanning electron micrograph of a representative microring sensor used to acquire the data in FIG. 16 after the enzymatic enhancement step, clearly showing the presence of precipitated 4-CNP. SEM images from a microring used for a lower IL-6 concentration detection experiment, as well as a control microring, are shown in the Supporting Information. Higher-resolution SEM images reveal depositions at distinct locations as small as 50 nm, which may be the result of localized precipitation from single enzymes; however, more investigation is needed to substantiate this hypothesis. Interestingly, the real-time monitoring of 4-CNP deposition reveals a self-limiting enhancement after ~25 min, even in the presence of increasing concentrations of 4-CN. We propose that signal enhancement is ultimately limited by the physical occlusion of the enzyme by the local accumulation of precipitate.

The advantages of enzymatic signal amplification on the microring resonator platform are readily apparent when compared to linear signal enhancement strategies previously employed. For comparison, a secondary detection antibody alone enhanced the magnitude of the resonance wavelength shift relative to the primary antigen by ~3, and a bead-based approach yielded an additional factor of ~50 (Luchansky, M. S.; Bailey, R. C. Anal. Chem. 2010, 82, 1975-1981.; Kindt, J. T.; Bailey, R. C. Anal. Chem. 2012, 84, 8067-8074). In contrast, FIG. 16 illustrates a HRP-derived signal gain of $10^4$. Furthermore, this response is under nearly saturating concentrations; at lower antigen abundance, the amplification factor is even higher. However, at these lower concentrations the primary binding of the target antigen and even secondary antibody are not even observable. The magnitude of this response can be attributed to both the high turnover of HRP and the dense packing of the 4-CNP at the sensor surface, which overlaps strongly with the evanescent optical mode of the resonator.

Quantitative Detection

Figure 18:
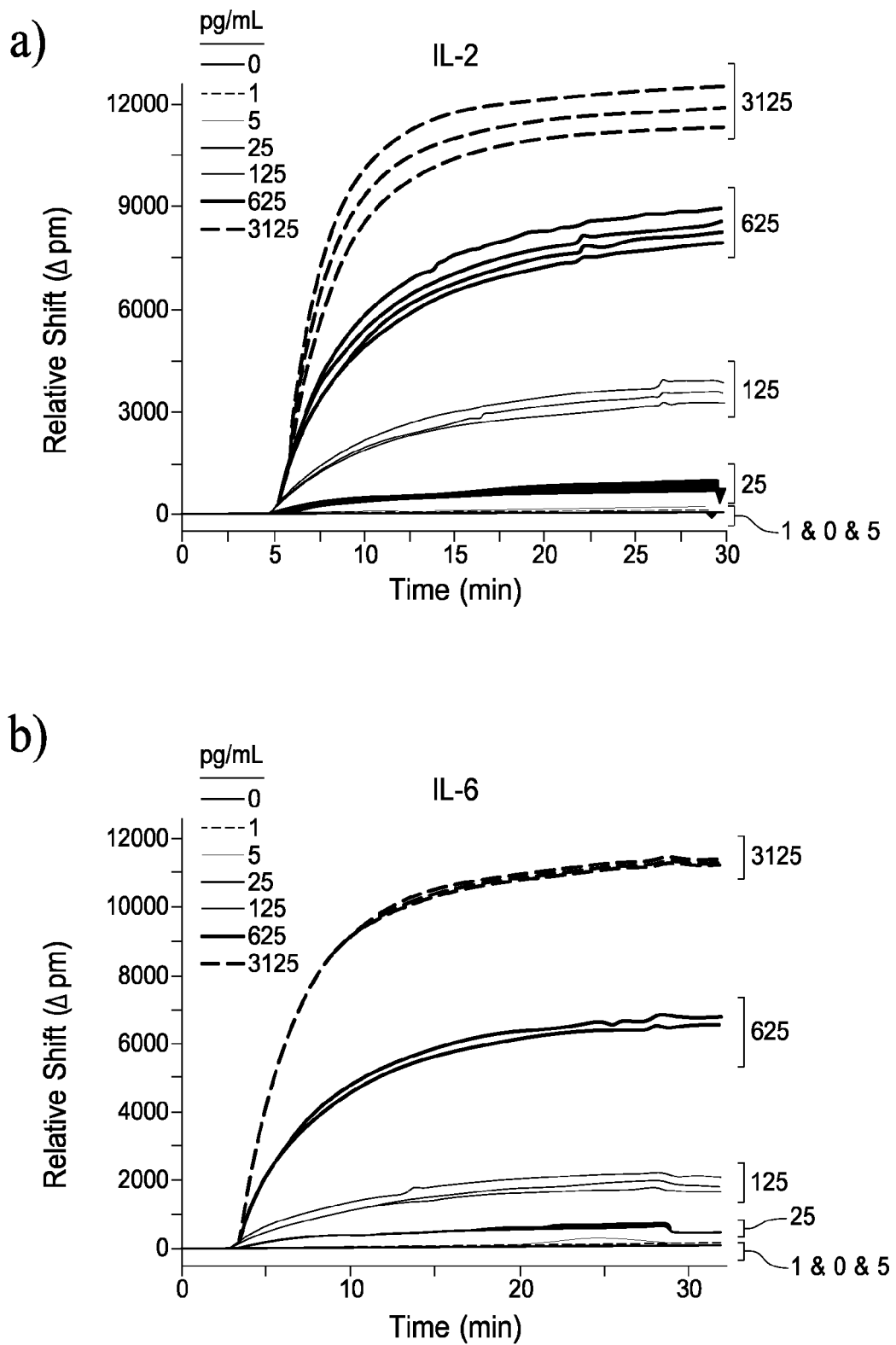
FIGS. 18A-18C depict the concentration dependent, real-time sensor response of 4-CN deposition observed to span a >3 order of magnitude dynamic range for all three interleukins studied.
FIGS. 18D-18F depict the associated calibration plots that illustrate a detection limit of 1 pg/mL for all three interleukins and 500 fg/mL for IL-8. Calibration plots are fit with logistic functions. Error bars represent the standard deviation of n=3-4 individual sensors for microring measurements.
Figure 18:
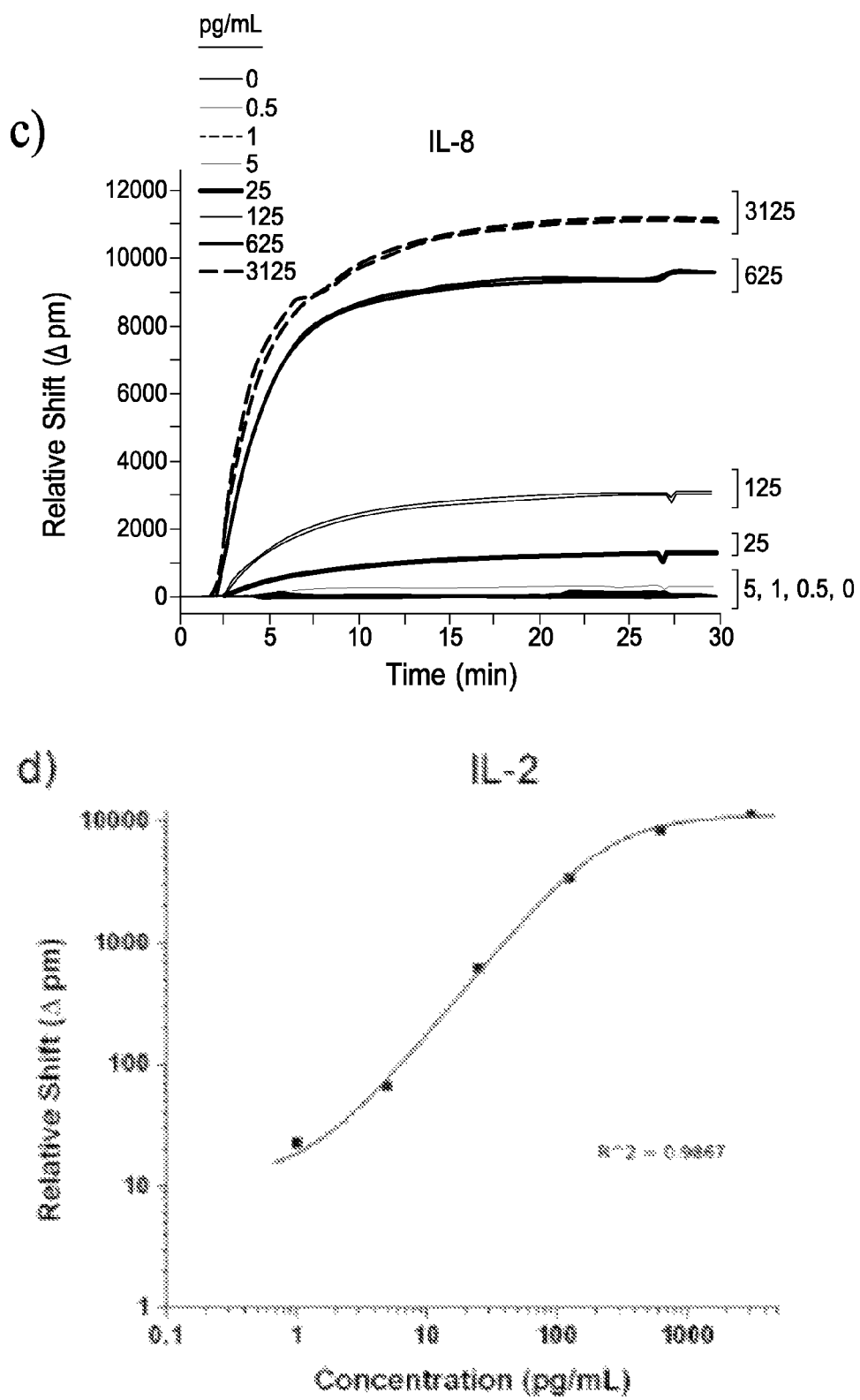
Figure 18:
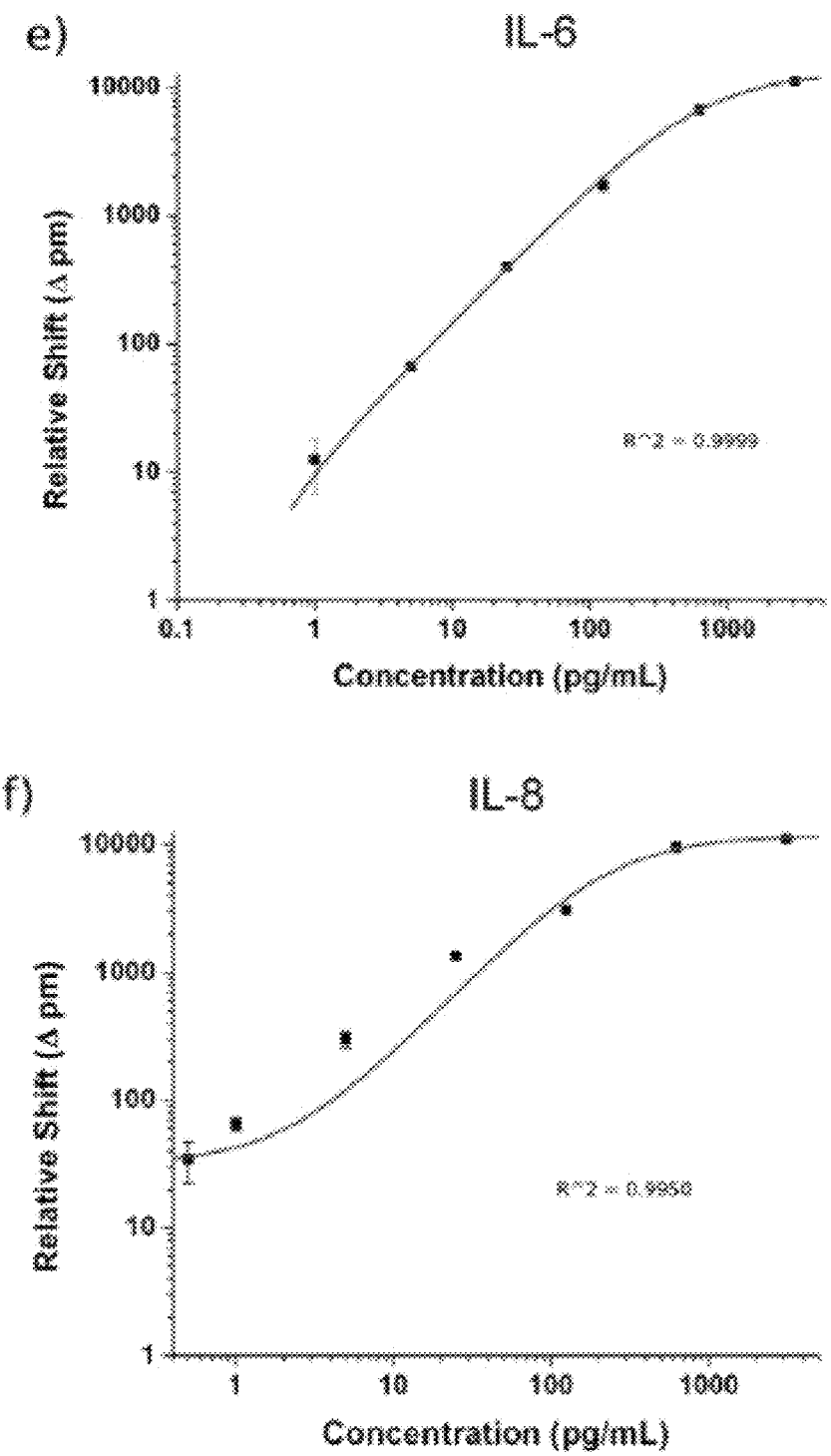

To establish the quantitative detection capability of this signal enhancement strategy by analyzing solutions containing different concentrations of three different interleukin targets (IL-2, IL-6, and IL-8) were analyzed over a concentration range of 1 pg/mL up to 3125 pg/mL. This represents a clinically relevant range, which includes both basal interleukin levels as well as elevated levels that are often correlated with an active immune response. FIGS. 18A-18C shows the realtime monitoring of the 4-CNP deposition process following exposure of the microrings to IL-2, IL-6, and IL-8, respectively, across this concentration range. FIGS. 18D-18F show the calibration curves resulting from plotting the HRP-enhanced resonance wavelength shift as a function of interleukin concentration. (Note that the calibration curves are plotted on a log-log plot for clarity.) For IL-2 and IL-6, the limit of detection, as defined by the response at 3σ of the baseline noise measured with control microrings, was 1 pg/mL, while the LOD for IL-8 was 500 fg/mL. These assays also demonstrated a 3 order of magnitude dynamic range, which while already quite broad, could be further extended to higher concentrations via either sample dilution or by quantitation using the measured secondary or even primary responses, as demonstrated previously (Luchansky, M. S.; Washburn, A. L.; McClellan, M. S.; Bailey, R. C. Lab Chip 2011, 11, 2042-2044). Combined, this approach would enable quantitation across 8 decades from 500 fg/mL to 50 g/mL without any alteration to the described assay protocol.

Detection in Biological Sample

After establishing important assay characteristics and metrics in a controlled buffer system, the assay was applied to measurements in a clinically relevant sample matrix, cerebrospinal fluid (CSF). CSF is a promising biofluid for biomarker-based diagnostics of diseases and disorders of the central nervous system as it is in direct contact with the extracellular space in the brain and contains important putative diagnostic markers (Neurol. 2010, 6, 131-144; Olson, L.; Humpel, C. Exp. Gerontol. 2010, 45, 41-46; Fagan, A. M.; Holtzman, D. M. Biomarkers Med. 2010, 4, 51-63; Hansson, 0.; Zetterberg, H.; Buchhave, P.; Londos, E.; Blennow, K.; Minthon, L. Lancet Neurol 2006, 5, 228-234). Due to the presence of the blood-brain barrier, CSF has been shown to have more disease diagnostic value than plasma-based analysis for some brain-related diseases (Llano, D. A.; Li, J. H.; Waring, J. F.; Ellis, T.; Devanarayan, V.; Witte, D. G.; Lenz, R. A. Alzheimer Dis. Assoc. Disord. 2012, 26, 322-328).

Figure 19:
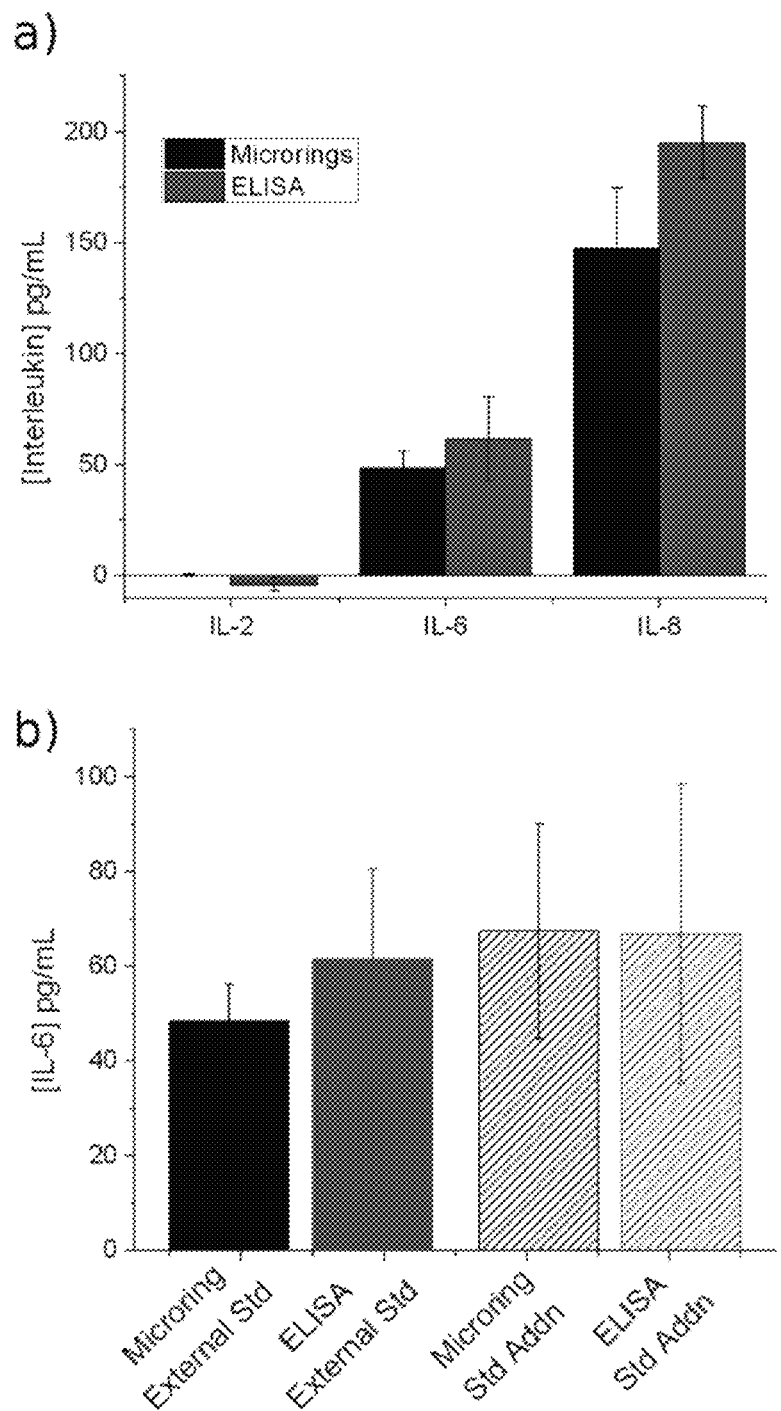
FIG. 19A depicts good agreement observed between ELISA and microring resonator based measurements of interleukin levels in CSF samples with the use of an external standard method. Additionally, the two assays showed comparable precision. Error bars represent the standard deviation of n=3-4 individual sensors for microring measurements and n=3 for ELISA.
FIG. 19B depicts a focused study on IL-6 levels that showed even better agreement with ELISA measurements when using a standard addition calibration method; however, as expected, the precision for both ELISA and microring measurements is reduced when using the standard addition method.

Aware that matrix effects could potentially interfere with quantitation in undiluted CSF, both external standard and standard addition calibration methods were employed and the results were correlated with traditional ELISA assays. It was anticipated that while standard addition should better compensate for matrix effects to give more accurate measurements, the extrapolation necessitated in this method might lead to reduced precision (Ellison, S. L. R.; Thompson, M. Analyst 2008, 133, 992-997). FIG. 19A shows good agreement between both the ELISA and microring-based quantitation of IL-8, IL-6, and IL-2 in pooled human CSF samples when using external standard calibration. In all cases, the precision is comparable between the two technologies and the microring measurements gave a somewhat lower concentration for IL-6 and IL-8. These discrepancies are likely due to complex matrix effects, which are known to differentially affect dissimilar detection technologies (Khuseyinova, N.; Imhof, A.; Trischler, G.; Rothenbacher, D.; Hutchinson, W. L.; Pepys, M. B.; Koenig, W. Clin. Chem. 2003, 49, 1691-1695). Importantly though, while variability between CSF samples and processing methods prohibits a directly quantitative comparison, the qualitative order of abundance, IL-8>IL-6>IL-2, agrees with literature reports (Llano, D. A.; Li, J. H.; Waring, J. F.; Ellis, T.; Devanarayan, V.; Witte, D. G.; Lenz, R. A. Alzheimer Dis. Assoc. Disord. 2012, 26, 322-328).

Figure 14:
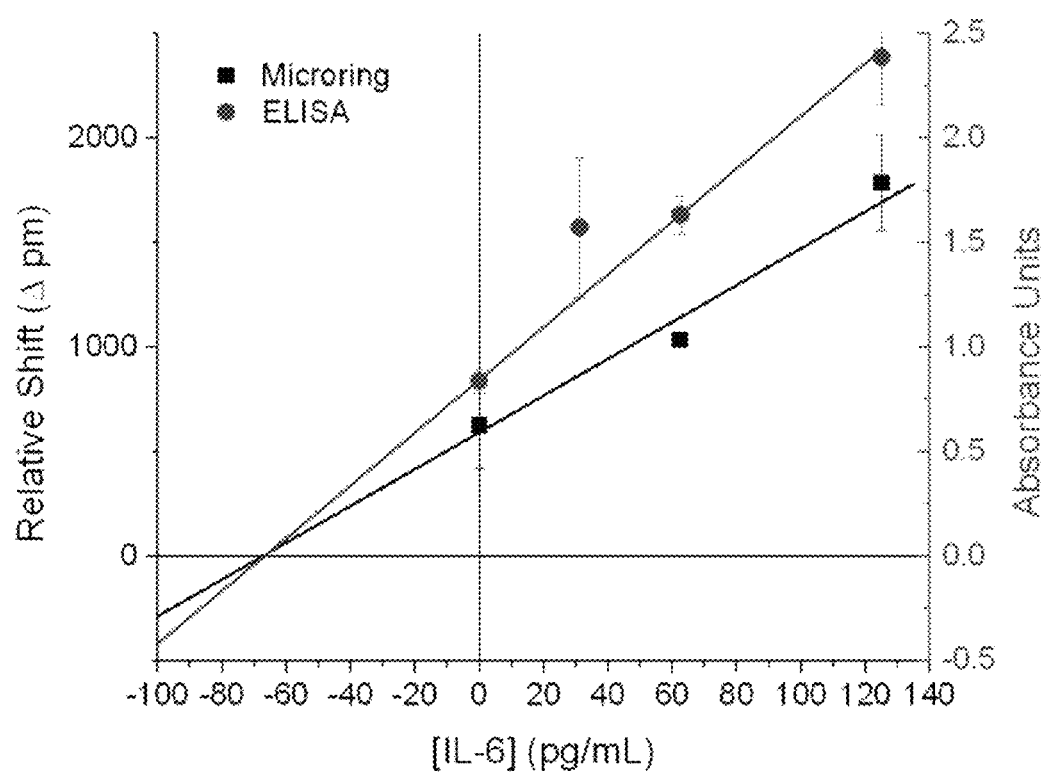
FIG. 14 depicts a comparison of IL-6 quantitation by the method of standard additions for both ELISA and microring resonators.
Figure 15:
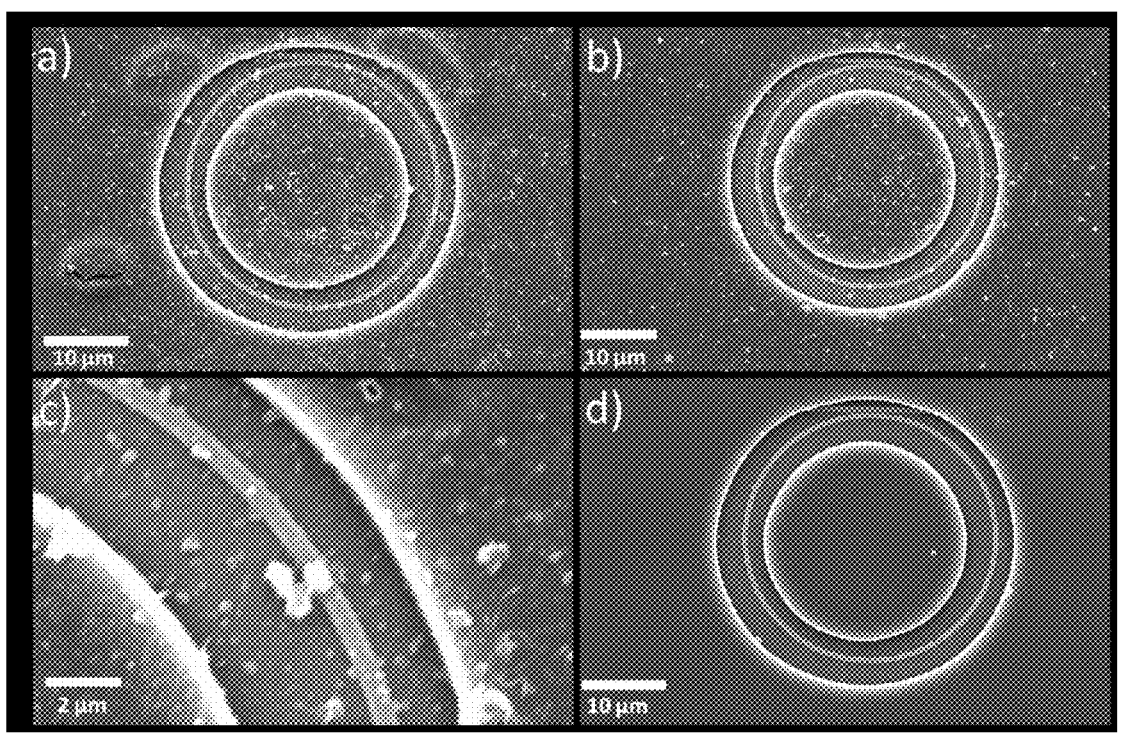
FIG. 15 depicts scanning electron micrographs of 3 different microrings with various IL-6 concentrations: a) 3125 pg/mL, b) 625 pg/mL, c) magnification of 625 pg/mL, d) 0 pg/mL. The heterogeneity of the precipitation process is readily observed, likely corresponding to localized deposition around surface-immobilized HRP enzymes. The images were captured on a JEOL 6060LV general purpose SEM at 15 kV.

To further probe the accuracy of our enzymatically enhanced microring resonator measurements, a focused study on IL-6 was performed using the method of standard additions to better compensate for matrix effects. As shown in FIG. 19B, the implementation of the standard addition method brings the measured concentrations into excellent agreement. Not surprisingly, the precision of the standard addition microring quantitation was reduced compared to the external standard calibration; however, an equivalent reduction in precision was noted for the ELISA measurement when subjected to an identical standard addition extrapolation. Data from standard additions are shown in FIG. 14.

Interleukins served as a challenging proof-of-principle system where low limits of detection are required for analysis within native biological samples. However, the generality of this signal enhancement strategy should lend it to be amenable to a wide variety of diagnostic targets and assay panels that require multiplexed and relatively rapid analyses. For applications which require still further increases in sensitivity, this assay could be modified through the conjugation of a multitude of enzymes to nanoparticles or other scaffolds or even the conjugation of clusters of enzyme-functionalized nanoparticles.

An enzymatic signal enhancement strategy has been integrated with a silicon photonic sensing platform to enable the multiplexed detection of interleukins within undiluted cerebrospinal fluid. The HRP-catalyzed oxidation of 4-CN results in deposition of an insoluble product onto the surface, which in turn elicits an incredibly large sensor response. The high gain of this modular signal amplification strategy allowed for ≤1 pg/mL limit of detection and a 3+ order of magnitude dynamic range in a relatively rapid (90 min) and multiplexed assay format. Comparison of CSF interleukin levels measured simultaneously using this technology were compared with individually performed ELISA assays and found to be in excellent agreement in terms of both accuracy and precision, helping to further establish this technological platform for clinical diagnostic applications.

The following references are each incorporated herein by reference in their entireties.

REFERENCES (1) Vandermeeren, M.; Mercken, M.; Vanmechelen, E.; Six, J.; Van de Voorde, A.; Martin, J.-J.; Cras, P. J. Neurochem. 1993, 61, 1828-1834.

(2) [0269] The following references are each incorporated herein by reference in their entireties.

REFERENCES (1) Vandermeeren, M.; Mercken, M.; Vanmechelen, E.; Six, J.; Van de Voorde, A.; Martin, J.-J.; Cras, P. J. Neurochem. 1993, 61, 1828-1834.
(2) Chen, S.; Svedendahl, M.; Duyne, R. P. V.; Kall, M. Nano Lett. 2011, 11, 1826-1830.
(3) Capule, C. C.; Yang, J. Anal. Chem. 2012, 84, 1786-1791.
(4) Rissin, D. M.; Kan, C. W.; Campbell, T. G.; Howes, S. C.; Fournier, D. R.; Song, L.; Piech, T.; Patel, P. P.; Chang, L.; Rivnak, A. J.; Ferrell, E. P.; Randall, J. D.; Provuncher, G. K.; Walt, D. R.; Duffy, D. C. Nat. Biotechnol. 2010, 28, 595-599.
(5) Clark, M. F.; Adams, A. N. J. Gen. Virol. 1977, 34, 475-483.
(6) eBioscience Enzyme Linked Immunosorbent Assay 2010, ELISA Protocols.
(7) SABiosciences Single Analyte ELISA Kits 2010, Product List.
(8) Li, Y.; Lee, H. J.; Corn, R. M. Anal. Chem. 2007, 79, 1082-1088.
(9) Luchansky, M. S.; Bailey, R. C. Anal. Chem. 2010, 82, 1975-1981.
(10) Luchansky, M. S.; Washburn, A. L.; McClellan, M. S.; Bailey, R. C. Lab Chip 2011, 11, 2042-2044.
(11) Luchansky, M. S.; Bailey, R. C. J. Am. Chem. Soc. 2011, 133, 20500-20506.
(12) Conyers, S. M.; Kidwell, D. A. Anal. Biochem. 1991, 192, 207-211.
(13) Hosoda, H.; Takasaki, W.; Oe, T.; Tsukamoto, R.; Nambara, T. Chem. Pharm. Bull. 1986, 34, 4177-4182.
(14) Fortin, E.; Mailley, P.; Lacroix, L.; Szunerits, S. Analyst 2006, 131, 186-193.
(15) Iqbal, M.; Gleeson, M. A.; Spaugh, B.; Tybor, F.; Gunn, W. G.; Hochberg, M.; Baehr-Jones, T.; Bailey, R. C.; Gunn, L. C. IEEE J. Sel. Top. Quantum Electron. 2010, 16, 654-661.
(16) Washburn, A. L.; Gunn, L. C.; Bailey, R. C. Anal. Chem. 2009, 81, 9499-9506.
(17) Byeon, J.-Y.; Bailey, R. C. Analyst 2011, 136, 3430-3433.
(18) Byeon, J.-Y.; Limpoco, F. T.; Bailey, R. C. Langmuir 2010, 26, 15430-15435.
(19) Gabay, C. Arthrit. Res. Ther. 2006, 8, S3.
(20) Gauldie, J.; Richards, C.; Harnish, D.; Lansdorp, P.; Baumann, H. Proc. Natl. Acad. Sci. U.S.A. 1987, 84, 7251-7255.
(21) Steensberg, A.; Dalsgaard, M. K.; Secher, N. H.; Pedersen, B. K. Brain. Behav. Immun. 2006, 20, 585-589.
(22) Bell, M. J.; Kochanek, P. M.; Doughty, L. A.; Carcillo, J. A.; Adelson, P. D.; Clark, R. S. B.; Wisniewski, S. R.; Whalen, M. J.; Dekosky, S. T. J. Neurotrauma 1997, 14, 451-457.
(23) Tarkowski, E.; Rosengren, L.; Blomstrand, C.; Wikkelso, C.; Jensen, C.; Ekholm, S.; Tarkowski, A. Stroke 1995, 26, 1393-1398.
(24) Stelmasiak, Z.; Koziol-Montewka, M.; Dobosz, B.; Rejdak, K.; Bartosik-Psujek, H.; Mitosek-Szewczyk, K.; Belniak-Legieć, E. Med. Sci. Monit. 2000, 6, CR1104-1108.
(25) Baker, D. G.; Ekhator, N. N.; Kasckow, J. W.; Hill, K. K.; Zoumakis, E.; Dashevsky, B. A.; Chrousos, G. P.; Geracioti Jr, T. D. Neuroimmunomodulation 2001, 9, 209-217.
(26) Tsai, C. Y.; Wu, T. H.; Tsai, S. T.; Chen, K. H.; Thajeb, P.; Lin, W. M.; Yu, H. S.; Yu, C. L. Scand. J. Rheumatol. 1994, 23, 57-63.
(27) Anoop, A.; Singh, P. K.; Jacob, R. S.; Maji, S. K. Int. J. Alzheimers Dis. 2010, 2010, 1-12.
(28) Llano, D. A.; Li, J.; Waring, J. F.; Ellis, T.; Devanarayan, V.; Witte, D. G.; Lenz, R. A. Alzheimer Dis. Assoc. Disord. 2011, in press, 10.1097/WAD.0b013e31823b2728.
(29) Blum-Degena, D.; Muller, T.; Kuhn, W.; Gerlach, M.; Przuntek, H.; Riederer, P. Neurosci. Lett. 1995, 202, 17-20.
(30) Jia, J. P.; Meng, R.; Sun, Y. X.; Sun, W. J.; Ji, X. M.; Jia, L. F. Neurosci. Lett. 2005, 383, 12-16.
(31) Martinez, M.; Fernandez-Vivancos, E.; Frank, A.; De la Fuente, M.; Hernanz, A. Brain Res. 2000, 869, 216-219.
(32) Engelborghs, S.; De Brabander, M.; De Cree, J.; D'Hooge, R.; Geerts, H.; Verhaegen, H.; De Deyn, P. P. Neurochem. Int. 1999, 34, 523-530.
(33) Marz, P.; Heese, K.; Hock, C.; Golombowski, S.; Muller-Spahn, F.; Rose-John, S.; Often, U. Neurosci. Lett. 1997, 239, 29-32.
(34) Tarkowski, E.; Blennow, K.; Wallin, A.; Tarkowski, A. J. Clin. Immunol. 1999, 19, 223-230.
(35) Huell, M.; Strauss, S.; Volk, B.; Berger, M.; Bauer, J. Acta Neuropathol. (Berl). 1995, 89, 544-551.
(36) Sokolova, A.; Hill, M. D.; Rahimi, F.; Warden, L. A.; Halliday, G. M.; Shepherd, C. E. Brain Pathol. 2009, 19, 392-398.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:
1. A method of detecting interleukin-2 (IL-2) comprising:
   (a) obtaining a fluidic cell comprising an optical ring resonator having a first anti-cytokine antibody attached thereto, wherein the first anti-cytokine antibody is anti-IL-2 from clone 555051 antibody;
   (b) contacting the first anti-cytokine antibody with a sample comprising IL-2 that selectively binds to the anti-cytokine antibody;

(c) contacting the bound IL-2 with a second anti-cytokine antibody that selectively binds to the IL-2, wherein the second anti-cytokine antibody is a biotinylated anti-IL-2 from clone 555040 antibody;

(d) contacting the biotinylated second anti-cytokine antibody with a streptavidin-horseradish peroxidase conjugate;

(e) contacting the horseradish peroxidase with a substantially continuous flow of a solution comprising 4-chloro-1-naphthol and hydrogen peroxide, under conditions that oxidize 4-chloro-1-naphthol to 4-chloro-1-naphthon, whereby the 4-chloro-1-naphthon precipitates on the surface of the optical ring resonator during the substantially continuous flow of the solution; and (f) measuring a change in resonance wavelengths of the optical ring resonator, thereby indicating the presence of the IL-2.

2. The method of claim 1, wherein the concentration of hydrogen peroxide is less than about 0.003%.

3. The method of claim 1, wherein a concentration of the cytokine less than about 100 pg/ml is detected.

4. The method of claim 1, wherein a continuous flow of reagents contacting the optical ring resonator having a first anti-cytokine antibody attached thereto is maintained for step (b).

5. The method of claim 1, wherein a substantially continuous flow of reagents contacting the optical ring resonator having a first anti-cytokine antibody attached thereto is maintained for each of steps (b), (c), (d), and (e).

6. The method of claim 1, wherein a continuous flow of reagents contacting the optical ring resonator having a first anti-cytokine antibody attached thereto is maintained for each of steps (b), (c), (d), and (e).

7. The method of claim 1, wherein steps (b)-(e) comprise maintaining a flow of reagents contacting the optical ring resonator having a first anti-cytokine antibody attached thereto.

8. The method of claim 7, wherein the flow rate of the reagents is about 30 µL/min.

9. The method of claim 1, wherein a continuous flow of the solution is maintained for step (e).

10. The method of claim 9, wherein the continuous flow of the solution is maintained for steps (e) and (f).

* * * * *

UNITED STATES PATENT AND TRADEMARK OFFICE
CERTIFICATE OF CORRECTION

PATENT NO. : 9,983,206 B2
APPLICATION NO. : 14/209746
DATED : May 29, 2018
INVENTOR(S) : Ryan C. Bailey et al.

It is certified that error appears in the above-identified patent and that said Letters Patent is hereby corrected as shown below:

On the Title Page

In Column 1 (Notice) at Line 3, After "0 days." delete "days.".

In the Specification

In Column 7 at Line 59, Change "biolinylated" to --biotinylated--.

In Column 8 at Line 16, Change "biolinylated" to --biotinylated--.

In Column 12 at Line 60, Change "labelfree" to --label free--.

In Column 17 at Line 63, Change "(sdFvincluding" to --(sdFv) (including--.

In Column 19 at Line 12, Change "Denhart's" to --Denhardt's--.

In Column 20 at Line 5, Change "xathanine, hypoxathanine," to --xanthine, hypoxanthine,--.

In Column 20 at Line 8, Change "2-thioLiracil," to --2-thioUracil,--.

In Column 20 at Line 35, Change "Conavalia" to --Canavalia--.

In Column 20 at Line 36, Change "stramoniuim," to --stramonium,--.

In Column 24 at Line 56, Change "hemagluttinin" to --hemagglutinin--.

In Column 26 at Line 18, Change "nanocyrstals" to --nanocrystals--.

In Column 32 at Line 8, Change "ethylbenzthiazolone)," to --ethylbenzothiazolone),--.

Signed and Sealed this
Eleventh Day of September, 2018

Andrei Iancu
*Director of the United States Patent and Trademark Office*

CERTIFICATE OF CORRECTION (continued)
U.S. Pat. No. 9,983,206 B2

In Column 32 at Line 8-9, Change "aminoantipyrene" to --aminoantipyrine--.

In Column 32 at Line 11, Change "ethylbenzthiazolone)," to --ethylbenzothiazolone),--.

In Column 32 at Line 53, Change "MΩ1-" to --MQ1- --.

In Column 39 at Line 50 (Approx.), Change "S3" to --S3.--.

In Column 39 at Line 66, Change "s-1" to --$s^{-1}$--.

In Column 41 at Line 41, Change "g/mL" to --µg/mL--.

In Column 43 at Line 1-8 (Approx.), Above "(2)" delete "(2) [0269] The following references are each incorporated herein by reference in their entireties.
REFERENCES
    (1) Vandermeeren, M.; Mercken, M.; Vanmechelen, E.; Six, J.; Van de Voorde, A.; Martin, J.-J.; Cras, P. J. Neurochem. 1993, 61, 1828-1834.".

In Column 44 at Line 25, Change "Often," to --Otten,--.